United States Patent
Chen et al.

(10) Patent No.: US 11,466,024 B2
(45) Date of Patent: Oct. 11, 2022

(54) BICYLIC COMPOUND ACTING AS AN INHIBITOR

(71) Applicants: CHIA TAI TIANQING PHARMACEUTICAL GROUP CO., LTD., Lianyungang (CN); MEDSHINE DISCOVERY INC., Nanjing (CN)

(72) Inventors: Kevin X Chen, Lianyungang (CN); Kai Zhou, Lianyungang (CN); Yanxin Yu, Lianyungang (CN); Boyu Hu, Lianyungang (CN); Linghui Wu, Lianyungang (CN); Xiaoyuan Chen, Lianyungang (CN); Jiangfeng Lin, Lianyungang (CN); Haomin Chen, Lianyungang (CN); Xiangjian Wang, Lianyungang (CN); Xiquan Zhang, Lianyungang (CN); Xin Tian, Lianyungang (CN); Hongjiang Xu, Lianyungang (CN)

(73) Assignees: Chia Tai Tianqing Pharmaceutical Group Co., Ltd., Lianyungang (CN); Medshine Discovery Inc., Jiangsu (CN)

( * ) Notice: Subject to any disclaimer, the term of this patent is extended or adjusted under 35 U.S.C. 154(b) by 0 days.

(21) Appl. No.: 16/635,916

(22) PCT Filed: Jul. 27, 2018

(86) PCT No.: PCT/CN2018/097551
§ 371 (c)(1),
(2) Date: Jan. 31, 2020

(87) PCT Pub. No.: WO2019/024809
PCT Pub. Date: Feb. 7, 2019

(65) Prior Publication Data
US 2020/0231597 A1   Jul. 23, 2020

(30) Foreign Application Priority Data

Aug. 1, 2017 (CN) .......................... 201710650300.8

(51) Int. Cl.
*C07D 495/04* (2006.01)

(52) U.S. Cl.
CPC ................. *C07D 495/04* (2013.01)

(58) Field of Classification Search
None
See application file for complete search history.

(56) References Cited

U.S. PATENT DOCUMENTS

| | | | |
|---|---|---|---|
| 8,138,217 B2 | 3/2012 | Faucelli et al. |
| 9,150,508 B2 | 10/2015 | Birault et al. |
| 9,242,972 B2 | 1/2016 | Birault et al. |
| 9,428,452 B2 | 8/2016 | Birault et al. |
| 9,540,318 B2 | 1/2017 | Birault et al. |
| 9,682,977 B2 | 6/2017 | Das et al. |
| 9,796,710 B2 | 10/2017 | Claremon et al. |
| 9,868,748 B2 | 1/2018 | Claremon et al. |
| 10,047,085 B2 | 8/2018 | Claremon et al. |

(Continued)

FOREIGN PATENT DOCUMENTS

| | | |
|---|---|---|
| CN | 1946395 A | 4/2007 |
| CN | 105980364 A | 9/2016 |

(Continued)

OTHER PUBLICATIONS

Schafer, S., Kolkhof, P. Failure is an option: learning from unsuccessful proof-of-concept trials. Drug Discovery Today. Nov. 13, 2008, 913-916.*

(Continued)

*Primary Examiner* — Po-Chih Chen
(74) *Attorney, Agent, or Firm* — Muncy, Geissler, Olds & Lowe, P.C.

(57) ABSTRACT

A bicyclic compound acting as a RORγ inhibitor. Provided are a compound of formula (I) or a pharmaceutically acceptable salt thereof, the compound having a structure as represented by formula (I-A) or formula (I-B). The provided compound of formula (I-A) or formula (I-B) or pharmaceutically acceptable salt thereof has good RORγ inhibitory activities, being expected to be used for treating diseases mediated by RORγ receptors in a mammal.

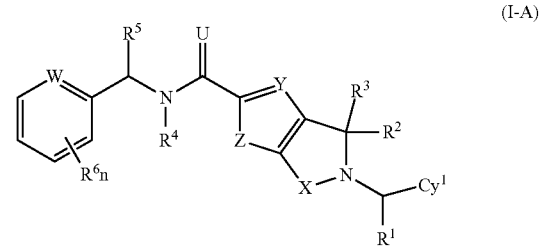

(I-A)

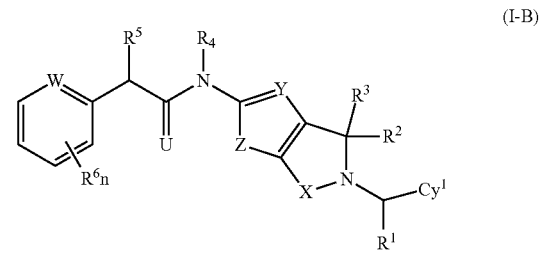

(I-B)

20 Claims, 3 Drawing Sheets

(56) References Cited

U.S. PATENT DOCUMENTS

| | | |
|---|---|---|
| 10,087,184 B2 | 10/2018 | Claremon et al. |
| 10,399,976 B2 | 9/2019 | Claremon et al. |
| 2005/0026984 A1 | 2/2005 | Bigot et al. |
| 2016/0304478 A1 | 10/2016 | Birault et al. |

FOREIGN PATENT DOCUMENTS

| | | |
|---|---|---|
| WO | WO 2004/007504 A1 | 1/2004 |
| WO | WO 2005/074922 A1 | 8/2005 |
| WO | WO 2007/009898 A1 | 1/2007 |
| WO | WO 2007/113198 A2 | 10/2007 |
| WO | WO2013045431 A1 | 4/2013 |
| WO | WO2013160418 A1 | 10/2013 |
| WO | WO2013160419 A1 | 10/2013 |
| WO | WO2014179564 A1 | 11/2014 |
| WO | WO 2015/008234 A1 | 1/2015 |
| WO | WO 2015/101928 A1 | 7/2015 |
| WO | WO2015116904 A1 | 8/2015 |
| WO | WO2016061160 A1 | 4/2016 |
| WO | WO 2017/075178 A1 | 5/2017 |
| WO | WO2019244047 * | 12/2019 |

OTHER PUBLICATIONS

Horig, H., Pullman, W. From bench to clinic and back: Perspective on the 1st IQPC Translational Research conference. Journal of Translational Medicine. Dec. 2, 2004, 44.*

Fitzpatrick, et al., VPR-254: an inhibitor of ROR-gamma T with potential utility for the treatment of inflammatory bowel disease. Inflammopharmacology, 2020, 28, 499-511.*

"RN: 1216401-55-6, 933236-63-6, 932996-64-0," STN Registry (Apr. 4, 2010).

Cui et al., "BCR-ABL tyrosine kinase inhibitor pharmacophore model derived from a series of phenylaminopyrimidine-based (PAP) derivatives," Bioorganic & Medicinal Chem Letts, vol. 23, pp. 2442-2450 (2013).

Christian Gege, "Retinoid-related orphan receptor γ t modulators: comparison of Glenmark's me-too patent application (WO2015008234) with the originator application from Merck Sharp and Dohme (WO2012106995)," Expert Opinion, informa healthcare, pp. 1-7 (2015).

Wang et al., "Screening of nuclear receptor ROR γt inhibitor and its effect on IL-17A expression," Immunological Journal, vol. 32, No. 9, pp. 777-780 (Sep. 9, 2016).

* cited by examiner

BICYCLIC COMPOUND ACTING AS AN INHIBITOR

This nonprovisional application is a National Stage of International Application No. PCT/CN2018/097551, which was filed on Jul. 27, 2018, and which claims priority to Chinese Patent Application No. 201710650300.8, which was filed in China on Aug. 1, 2017, and which are both herein incorporated by reference.

TECHNICAL FIELD

The present disclosure relates to a bicyclic compound acting as a RORγ inhibitor, and belongs to the field of medicinal chemistry.

BACKGROUND

Retinoic acid-related orphan nuclear receptor (ROR) is a member of the nuclear receptor family, and is capable of regulating a variety of physiological and biochemical processes. The ROR family includes three types of RORα, RORβ, and RORγ. These three different RORs may be expressed in different tissues and regulate different physiological processes. RORα is mainly distributed in liver, skeletal muscle, skin, lung, adipose tissue, kidney, thymus and brain; RORβ mainly acts on the central nervous system; and RORγ may be expressed in many tissues, including liver, animal fat, and skeletal muscle.

RORγ has two subtypes: RORγ1 and RORγt (RORγ2). RORγ1 is expressed in many tissues such as thymus, muscle, kidney, and liver, while RORγt is only expressed in immune cells. RORγt is considered to be capable of regulating the differentiation of T cells, such as T helper 17 (Th17) cells. Th17 is a class of T helper cells, and this kind of cells may produce interleukin 17 (IL-17) and other cytokines. Th17 cells are associated with the pathology of numerous autoimmune and inflammatory diseases, said diseases include, but are not limited to, psoriasis, multiple sclerosis, rheumatoid arthritis, Crohn's disease, asthma, chronic obstructive pulmonary disease, Behcet's disease, irritable bowel syndrome, and the like.

In the prior art, the patent applications of Vitae Pharmaceuticals Inc., such as WO2014179564, WO2015116904 and WO2016061160, and the patent applications of GlaxoSmithKline, such as WO2013045431, WO2013160418 and WO2013160419, all disclose a series of compounds that may be used as RORγ inhibitors. In view of the great potential value of RORγ inhibitors, it is quite necessary to further seek for compounds with inhibitory function on RORγ.

SUMMARY

The present disclosure relates to a compound of formula (I) or a pharmaceutically acceptable salt thereof, wherein the compound of formula (I) has a structure represented by formula (I-A) or formula (I-B), Formula I-A

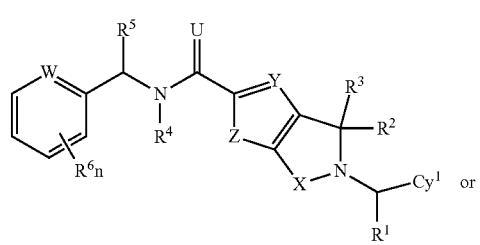

or

Formula I-B

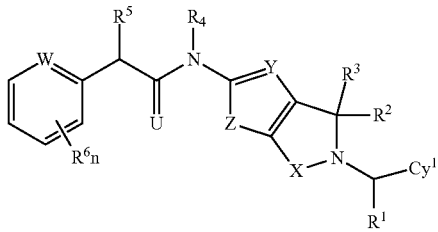

wherein,

X is $CR^7R^8$ or $NR^9$;

Y is $CR^{10}$;

Z is $CR^{11}R^{12}$, $NR^{13}$, —O—, or —S—;

U is or

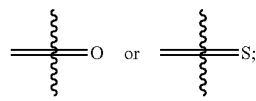

W is CH or N;

$Cy^1$ is selected from 3- to 6-membered cycloalkyl, 6- to 10-membered aryl, or 5- to 10-membered heteroaryl, which is optionally substituted by one or more $R^{16}$;

$R^1$, $R^4$, $R^9$, and $R^{13}$ are independently selected from hydrogen or $C_{1-6}$ alkyl;

$R^2$ and $R^3$ are independently selected from hydrogen, halogen, amino, hydroxyl, nitro, cyano, or $C_{1-6}$ alkyl; or $R^2$ and $R^3$ form

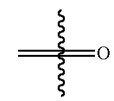

together; or $R^2$ and $R^3$ together with the C atom to which they are attached form a 3- to 6-membered cycloalkyl;

$R^5$ is selected from hydrogen or $C_{1-6}$ alkyl; said $C_{1-6}$ alkyl is optionally substituted by one or more hydroxyl, amino, nitro, cyano, halogen, $C_{1-4}$ alkoxy, $C_{1-4}$ alkylamino, or di($C_{1-4}$ alkyl)amino;

n is 0, 1, 2, 3, 4, or 5;

$R^6$ is selected from hydroxyl, amino, nitro, cyano, halogen, or

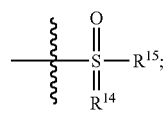

$R^7$ and $R^8$ are independently selected from hydrogen, halogen, amino, hydroxyl, nitro, cyano, or $C_{1-6}$ alkyl, wherein the $C_{1-6}$ alkyl is optionally substituted by halogen, amino, hydroxyl, nitro, cyano, or 3- to 6-membered cycloalkyl; or $R^7$ and $R^8$ form

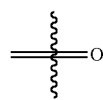 [SMILES: *=O]

together; or $R^7$ and $R^8$ together with the C atom to which they are attached form a 3- to 6-membered cycloalkyl;

$R^{10}$ is selected from hydrogen, $C_{1-6}$ alkyl, halogen, amino, hydroxyl, nitro, cyano, or $C_{1-6}$ haloalkyl;

$R^{11}$ and $R^{12}$ are independently selected from hydrogen, halogen, amino, hydroxyl, nitro, cyano, or $C_{1-6}$ alkyl; or $R^{11}$ and $R^{12}$ form

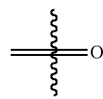 [SMILES: *=O]

together; or $R^1$ and $R^{12}$ together with the C atom to which they are attached form a 3- to 6-membered cycloalkyl;

$R^{14}$ is present or not present; when $R^{14}$ is present,

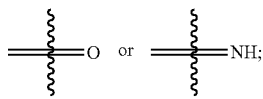

is selected from or

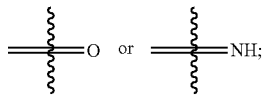

$R^{15}$ is selected from $C_{1-6}$ alkyl or $C_{1-6}$ alkoxy;

$R^{16}$ is selected from hydroxyl, amino, nitro, cyano, halogen, $C_{1-4}$ alkyl, $C_{1-4}$ haloalkyl, $C_{1-4}$ alkoxy, and $C_{1-4}$ haloalkoxy;

when the compound of formula (I) has a structure represented by formula (I-A), X is $CR^7R^8$, U is

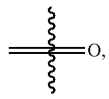

Y is $CR^{10}$ and W is CH, then $Cy^1$ is not a benzene ring; and when the compound of formula (I) has a structure represented by formula (I-B) and Y is N, Z is not S.

In some embodiments, U is

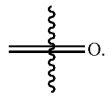

In some typical embodiments, U is

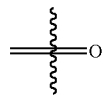

and W is CH.

In some typical embodiments, U is

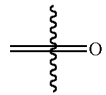

and W is N.

In some embodiments, X is $CR^7R^8$ or $NR^9$; wherein $R^7$ and $R^8$ are independently selected from hydrogen, fluorine, chlorine, bromine, iodine, amino, hydroxyl, nitro, cyano, or $C_{1-3}$ alkyl, wherein the $C_{1-3}$ alkyl is optionally substituted by fluorine, chlorine, bromine, iodine, amino, hydroxyl, nitro, cyano, or 3- to 6-membered cycloalkyl; or $R^7$ and $R^8$ form

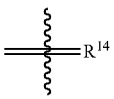

together; or $R^7$ and $R^8$ together with the C atom to which they are attached form cyclopropyl, cyclobutyl, cyclopentyl, or cyclohexyl; $R^9$ is selected from hydrogen or $C_{1-3}$ alkyl.

In some typical embodiments, X is $CR^7R^8$; wherein $R^7$ and $R^8$ are independently selected from hydrogen, methyl, ethyl, or isopropyl, wherein methyl, ethyl or isopropyl is optionally substituted by cyclopropyl; or $R^7$ and $R^8$ form

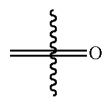

together; or $R^7$ and $R^8$ together with the C atom to which they are attached form cyclopropyl.

In some more typical embodiments, X is $CH_2$, $C(CH_3)_2$, C=O, $CHCH(CH_3)_2$,

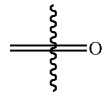

, or

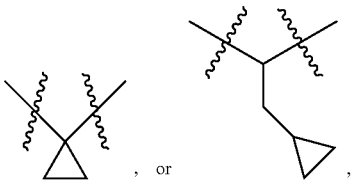 [SMILES: *C1(*)CC1 ; *C(*)CC1CC1]

In some most typical embodiments, X is

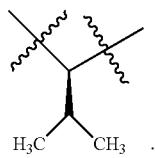

In some embodiments, Y is $CR^{10}$; wherein $R^{10}$ is selected from hydrogen, $C_{1-3}$ alkyl, fluorine, chlorine, bromine, iodine, amino, hydroxyl, nitro, cyano, or $C_{1-3}$ fluoroalkyl.

In some typical embodiments, Y is $CR^{10}$; wherein $R^{10}$ is selected from hydrogen, methyl, fluorine, chlorine, cyano, or $CF_3$.

In some more typical embodiments, Y is CH.

In some embodiments, Z is $CR^{11}R^{12}$, $NR^{13}$, —O—, or —S—; wherein $R^{11}$ and $R^{12}$ are independently selected from hydrogen, fluorine, chlorine, bromine, iodine, amino, hydroxyl, nitro, cyano, or $C_{1-3}$ alkyl; or $R^{11}$ and $R^{12}$ form

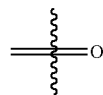

together; or $R^1$ and $R^{12}$ together with the C atom to which they are attached form cyclopropyl, cyclobutyl, cyclopentyl, or cyclohexyl; $R^{13}$ is selected from hydrogen or $C_{1-3}$ alkyl.

In some typical embodiments, Z is —O— or —S—.

In some more typical embodiments, Z is —S—.

In some embodiments, $Cy^1$ is selected from cyclohexyl or phenyl, which is optionally substituted by one or more $R^{16}$; wherein $R^{16}$ is selected from hydroxyl, amino, nitro, cyano, fluorine, chlorine, bromine, iodine, $C_{1-2}$ alkyl, $C_{1-2}$ haloalkyl, $C_{1-2}$ alkoxy, and $C_{1-2}$ haloalkoxy.

In some typical embodiments, $Cy^1$ is selected from cyclohexyl or phenyl, which is optionally substituted by one or more $R^{16}$; wherein $R^{16}$ is selected from $C_{1-2}$ fluoroalkyl, $C_{1-2}$ chloroalkyl, $C_{1-2}$ bromoalkyl, or $C_{1-2}$ iodoalkyl.

In some more typical embodiments, $Cy^1$ is selected from cyclohexyl or phenyl, which is optionally substituted by one $CF_3$.

In some more typical embodiments, $Cy^1$ is selected from

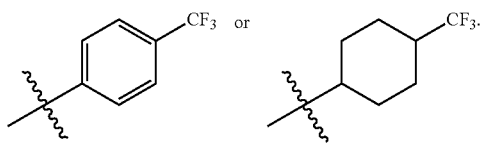 [SMILES: *c1ccc(C(F)(F)F)cc1 ; *C1CCC(C(F)(F)F)CC1]

In some most typical embodiments, $Cy^1$ is selected from

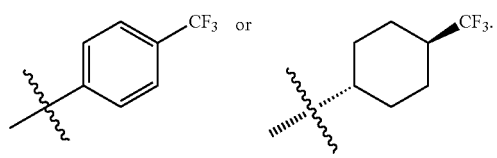

In some embodiments, $R^1$ and $R^4$ are selected from hydrogen or $C_{1-3}$ alkyl.

In some typical embodiments, both of $R^1$ and $R^4$ are hydrogen.

In some embodiments, $R^2$ and $R^3$ are independently selected from hydrogen, fluorine, chlorine, bromine, iodine, amino, hydroxyl, nitro, cyano, or $C_{1-3}$ alkyl; or $R^2$ and $R^3$ form

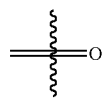 [SMILES: *=O]

together; or $R^2$ and $R^3$ together with the C atom to which they are attached form cyclopropyl, cyclobutyl, cyclopentyl, or cyclohexyl.

In some typical embodiments, $R^2$ and $R^3$ are independently selected from hydrogen, methyl, ethyl, or isopropyl; or $R^2$ and $R^3$ form

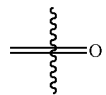 [SMILES: *=O]

together; or $R^2$ and $R^3$ together with the C atom to which they are attached form cyclopropyl.

In some more typical embodiments, $R^2$ and $R^3$ are both hydrogen.

In some more typical embodiments, $R^2$ and $R^3$ are both methyl.

In some more typical embodiments, $R^2$ is hydrogen, and $R^3$ is isopropyl.

In some more typical embodiments, $R^2$ and $R^3$ form

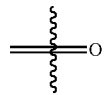 [SMILES: *=O]

together.

In some more typical embodiments, $R^2$ and $R^3$ together with the C atom to which they are attached form cyclopropyl.

In some embodiments, $R^5$ is selected from hydrogen or $C_{1-3}$ alkyl; said $C_{1-3}$ alkyl is optionally substituted by one or more hydroxyl, amino, nitro, cyano, fluorine, chlorine, bromine, iodine, $C_{1-2}$ alkoxy, $C_{1-2}$ alkylamino, or di($C_{1-2}$ alkyl) amino.

In some typical embodiments, $R^5$ is selected from hydrogen or methyl; said methyl is optionally substituted by one hydroxyl or methoxy.

In some more typical embodiments, $R^5$ is selected from hydrogen, methyl, hydroxymethyl, or —$CH_2OCH_3$.

In some most typical embodiments, $R^5$ is hydrogen.

In some embodiments, n is 0, 1, or 2.

In some typical embodiments, n is 1.

In some embodiments, $R^6$ is selected from hydroxyl, amino, nitro, cyano, fluorine, chlorine, bromine, iodine,

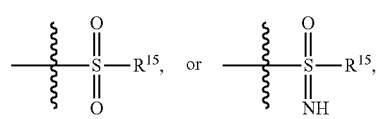

wherein $R^{15}$ is selected from $C_{1-3}$ alkyl or $C_{1-3}$ alkoxy.

In some typical embodiments, $R^6$ is selected from

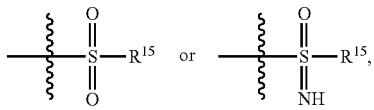

wherein $R^{15}$ is selected from methyl or ethyl.

In some more typical embodiments, $R^6$ is selected from

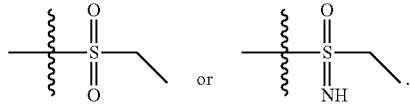

In some embodiments,

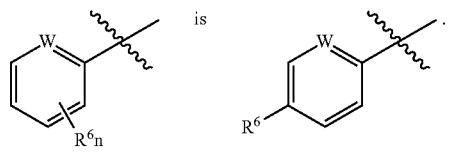

In some typical embodiments,

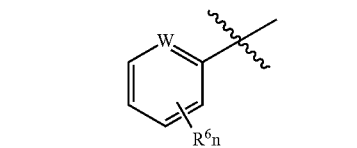

is selected from

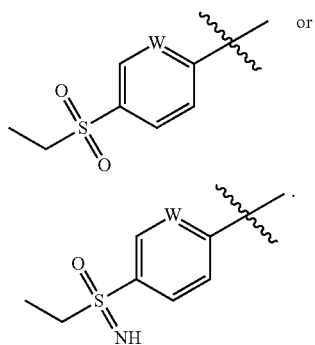

In some more typical embodiments,

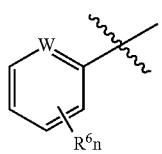

is selected from

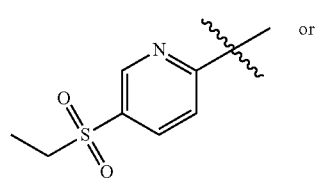

In some most typical embodiments,

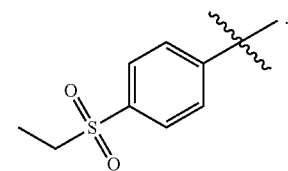

In some embodiments, the aforesaid compound of formula (I) has a structure represented by formula (I-A),

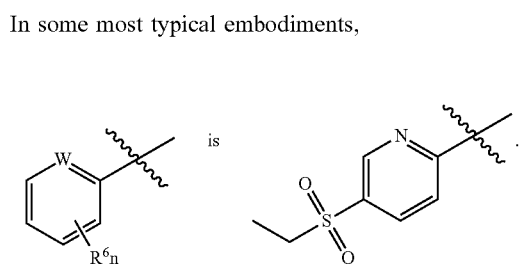

Formula I-A wherein U, W, X, Y, Z, $Cy^1$, $R^1$, $R^2$, $R^3$, $R^4$, $R^5$, and $R^6$ are as defined previously.

In some embodiments, the aforesaid compound of formula (I) has a structure represented by formula (I-A-1), Formula I-A-1

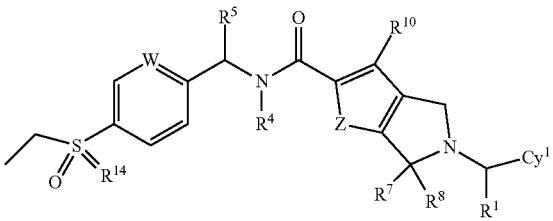

wherein W, Z, $Cy^1$, $R^1$, $R^4$, $R^5$, $R^7$, $R^8$, $R^{10}$, and $R^{14}$ are as defined in the aforesaid compound of formula (I).

In some embodiments, the aforesaid compound of formula (I) has a structure represented by formula (I-A-2), Formula I-A-2

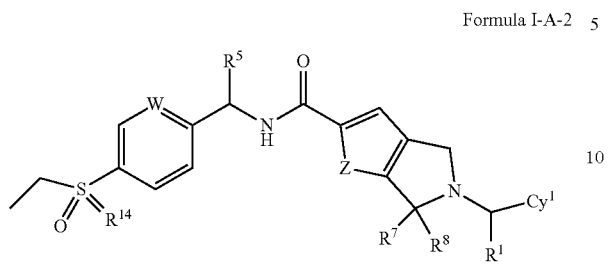

wherein W, Z, Cy$^1$, R$^1$, R$^5$, R$^7$, R$^8$, and R$^{14}$ are as defined in the aforesaid compound of formula (I).

In some embodiments, the aforesaid compound of formula (I) has a structure represented by formula (II), Formula II

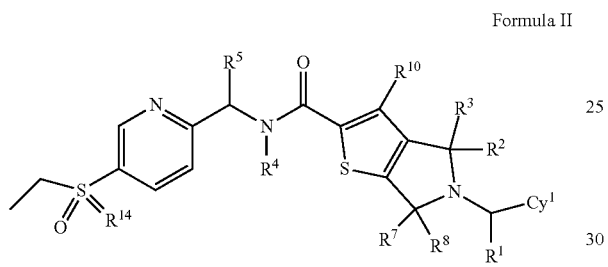

wherein Cy$^1$, R$^1$, R$^2$, R$^3$, R$^4$, R$^5$, R, R$^8$, R$^{10}$, and R$^{14}$ are as defined in the aforesaid compound of formula (I).

In some embodiments, the aforesaid compound of formula (I) has a structure represented by formula (III), Formula III

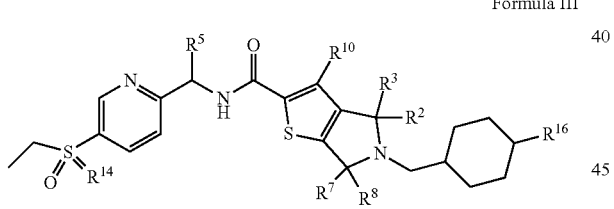

wherein R$^2$, R$^3$, R$^5$, R$^7$, R$^8$, R$^{10}$, R$^{14}$, and R$^{16}$ are as defined in the aforesaid compound of formula (I).

In some embodiments, the aforesaid compound of formula (I) has a structure represented by formula (IV), Formula IV

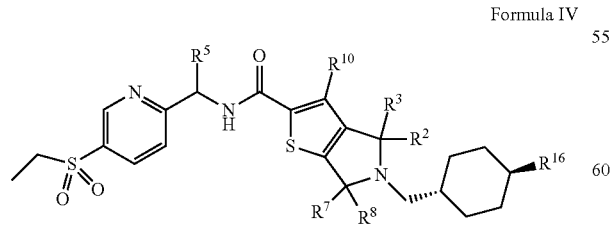

wherein R$^2$, R$^3$, R$^5$, R$^7$, R$^8$, R$^{10}$, and R$^{16}$ are as defined in the aforesaid compound of formula (I).

In some embodiments, the compound of formula (I) or a pharmaceutically acceptable salt thereof in the present application is selected from the following compounds or the pharmaceutically acceptable salts thereof:

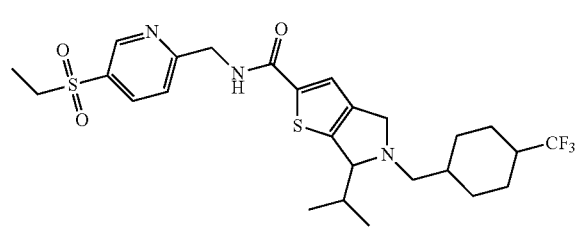

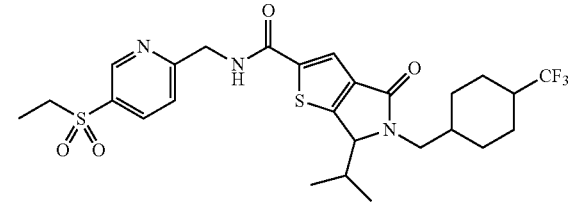

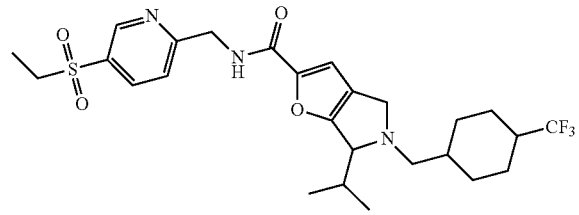

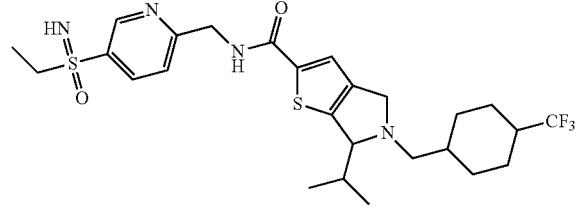

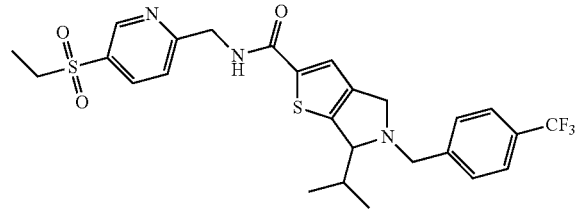

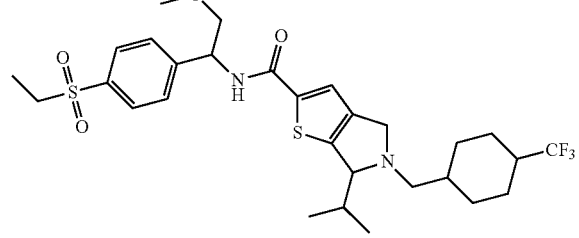

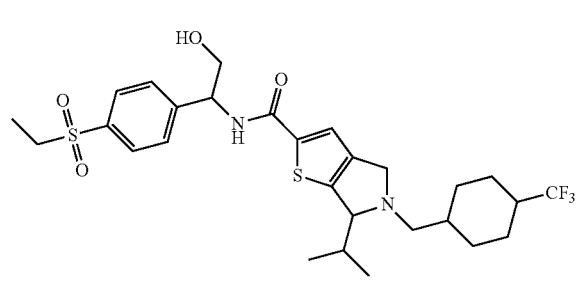

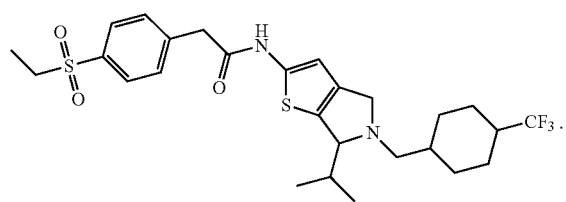 [SMILES: CCS(=O)(=O)c1ccc(CC(=O)Nc2cc3c(s2)C(C(C)C)N(CC2CCC(C(F)(F)F)CC2)C3)cc1]
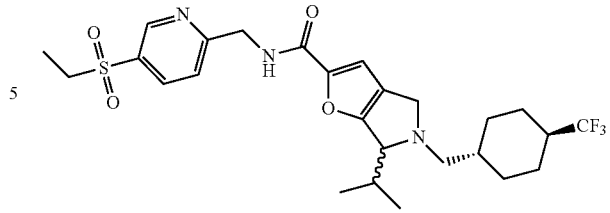
In some embodiments, the compound of formula (I) or a pharmaceutically acceptable salt thereof in the present application is selected from the following compounds or the pharmaceutically acceptable salts thereof:
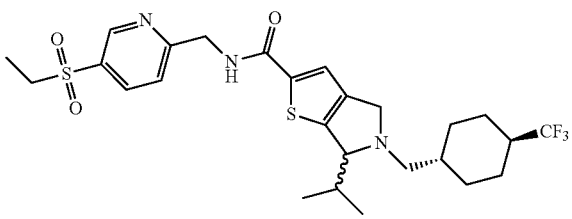
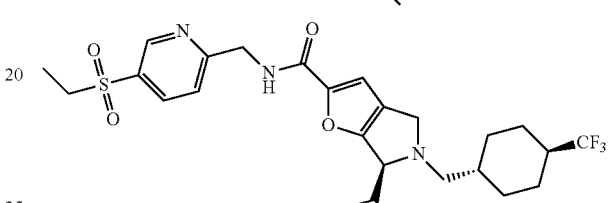
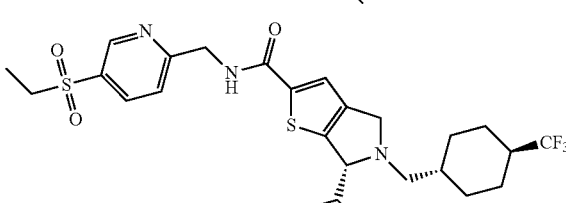
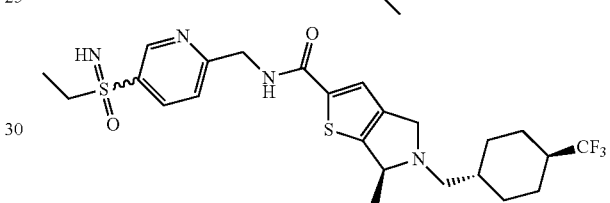
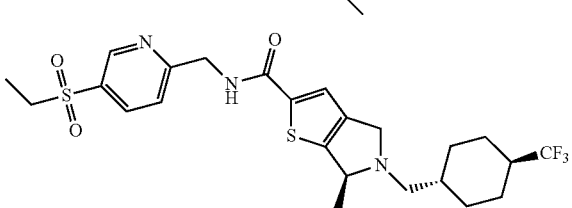
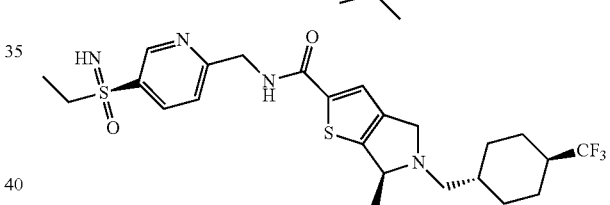
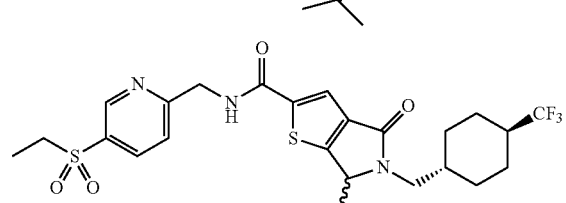
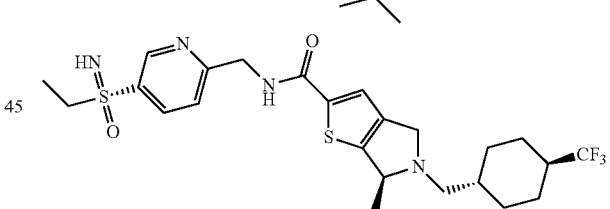
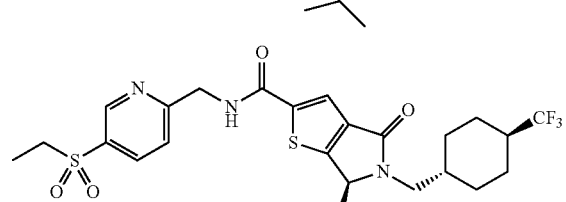
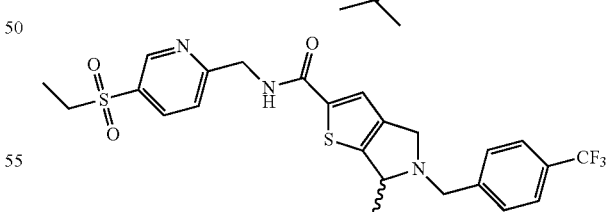
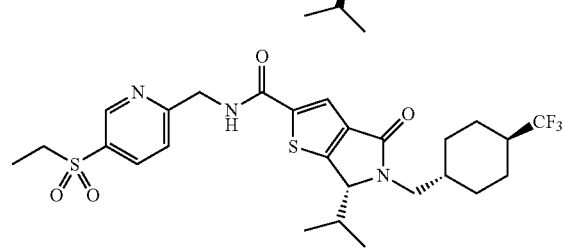
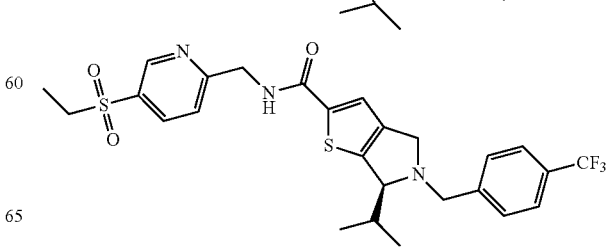

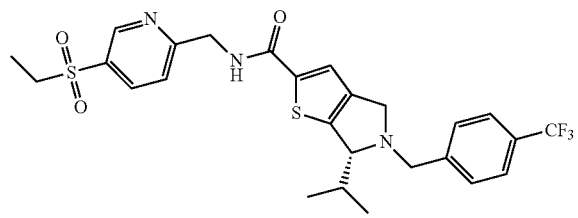
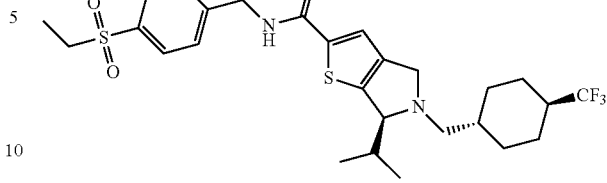
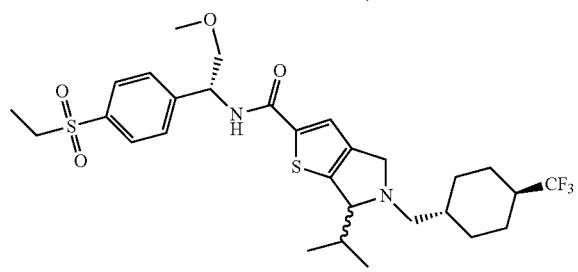
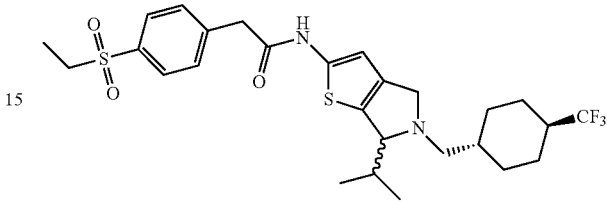
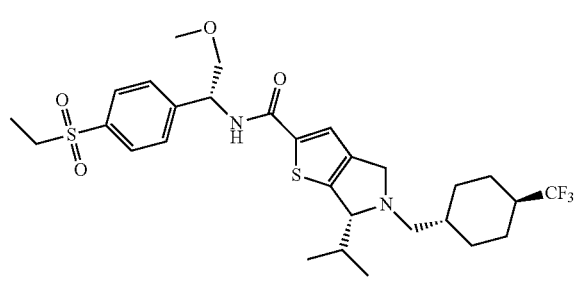
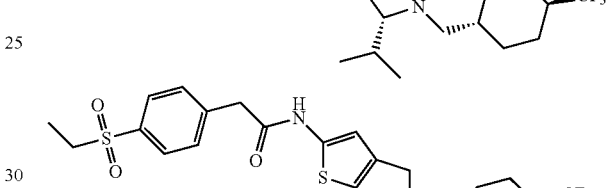
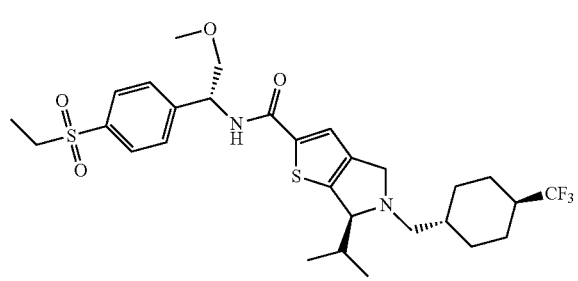
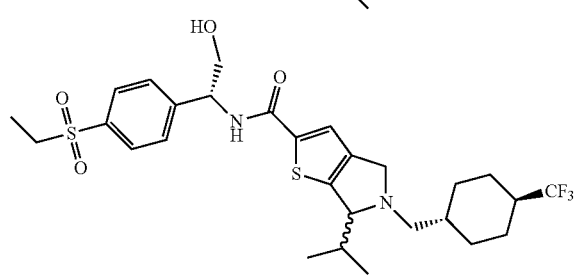
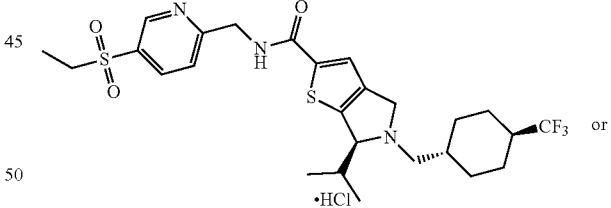
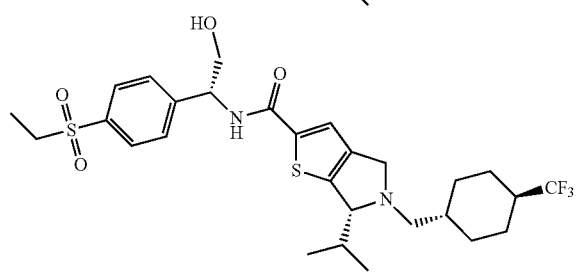

In some typical embodiments, the compound of formula (I) or the pharmaceutically acceptable salt thereof in the present application is the hydrochloride salt of the compound of formula (I). In some more typical embodiments, the compound of formula (I) or the pharmaceutically acceptable salt thereof in the present application is

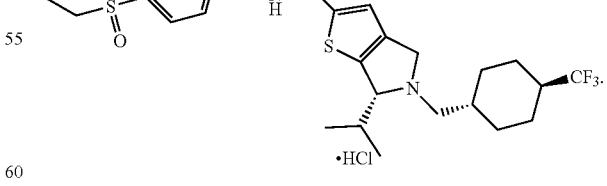

In another aspect, the present application relates to a pharmaceutical composition comprising the compound of formula (I) or a pharmaceutically acceptable salt thereof of the present application. In some embodiments, the pharmaceutical composition of the present application further comprises a pharmaceutically acceptable excipient.

The pharmaceutical composition of the present application may be prepared by combining the compound of the present application with an appropriate pharmaceutically acceptable excipient. For example, the pharmaceutical composition may be formulated into a solid, semi-solid, liquid or gaseous preparation, such as a tablet, a pill, a capsule, a powder, a granule, an ointment, an emulsion, a suspension, a suppository, an injection, an inhalant, a gel, a microsphere, and an aerosol.

Typical routes of administering the compound of the present application, or a pharmaceutically acceptable salt thereof, or a pharmaceutical composition thereof include, but are not limited to, oral, rectal, topical, inhalation, parenteral, sublingual, intravaginal, intranasal, intraocular, intraperitoneal, intramuscular, subcutaneous, and intravenous administration.

The pharmaceutical composition of the present application may be manufactured by the methods generally known in the art, e.g., a conventional mixing method, a dissolution method, a granulating method, a dragee-making method, a pulverization method, an emulsification method, a freeze-drying method, etc.

In some embodiments, the pharmaceutical composition is in an oral dosage form. As for oral administration, the pharmaceutical composition may be formulated by mixing an active compound with a pharmaceutically acceptable excipient well known in the art. These excipients enable the compounds of the present application to be formulated into a tablet, a pill, a lozenge, a dragee, a capsule, a liquid, a gel, a syrup, a suspension, and the like, which are used for oral administration to a patient.

A solid composition for oral administration may be prepared by a conventional mixing method, a filling method or a tabletting method. For example, the solid composition for oral administration may be obtained by the method as described below. In said method, the active compound is mixed with a solid excipient, the resulting mixture is grinded optionally, other suitable excipients are added if necessary, and then this mixture is processed into granules to obtain tablets or the cores of dragees. Suitable excipients include, but are not limited to, a binder, a diluent, a disintegrant, a lubricant, a glidant, a sweetener, a flavoring agent, and the like.

The pharmaceutical composition is also applicable to parenteral administration, for example, in a suitable unit dosage form of a sterile solution, a suspension or a lyophilized product.

In another aspect, the present application relates to a method for treating a RORγ receptor-mediated disease in a mammal, comprising administering the compound of formula (I), or a pharmaceutically acceptable salt thereof, or a pharmaceutical composition thereof in a therapeutically effective amount to a mammal, preferably human, in need thereof.

In some embodiments, in all of the methods for administering the compound of formula (I) of the present application, the daily dose is from 0.01 to 300 mg/kg body weight, preferably from 10 to 300 mg/kg body weight, and more preferably from 25 to 200 mg/kg body weight, in the form of a single dose or divided doses.

In another aspect, the present application relates to use of the compound of formula (I), or a pharmaceutically acceptable salt thereof, or a pharmaceutical composition thereof in the preparation of a medicament for preventing or treating a RORγ receptor-mediated disease in a mammal.

In another aspect, the present application relates to a compound of formula (I) or a pharmaceutically acceptable salt thereof for use in treating a RORγ receptor-mediated disease in a mammal.

In another aspect, the present application relates to a pharmaceutical composition for treating a RORγ receptor-mediated disease in a mammal, wherein the pharmaceutical composition comprises a compound of formula (I) or a pharmaceutically acceptable salt thereof.

Definitions

Unless otherwise specified, the following terms used herein have the following meanings. A specific term, if not particularly defined, should not be considered as uncertain or ambiguous, but should be understood as its ordinary meaning in the art. When a trade name appears herein, it is intended to refer to the corresponding commodity thereof or an active ingredient thereof.

The term "substituted" means that any one or more of the hydrogen atom(s) on a specific atom is substituted by a substituent, as long as the valence of the specific atom is normal and the substituted compound is stable. When a substituent is oxo (i.e., =O), it means that two hydrogen atoms are substituted, and oxo does not occur on an aromatic group.

The term "optional" or "optionally" means that the event or situation described later may or may not occur, and the description includes the case where the event or situation occurs and the case where the event or situation does not occur. For example, the case where an ethyl is "optionally" substituted by one or more fluorine or chlorine indicates that the ethyl may be unsubstituted ($CH_2CH_3$), mono-substituted (e.g. $CH_2CH_2F$, $CHClCH_3$), poly-substituted (e.g. $CHFCH_2F$, $CHClCHF_2$, $CH_2CHF_2$, etc.), or fully substituted ($CCl_2CF_3$, $CF_2CF_3$). It is understandable to a person skilled in the art that, for any group containing one or more substituents, no substitution or substitution pattern that is sterically impossible and/or cannot be synthesized is incorporated.

$C_{m-n}$ herein means that the number of the carbon atom(s) in this moiety is an integer in a given range. For example, "$C_{1-6}$" means that this group may have one carbon atom, two carbon atoms, three carbon atoms, four carbon atoms, five carbon atoms, or six carbon atoms.

When any variable (such as R) appears more than once in the composition or structure of a compound, its definition in each case is independent. Therefore, for example, if a group is substituted by two Rs, each R has an independent option.

The term "halo" or "halogen" refers to fluorine, chlorine, bromine, and iodine.

The term "hydroxyl" refers to the —OH group.

The term "cyano" refers to the —CN group.

The term "amino" refers to the —$NH_2$ group.

The term "nitro" refers to the —$NO_2$ group.

The term "hydroxyalkyl" refers to —$C_nH_{2n}OH$. For example, hydroxymethyl refers to —$CH_2OH$, and 2-hydroxyethyl refers to —$CH_2CH_2OH$.

The term "alkyl" refers to a hydrocarbon group represented by the general formula $C_nH_{2n+1}$. The alkyl may be linear or branched. For example, the term "$C_{1-6}$ alkyl" refers to an alkyl group containing 1 to 6 carbon atoms (e.g., methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moieties (i.e. alkyl) of alkoxy, alkylamino, dialkylamino, alkylsulfonyl, and alkylsulphanyl have the same meaning as described above.

The term "alkoxy" refers to —O-alkyl.

The term "alkylamino" refers to —NH-alkyl.

The term "dialkylamino" refers to —N(alkyl)$_2$.

The term "cycloalkyl" refers to a carbocyclic ring that is fully saturated and may exist as a monocyclic ring, a bridged ring or a spirocyclic ring. Unless otherwise indicated, the carbocyclic ring is usually a 3- to 10-membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl, and the like.

The term "aryl" refers to an aromatic cyclic group which is a full-carbon monocyclic ring or a fused polycyclic ring having a conjugated it-electron system. For example, an aryl may have 6 to 20 carbon atoms, 6 to 14 carbon atoms, or 6 to 12 carbon atoms. Non-limiting examples of aryl include, but are not limited to, phenyl, naphthyl, anthryl, 1,2,3,4-tetrahydronaphthalene, and the like.

The term "heteroaryl" refers to a monocyclic or fused polycyclic ring system, wherein at least one ring atom selected from N, O and S is contained, the remaining ring atoms are C, and at least one aromatic ring is contained. A preferred heteroaryl has a single 4- to 8-membered ring, especially a 5- to 8-membered ring, or a plurality of fused rings containing 6 to 14 ring atoms, especially 6 to 10 ring atoms. Non-limiting examples of heteroaryl include, but are not limited to, pyrrolyl, furyl, thienyl, thiazolyl, imidazolyl, oxazolyl, pyrazolyl, pyridyl, pyrimidinyl, pyrazinyl, quinolyl, isoquinolyl, tetrazolyl, triazolyl, triazinyl, benzofuryl, benzothienyl, indolyl, isoindolyl, etc.

The term "treating" means administering a compound or a drug formulation described in the present application to prevent, ameliorate or eliminate a disease or one or more symptoms associated with the disease, and includes:

(i) preventing a disease or a disease state from occurring in a mammal, especially when such mammal is susceptible to the disease state but has not yet been diagnosed as having the disease state;

(ii) inhibiting a disease or a disease state, i.e., restraining its development; and (iii) alleviating a disease or a disease state, i.e., causing the regression of the disease or the disease state.

The term "therapeutically effective amount" means the using amount of the compound of the present application for use in: (i) treating or preventing a specific disease, condition or disorder, (ii) alleviating, ameliorating or eliminating one or more symptoms of a specific disease, condition or disorder, or (iii) preventing or delaying the onset of one or more symptoms of a specific disease, condition or disorder described in the present application. The amount of the compound of the present application that constitutes a "therapeutically effective amount" varies depending on the compound, the disease state and its severity, the mode of administration, and the age of the mammal to be treated, but may be routinely determined by those skilled in the art according to their knowledge and the contents of the present application.

The term "pharmaceutically acceptable" is intended to refer to those compounds, materials, compositions and/or dosage forms which, within the scope of reliable medical judgment, are suitable for use in contact with the tissues of human beings and animals without excessive toxicity, irritation, allergic response, or other problems or complications, and commensurate with a reasonable benefit/risk ratio.

The term "pharmaceutically acceptable salt" includes, but is not limited to, an acid addition salt formed by a compound of formula (I) and an inorganic acid, an acid addition salt formed by a compound of formula (I) and an organic acid, or an addition salt formed by a compound of formula (I) and an acidic amino acid, and the like. The term "pharmaceutical composition" refers to a mixture comprised of one or more compounds of the present application or a salt thereof and a pharmaceutically acceptable excipient. The purpose of a pharmaceutical composition is to facilitate the administration of a compound of the present application to an organism.

The term "pharmaceutically acceptable excipient" refers to those excipients that have no significant irritating effect on an organism and do not impair the bioactivity and properties of the active compound. Suitable excipients are those well known to one skilled in the art, such as a carbohydrate, a wax, a water-soluble and/or water-swellable polymer, a hydrophilic or hydrophobic material, a gelatin, an oil, a solvent, water, and the like.

The word "comprise" and the variants thereof, such as "comprises" or "comprising", should be understood as an open and non-exclusive meaning, namely, "including but not limited to".

Unless otherwise specified, the abbreviations used in the present application have the following meanings.

EDCI: 1-ethyl-(3-dimethylaminopropyl)carbodiimide hydrochloride; HOBt: 1-hydroxybenzotriazole; TEA: triethylamine; TLC: thin-layer chromatography; PE: petroleum ether; EtOAc: ethyl acetate; MeOH: methanol; H$_2$SO$_4$: sulfuric acid; 1M: 1 mol/L; POCl$_3$: phosphorus oxychloride; DMF: N,N-dimethylformamide; ETOH: ethanol; NH$_3$—H$_2$O: aqueous ammonia; KOH: potassium hydroxide; THF: tetrahydrofuran; Boc$_2$O: di-tert-butyl dicarbonate; DEA: diethylamine; Pre-HPLC: preparative high performance liquid chromatography; SFC: supercritical fluid chromatography; LC-MS: liquid chromatography-mass spectrometry; MS: multiple sclerosis; EAE: experimental autoimmune encephalomyelitis; PLP: proteolipid protein; MBP: myelin basic protein; CFA: complete Freund's adjuvant; SPF: specific pathogen free; μl: microliter; PTX: pertussis toxin; MOG35-55: myelin oligodendrocyte glycoprotein; p.o.: oral administration; ip: intraperitoneal injection; ig: oral administration; topical: topical administration; IMQ: imiquimod; LDA: lithium diisopropylamide; HATU: 2-(7-oxybenzotriazol)-N,N,N',N'-tetramethyluronium hexafluorophosphate; DMAP: 4-dimethylaminopyridine; NB S: N-bromosuccinimide; Pd(dppf)Cl$_2$.CH$_2$Cl$_2$: 1,1'-bis(diphenylphosphino)ferrocene-palladium(II)dichloride dichloromethane complex; NaBH(OAc)$_3$: sodium triacetoxyborohydride; HCl/EtOAc: hydrochloric acid/ethyl acetate; DCE: 1,2-dichloroethane; LiOH.H$_2$O: lithium hydroxide monohydrate; DIPEA: N,N-diisopropylethylamine; HCl/dioxane: hydrochloric acid/dioxane; PPTs: pyridinium 4-methylbenzenesulfonate; MgSO$_4$: magnesium sulfate; BH$_3$-Me$_2$S: borane-dimethyl sulfide complex; CuI: cuprous iodide; K$_3$PO$_4$: potassium phosphate; SOCl$_2$: sulfoxide chloride; TR-FRET: time-resolved fluorescence resonance energy transfer; Tris: tris(hydroxymethyl)aminomethane; KCl: potassium chloride; Na-EDTA: sodium ethylene diamine tetracetate; BSA: bovine serum albumin; DTT: dithiothreitol; His: histidine; RORC2: human retinoic acid-related orphan receptor C, subtype 2; also referred to as truncated RORγ; RORC2-LBD: human retinoic acid-related orphan receptor C, subtype 2-ligand binding domain; mpk: referring to milligram per kilogram, i.e., mg/kg; QD: once a day; Bid: twice daily; n or N: number; FTY720: fingolimod hydrochloride; DMSO: dimethyl sulfoxide; PEG400: polyethylene glycol 400; DDH$_2$O: deionized water; PBS refers to phosphate buffered saline solution; Detachin refers to a cell detachment reagent; IFA: incomplete Freund's adjuvant.

In the present disclosure, the dose of a compound is calculated in terms of its free alkali form, unless otherwise specified.

In the present disclosure, a solvent control group and a vehicle control group have the same meaning, unless otherwise specified.

The intermediate(s) and the compound(s) of the present application may also exist in different tautomeric forms, and all of such forms are included within the scope of the present application. The term "tautomer" or "tautomeric form" refers to structural isomers with different energies, which are interconvertible via a low energy barrier. For example, a proton tautomer (also referred to as prototropic tautomer) includes interconversion via the migration of a proton, such as keto-enol isomerization and imine-enamine isomerization. A specific example of a proton tautomer is an imidazole moiety, wherein a proton may migrate between two cyclic nitrogen atoms. A valence tautomer includes interconversion via the recombination of some of the bonding electrons. An exemplary enol tautomer is as shown below, but is not limited thereto.

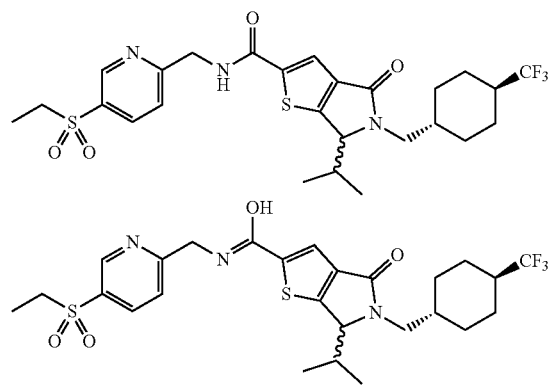

The present application further comprises the isotopically labeled compounds of the present application, wherein the compounds are as same as those described herein, but one or more atoms thereof are replaced with atom(s) having an atomic weight or mass number different from that normally found in nature. Examples of the isotopes that may be incorporated into the compounds of the present application include the isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I, and $^{36}$Cl.

Certain isotopically labeled compounds of the present application (such as those labeled with $^3$H and $^{14}$C) may be used in the tissue distribution analysis of a compound and/or a substrate. Tritiated isotope (i.e., $^3$H) and carbon-14 (i.e., $^{14}$C) isotope are particularly preferred due to their ease of preparation and detectability. Positron-emitting isotopes, such as $^{15}$O, $^{13}$N, $^{11}$C, and $^{18}$F, may be used in positron emission tomography (PET) studies to determine the occupancy of a substrate. Isotopically labeled compounds of the present application are generally prepared by replacing a reagent unlabeled by an isotope with an isotopically labeled reagent via the following procedures similar to those disclosed in the embodiments and/or Examples below.

In addition, replacement with a heavier isotope such as deuterium (i.e., $^2$H) may provide certain therapeutic advantages (e.g., a prolonged half-life in vivo or a reduced demand of dose) resulting from higher metabolic stability, and thus being possibly preferred in certain cases, wherein the deuterium substitution may be partial or complete, and a partial deuterium substitution means that at least one hydrogen is substituted by at least one deuterium. Exemplary deuterated compounds are as shown below, but are not limited thereto.

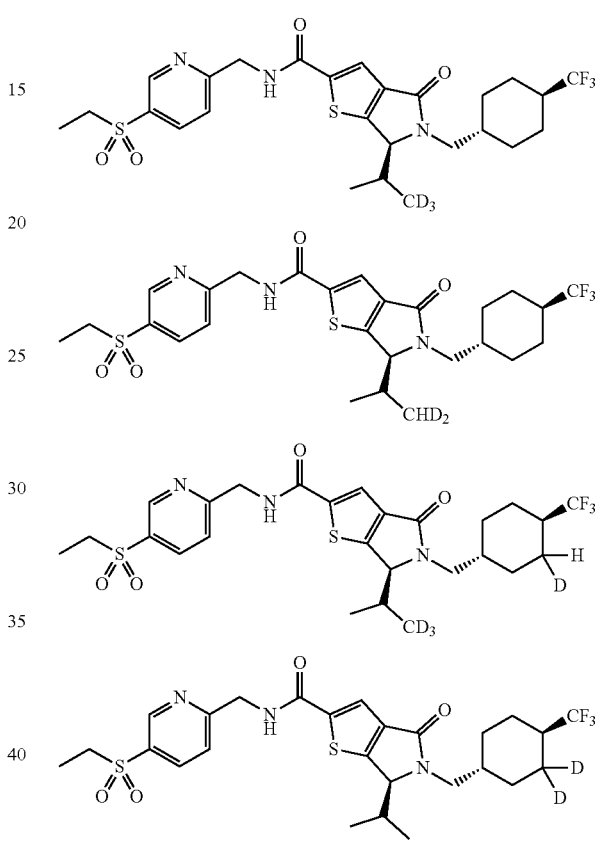

The compounds of the present application may be asymmetric, for example, having one or more stereoisomers. Unless otherwise specified, all stereoisomers, e.g., enantiomers and diastereoisomers, are included. The compound(s) containing an asymmetric carbon atom of the present application may be isolated in an optically active pure form or in a racemic form. An optically active pure form may be resolved from a racemic mixture or synthesized using a chiral starting material or a chiral reagent. Non-limiting examples of the stereoisomer include, but are not limited to:

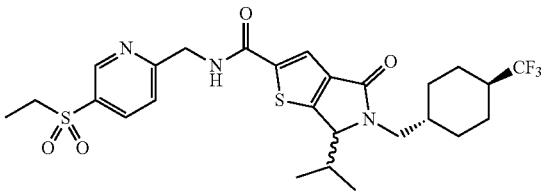

-continued

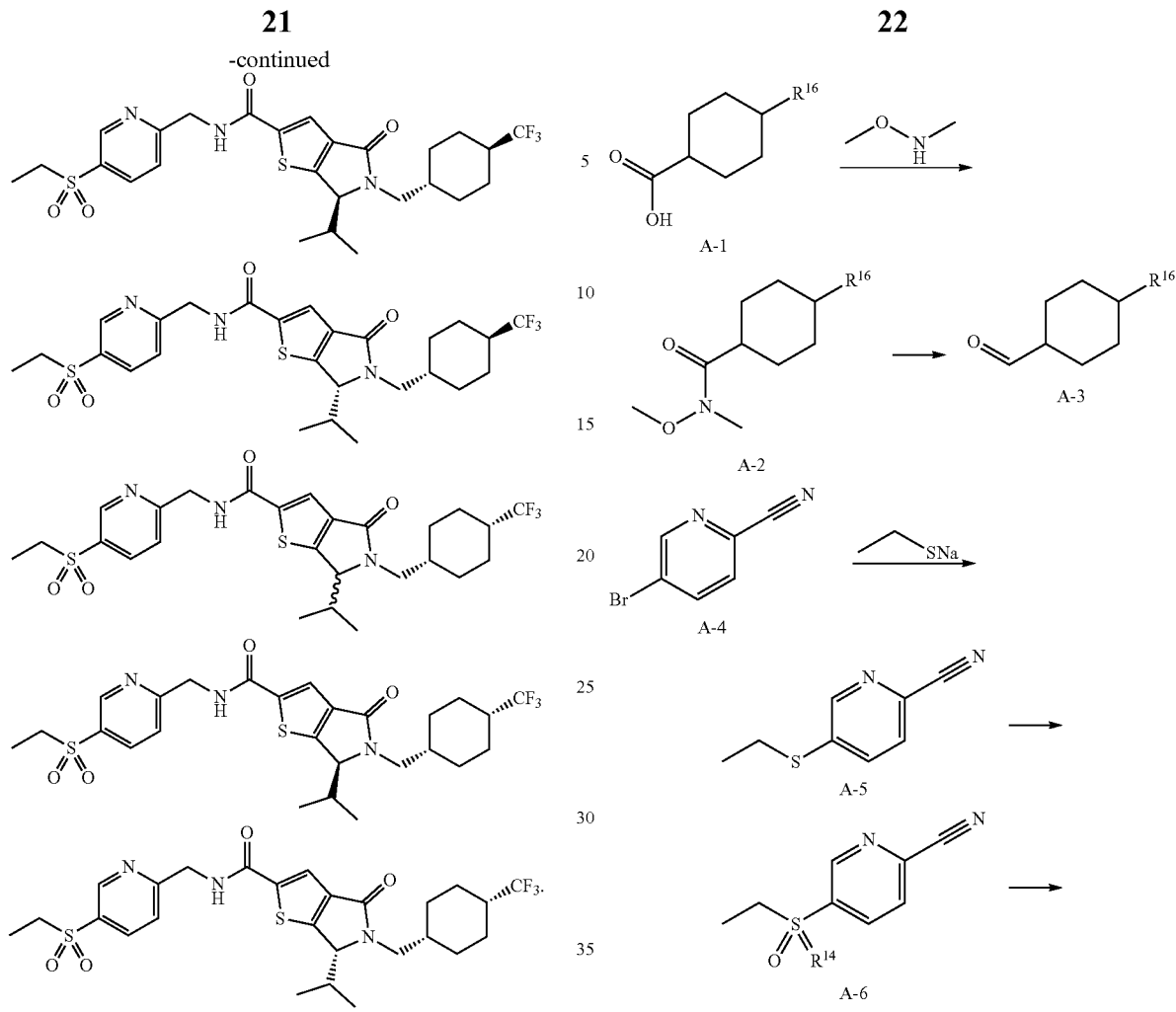

The compounds of the present application may be prepared by a variety of synthesis methods well known to a person skilled in the art, including the specific embodiments listed below, the embodiments formed by combining said specific embodiments with other chemical synthesis methods, and the equivalent alternatives well known to a person skilled in the art. Preferred embodiments include, but are not limited to, the Examples of the present application.

The chemical reactions of the specific embodiments of the present application are completed in a suitable solvent, and the solvent must be suitable for the chemical change(s) of the present application as well as the reagents and materials required for the same. In order to obtain the compounds of the present application, a person skilled in the art sometimes needs to modify or select synthesis steps or reaction schemes based on the existing embodiments.

An important consideration in the planning of a synthetic route in this field is selecting a suitable protecting group for the reactive functional group (such as the amino group in the present application). For example, refer to "Greene's Protective Groups in Organic Synthesis (4$^{th}$ Ed)", Hoboken, N.J.: John Wiley & Sons, Inc. All references cited in the present application are incorporated herein in their entirety.

In some embodiments of the present application, the compound of formula (III) is prepared and obtained via the synthetic route as shown below:

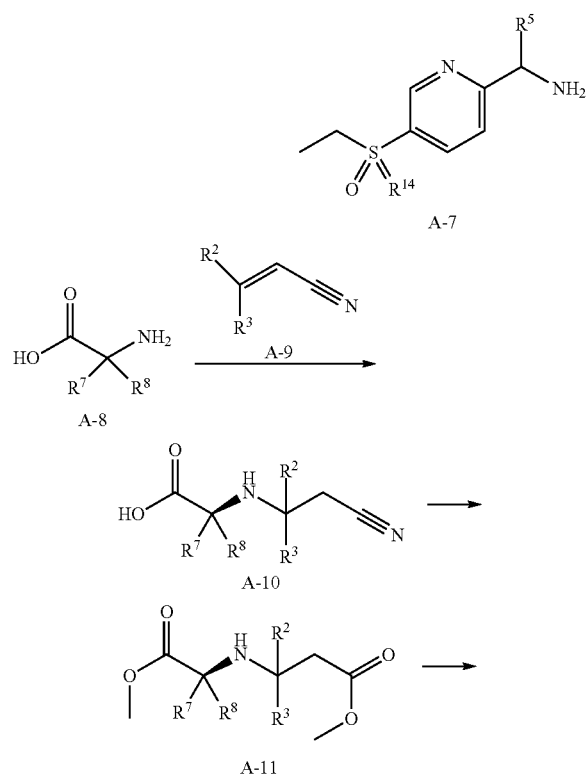

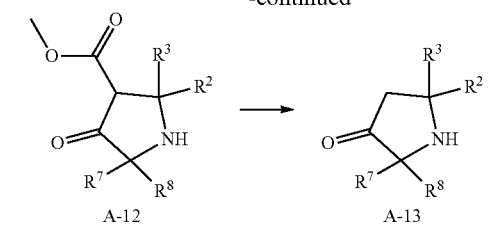
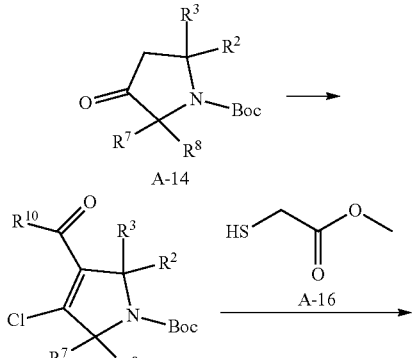
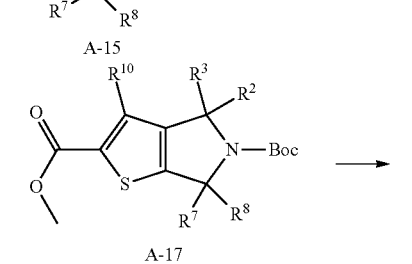
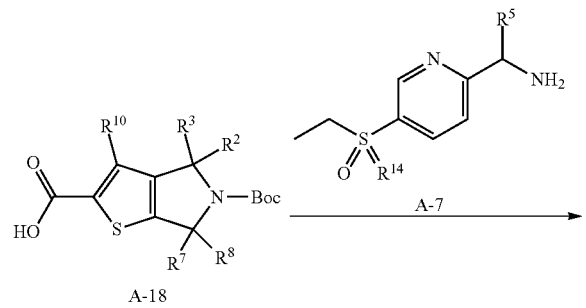
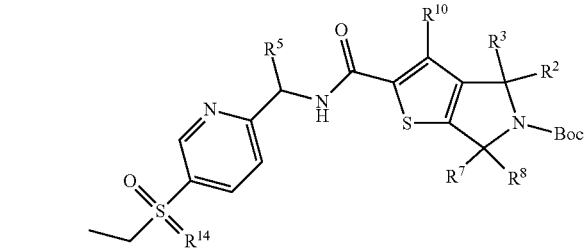
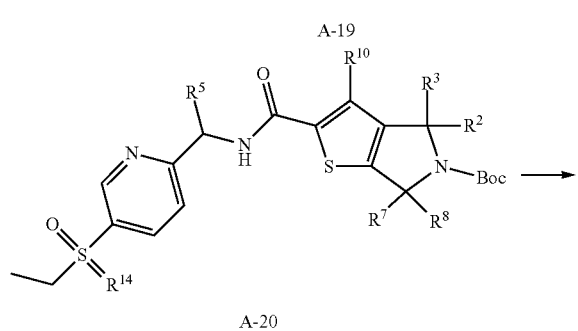
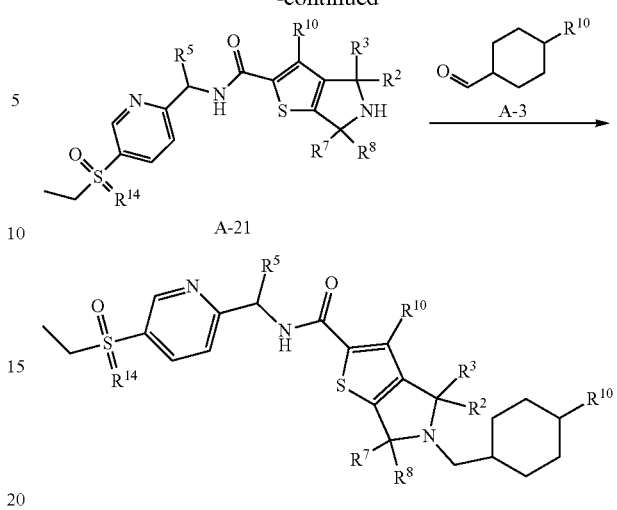
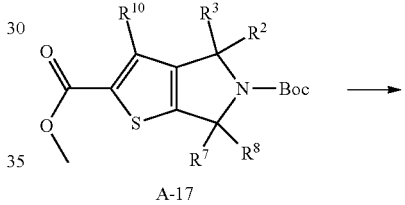
wherein $R^2$, $R^3$, $R^5$, $R^7$, $R^8$, $R^{10}$, $R^{14}$, and $R^{16}$ are defined as those of the compound of formula (III).
In some other embodiments of the present application, the compound of formula (III) is prepared and obtained via the synthetic route as shown below:
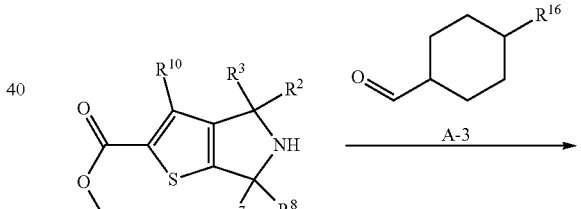
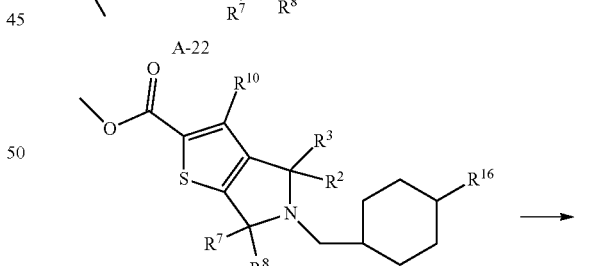
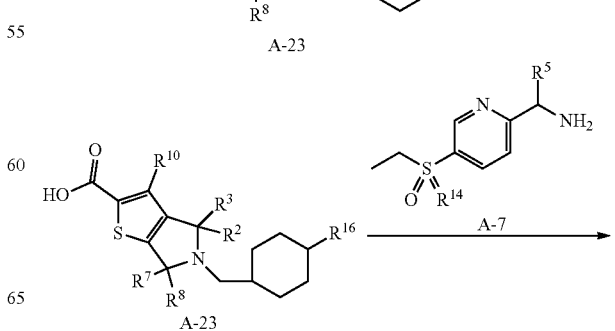

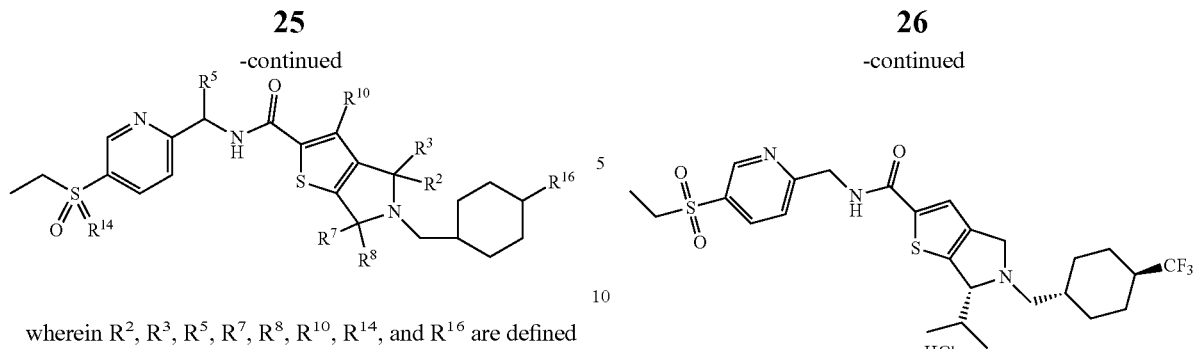

wherein $R^2$, $R^3$, $R^5$, $R^7$, $R^8$, $R^{10}$, $R^{14}$, and $R^{16}$ are defined as those of the compound of formula (III).

DETAILED DESCRIPTION

Figure 1:
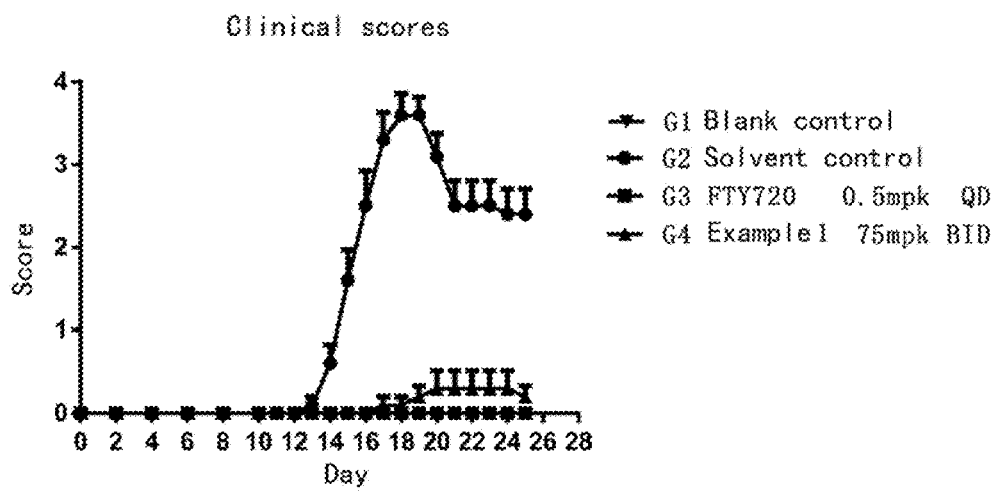
FIG. 1 shows the results of clinical scores of the in vivo pharmacodynamic research on MOG35-55-induced experimental autoimmune encephalomyelitis (EAE) in mice.

The present disclosure is described in detail below by Examples, but it does not imply any disadvantageous limitation on the present disclosure. The present disclosure has been described in detail herein, and its specific embodiments are also disclosed therein. Various changes and improvements made to the specific embodiments of the present disclosure will be apparent to a person skilled in the art without departing from the spirit and scope of the present disclosure.

Example 1 and Example 2

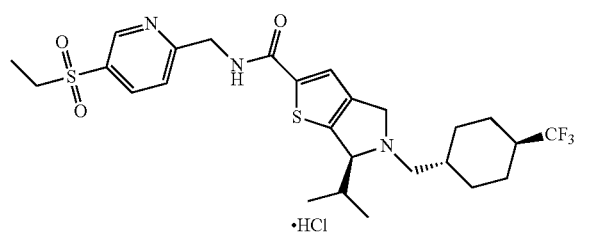

Example 1 or Example 2

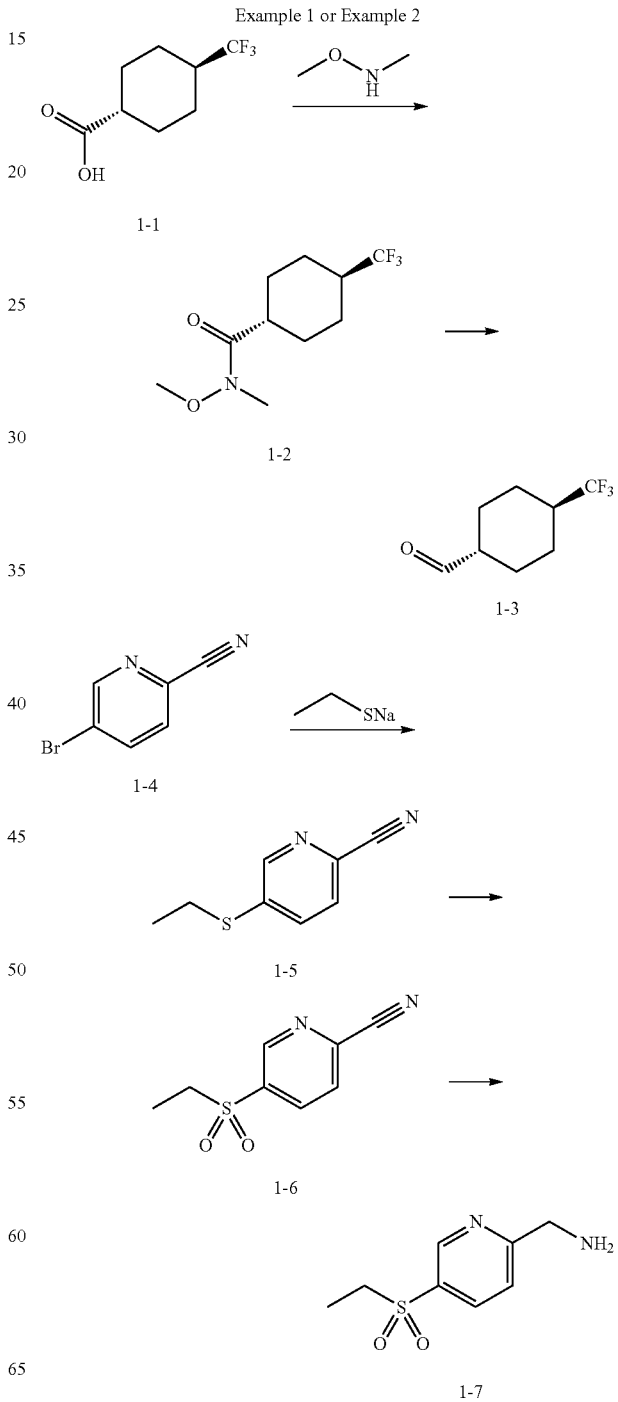

27
-continued
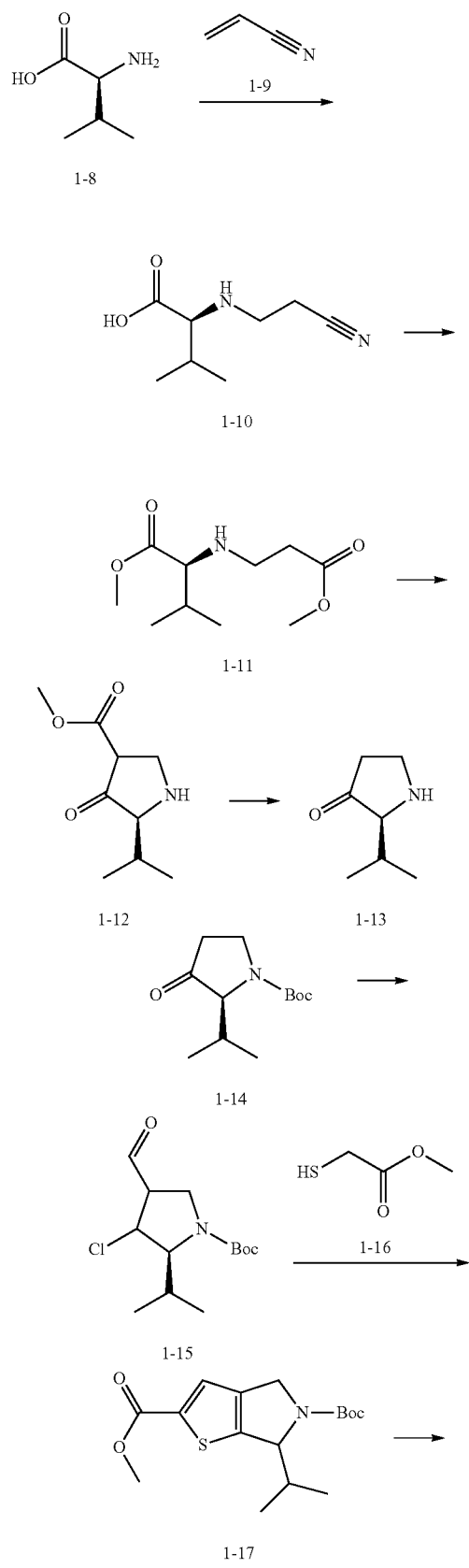
28
-continued
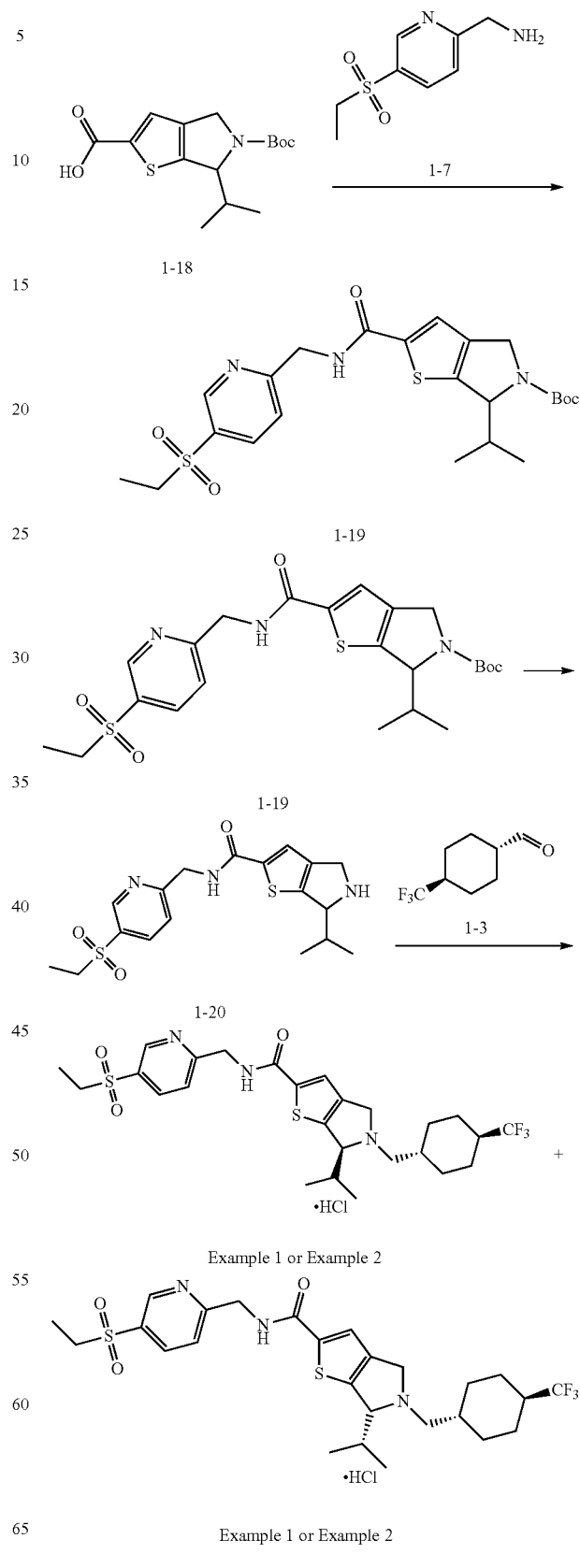

Synthesis of Compound 1-2

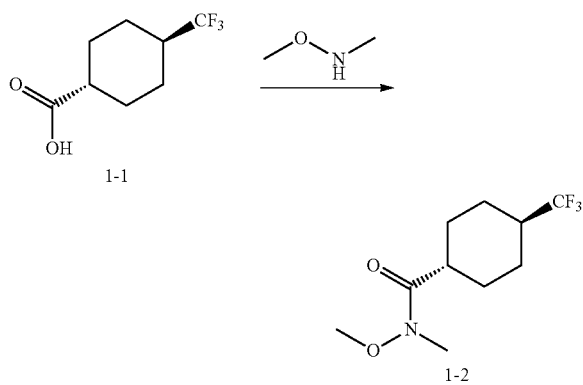

To a solution of Compound 1-1 (25 g) and N-methoxymethylamine hydrochloride (14.9 g) in 500 mL dichloromethane, TEA (51.6 g, 71.0 mL), EDCI (36.7 g) and HOBt (25.8 g) were added. The reaction solution was reacted at 10 to 20° C. for 16 hours. TLC (PE:EtOAc=1:1) showed the completion of the reaction. The reaction solution was dispersed in 500 mL dichloromethane and 500 mL water. The resultant was subjected to liquid-liquid separation. The organic phase was washed once with 500 mL saturated brine, dried over anhydrous sodium sulfate and filtered, and the filtrate was concentrated to obtain a crude product. The crude product was allowed to pass through a flash column (SepaFlash® silica gel flash column (220 g), eluent: ethyl acetate/petroleum ether; elution gradient: ethyl acetate/petroleum ether (V/V)=0% to 100%; flow rate: 100 mL/min) and Compound 1-2 was obtained after the purification.

$^1$H NMR (400 MHz, CHLOROFORM-d): δ 3.71 (s, 3H), 3.19 (s, 3H), 2.62-2.74 (m, 1H), 1.99-2.07 (m, 3H), 1.92 (br d, J=13.6 Hz, 2H), 1.48-1.61 (m, 2H), 1.32-1.44 (m, 2H);

$^{19}$F NMR (400 MHz, CHLOROFORM-d): δ=−73.8.

Synthesis of Compound 1-3

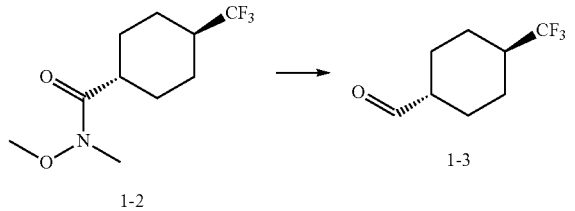 [SMILES: CON(C)C(=O)[C@H]1CC[C@H](C(F)(F)F)CC1 ; O=C[C@H]1CC[C@H](C(F)(F)F)CC1]

At −65° C., a solution of Compound 1-2 (10 g) in 50 mL tetrahydrofuran was added dropwise to a suspension of lithium aluminum hydride (1.90 g) in 50 mL tetrahydrofuran. After the completion of the dropwise addition, the reaction solution was reacted at −70 to −65° C. for 4 hours. TLC (PE:EtOAc=5:1) showed that Compound 1-2 was reacted completely. The reaction was quenched with methanol (6.43 g) at −65° C. When the reaction mixture was heated to −10° C., 1 M citric acid aqueous solution was added dropwise, the pH was adjusted to approximately 4, and the temperature was controlled at −10 to −5° C. during this process. The resulting mixture was extracted with ethyl acetate (300 mL×3). The organic phases were combined, washed with 300 mL saturated brine, dried over anhydrous sodium sulfate and filtered, and the filtrate was concentrated to obtain crude Compound 1-3, which was used directly in the next step without further purification.

$^1$HNMR (400 MHz, CHLOROFORM-d): δ 9.65 (s, 1H), 2.09-2.16 (m, 1H), 2.03-2.05 (m, 4H), 1.92-1.99 (m 1H), 1.23-1.32 (m, 4H).

Synthesis of Compound 1-5

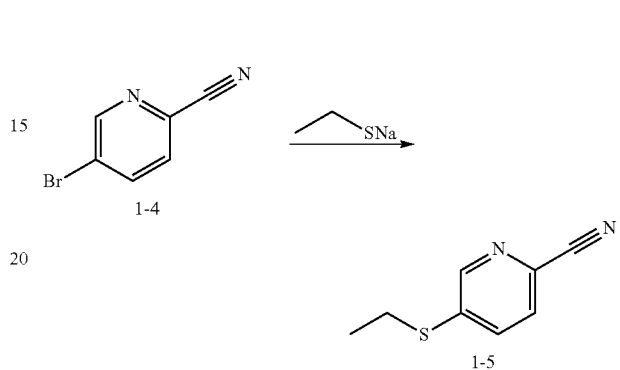

Compound 1-4 (50.0 g) was dissolved in N-methylpyrrolidone (500 mL), potassium carbonate (49.1 g) and sodium ethylthiolate (31.0 g) were added to the reaction solution, and the mixture was then stirred at 20° C. for 12 hours. TLC (PE:EtOAc=5:1) showed the disappearance of the starting materials. The reaction solution was poured into 1500 mL water, and a solid precipitated. The solid was filtered, and the filter cake was dried under vacuum to obtain Compound 1-5.

MS: m/z 165.1 [M+H]$^+$.

Synthesis of Compound 1-6

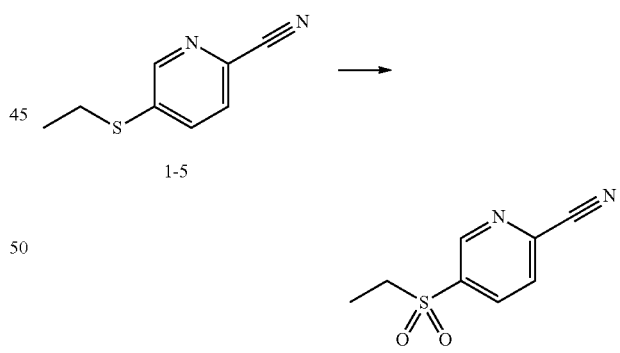

Compound 1-5 (58.0 g) was dissolved in methanol (600 mL), and a suspension of potassium peroxymonosulfate (434.2 g) in 900 mL water was added dropwise to the reaction solution at 0° C. Thereafter, the reaction solution was stirred at 0 to 20° C. for 16 hours. TLC (PE/EtOAc=3:1) showed that the starting materials were reacted completely. The reaction solution was filtered, and the excess potassium peroxymonosulfate in the reaction solution was quenched with sodium thiosulfate. After methanol was removed under reduced pressure, the resulting mixture was extracted with ethyl acetate (500 mL×2). The organic phases were combined, washed with saturated brine (300 mL), dried over anhydrous sodium sulfate and filtered, and the filtrate was concentrated under reduced pressure to obtain a crude product of Compound 1-6. The crude product was purified by column chromatography (silica, 100 to 200 mesh silica gel, eluent: petroleum ether/ethyl acetate; elution gradient: petroleum ether:ethyl acetate (V:V)=10:1 to 2:1), thereby obtaining Compound 1-6.

MS: m/z 197.0 [M+H]$^+$;

$^1$H NMR (400 MHz, CDCl$_3$-d): δ 9.13 (d, J=1.6 Hz, 1H), 8.38 (dd, J=8.4, 2.4 Hz, 1H), 7.94 (d, J=8.4 Hz, 1H), 3.21 (Q, J=7.2 Hz, 2H), 1.35 (d, J=7.6 Hz, 3H).

Synthesis of Compound 1-7

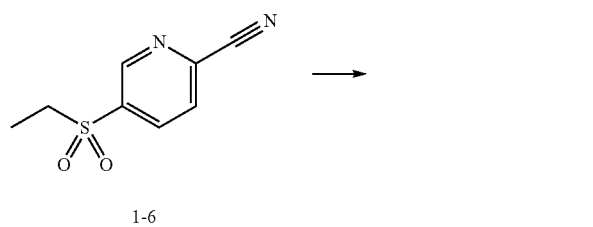

Compound 1-6 (10 g) was dissolved in anhydrous methanol (100.00 mL), and dry palladium on carbon (10%) was added under nitrogen protection. The mixture was purged with nitrogen gas for 3 times, and then purged with hydrogen gas for 3 times. The reaction solution was stirred at 25° C. for 3 hours in an atmosphere of H$_2$ (50 Psi). When LC-MS showed the completion of the reaction, the reaction solution was filtered through celite, and the filtrate was concentrated under reduced pressure to obtain Compound 1-17.

MS: m/z 201.0 [M+H]$^+$;

$^1$H NMR (400 MHz, CDCl$_3$): δ 9.04 (d, J=2.0 Hz, 1H), 8.15 (dd, J=2.4, 8.4 Hz, 1H), 7.56 (d, J=8.4 Hz, 1H), 4.12 (s, 2H), 3.16 (q, J=7.6 Hz, 2H), 1.32 (t, J=7.6 Hz, 3H).

Synthesis of Compound 1-10

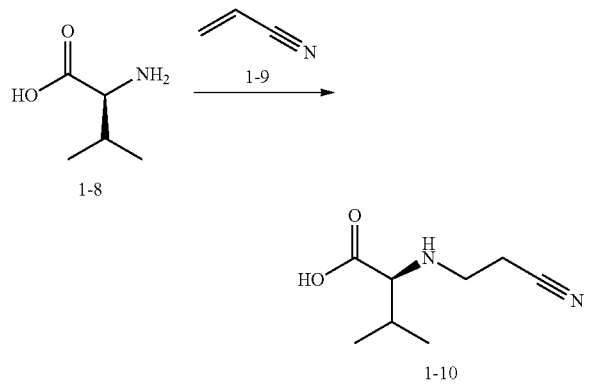

At 20° C., an aqueous solution (188 mL) of KOH (105.93 g, purity: 85%) was added to a suspension of Compound 1-8 (188 g) in water (188 mL). The resultant was stirred at 20° C. until Compound 1-8 was completely dissolved. The solution was cooled to 0 to 5° C., Compound 1-9 (91.2 g, 114.00 mL) was added dropwise under nitrogen protection, and the temperature was kept constant. After the dropwise addition was complete, the reaction solution was stirred at 0 to 5° C. for 3 hours. After the completion of the reaction was monitored by LC-MS, water (470 mL) was added to the reaction solution, and the pH of the resultant was adjusted to approximately 5 with concentrated hydrochloric acid (approx. 130 mL). A large amount of solid was generated, and as a result, a suspension was produced. The suspension was stirred continuously at 0 to 5° C. for 1 hour. A solid was obtained by filtration and washed with water (47 mL). The solid was collected and dried under vacuum at 60° C. to obtain Compound 1-10.

MS: m/z 170.9 [M+H]$^+$;

$^1$H NMR (400 MHz, DEUTERIUM OXIDE): δ 3.46 (d, J=4.0 Hz, 1H), 3.32 (br t, J=6.8 Hz, 2H), 2.92 (br t, J=6.8 Hz, 2H), 2.05-2.26 (m, 1H), 0.94 (br dd, J=6.8, 17.6 Hz, 6H).

Synthesis of Compound 1-11

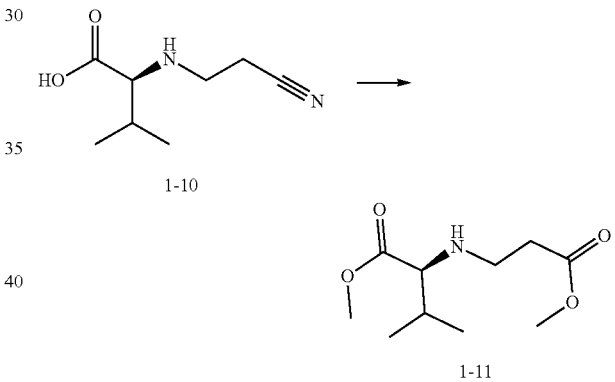

Compound 1-10 (94 g) was added to a prepared solution of absolute ethanol (450 mL) in concentrated H$_2$SO$_4$ (150 mL). Under the protection of nitrogen, the reaction solution was stirred at 90° C. for 16 hours. After the completion of the reaction was monitored by LC-MS, the reaction solution was poured into a saturated sodium bicarbonate solution until pH was approximately 8, and the mixture was extracted three times with 300 mL dichloromethane (100 mL×3). The organic phases were combined and washed with 100 mL (100 mL×1) of saturated saline. The organic phases were dried over anhydrous sodium sulfate, filtered, and concentrated to obtain a crude product of Compound 1-11. The crude product was directly used in the next step without further purification.

MS: m/z 186.0 [M+H]$^+$;

$^1$H NMR (400 MHz, CHLOROFORM-d): δ 3.74 (s, 3H), 3.70 (s, 3H), 2.90-3.01 (m, 2H), 2.58-2.74 (m, 2H), 2.48-2.52 (m, 2H), 1.91 (qd, J=6.8, 13.2 Hz, 1H), 0.94 (dd, J=2.0, 6.8 Hz, 6H).

Synthesis of Compound 1-12

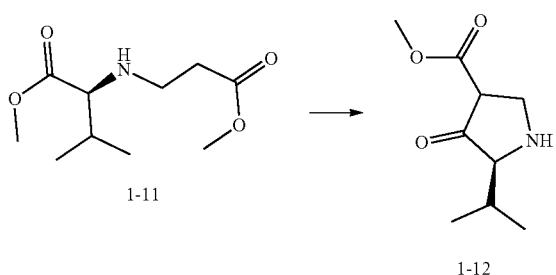

To a solution of Compound 1-11 (96.0 g) in tetrahydrofuran (50 mL) was added a 1 M solution of potassium tert-butoxide in tetrahydrofuran (645 mL). Under the protection of nitrogen, the reaction solution was stirred at 20° C. for 20 minutes. After the completion of the reaction was monitored by LC-MS, the reaction solution was concentrated to dryness to obtain a crude product of Compound 1-12. The crude product was directly used in the next step without further purification.

MS: m/z 186.0 [M+H]$^+$.

Synthesis of Compound 1-13

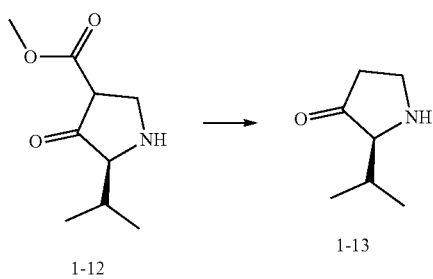

To a solution of Compound 1-12 (80.0 g) in ethanol (640 mL) was added concentrated hydrochloric acid (640 mL). Under the protection of nitrogen, the reaction solution was stirred at 90° C. for 0.5 hours. After the completion of the reaction was monitored by LC-MS, the reaction solution was concentrated to dryness to obtain the hydrochloride of Compound 1-13 as a crude product. The crude product was directly used in the next step without further purification.

MS: m/z 127.9 [M+H]$^+$.

Synthesis of Compound 1-14

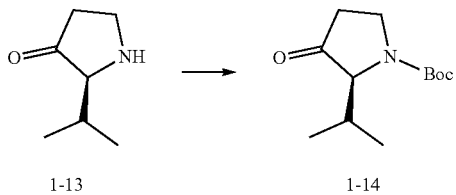

To a solution of the hydrochloride of Compound 1-13 (70.0 g) in dichloromethane (500 mL), triethylamine (129.8 g, 178.62 mL) and Boc$_2$O (112.0 g, 117.92 mL) were added. Under the protection of nitrogen, the reaction solution was stirred at 20° C. for 2 hours. After the completion of the reaction was monitored by LC-MS, water (300 mL) was added to the reaction solution, and the mixture was extracted three times with 900 mL (300 mL×3) of dichloromethane. The combined organic phases were washed with 200 mL (200 mL×1) of saturated brine. The organic phase was dried over anhydrous sodium sulfate, filtered, and concentrated. The crude product was purified by using a flash purification system (SepaFlash® silica gel flash column (330 g), eluent: petroleum ether/ethyl acetate; elution gradient: petroleum ether/ethyl acetate (V/V)=0% to 30%; flow rate: 100 mL/min) to obtain Compound 1-14.

MS: m/z 171.9 [M−56+H]$^+$;

$^1$H NMR (400 MHz, CHLOROFORM-d): δ 3.93-4.10 (m, 1H), 3.75-3.87 (m, 1H), 3.56 (br d, J=8.8 Hz, 1H), 2.52-2.66 (m, 1H), 2.40-2.51 (m, 1H), 2.16-2.38 (m, 1H), 1.50 (s, 9H), 1.02 (d, J=6.8 Hz, 3H), 0.96 (d, J=6.8 Hz, 3H).

Synthesis of Compound 1-15

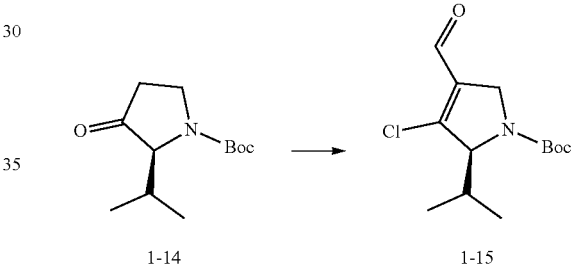

POCl$_3$ (3.96 g, 2.40 mL) was added dropwise to DMF (14.3 g, 15.00 mL) at 0° C., and the reaction solution was stirred at 25° C. for 0.5 hours. Then, a solution of Compound 1-14 (3 g) in DMF (30 mL) was added dropwise to the reaction solution, and the reaction solution was stirred at 25° C. for 3.5 hours. After the completion of the reaction was monitored by LC-MS, eight parallel reactions were combined, ice and a saturated aqueous sodium acetate solution (800 mL) were added to the reaction solution at 0° C., and the reaction solution was stirred at 0° C. for 1 hour. The reaction solution was extracted three times with ethyl acetate (500 mL). The combined organic phases were washed once with saturated brine (500 mL), and the organic phase was dried over anhydrous sodium sulfate, filtered, and concentrated. The crude product was purified by using a flash purification system (SepaFlash® silica gel flash column (80 g), eluent: petroleum ether/ethyl acetate; elution gradient: petroleum ether/ethyl acetate (V/V)=0% to 30%; flow rate: 60 mL/min) to obtain Compound 1-15 as the target compound.

MS (ESI) m/z: 217.8 [M−56+H]$^+$;

$^1$H NMR (400 MHz, CHLOROFORM-d): δ 9.93-10.04 (m, 1H), 4.62-4.83 (m, 1H), 4.37-4.59 (m, 1H), 4.04-4.16 (m, 1H), 2.25-2.48 (m, 1H), 1.49 (s, 9H), 1.02 (br s, 6H).

Synthesis of Compound 1-17

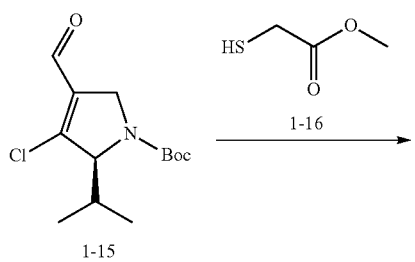

Triethylamine (10.54 g, 14.50 mL) was added to a solution of Compound 1-15 (14.5 g) and Compound 1-16 (7.02 g, 6 mL) in dichloromethane (100 mL). The reaction solution was stirred at 25° C. for 9 hours, and then the reaction solution was stirred at 50° C. for 3 hours. After the completion of the reaction was monitored by LC-MS, the reaction solution was concentrated, 100 mL water was added to dilute the residue, and the aqueous phase was extracted three times with ethyl acetate (100 mL×3). The combined organic phases were washed once with saturated brine (100 mL), and the organic phase was dried over anhydrous sodium sulfate, filtered, and concentrated. The crude product was purified by using a flash purification system (SepaFlash® silica gel flash column (80 g), eluent: petroleum ether/ethyl acetate; elution gradient: petroleum ether/ethyl acetate (V/V)=0% to 30%; flow rate: 60 mL/min) to obtain Compound 1-17.

MS (ESI) m/z: 269.9 [M−56+H]$^+$;

$^1$H NMR (400 MHz, CHLOROFORM-d): btain Compo J=14.8 Hz, 1H), 4.85-4.99 (m, 1H), 4.44-4.61 (m, 1H), 4.29-4.37 (m, 1H), 3.81 (s, 3H), 2.29-2.60 (m, 1H), 1.44 (s, 9H), 0.99 (t, J=7.2 Hz, 3H), 0.55 (t, J=7.2, 8.4 Hz, 3H).

Synthesis of Compound 1-18

To a solution of Compound 1-17 (13 g) in methanol (100 mL) was added a solution of sodium hydroxide (2.3 g) in water (10 mL), and the reaction solution was stirred at 50° C. for 45 minutes. After the completion of the reaction was monitored by LC-MS, the reaction solution was directly concentrated and dried by rotary evaporation to obtain a sodium salt of Compound 1-18 as a crude product. The crude product was directly used in the next step without further purification.

MS (ESI) m/z: 256 [M−56+H]$^+$.

Synthesis of Compound 1-19

To a suspension of the sodium salt of Compound 1-18 (25 g) and Compound 1-7 (9 g) in dichloromethane (100 mL), triethylamine (10.91 g, 15 mL), EDCI (10 g), and HOBt (10 g) were added. The reaction solution was stirred at 25° C. for 16 hours, and then the reaction solution was stirred at 50° C. for 3 hours. After the completion of the reaction was monitored by thin-layer chromatography and LC-MS, the reaction solution was concentrated, 150 mL water was added to dilute the residue, and the aqueous phase was extracted three times with ethyl acetate (100 mL×3). The combined organic phases were washed once with saturated brine (100 mL), and the organic phase was dried over anhydrous sodium sulfate, filtered, and concentrated. The crude product was purified by using a flash purification system (SepaFlash® silica gel flash column (40 g), eluent: petroleum ether/ethyl acetate; elution gradient: petroleum ether:ethyl acetate (V/V)=0% to 80%; flow rate: 40 mL/min) to obtain Compound 1-19.

MS (ESI) m/z: 494.2 [M+H]$^+$;

$^1$H NMR (400 MHz, CHLOROFORM-d): δ 8.99 (d, J=2.00 Hz, 1H), 8.11 (dd, J=2.2, 8.2 Hz, 1H), 7.48 (d, J=8.4 Hz, 1H), 7.32 (d, J=9.60 Hz, 1H), 4.86-5.00 (m, 1H), 4.77 (d, J=4.0 Hz, 2H), 4.53-4.65 (m, 1H), 4.34 (dd, J=4.0, 13.80 Hz, 1H), 3.06-3.13 (m, 3H), 2.34-2.56 (m, 1H), 1.44 (s, 9H), 1.24-1.28 (m, 3H), 1.00 (t, J=7.04 Hz, 3H), 0.56 (t, J=7.04 Hz, 3H).

Synthesis of Compound 1-20

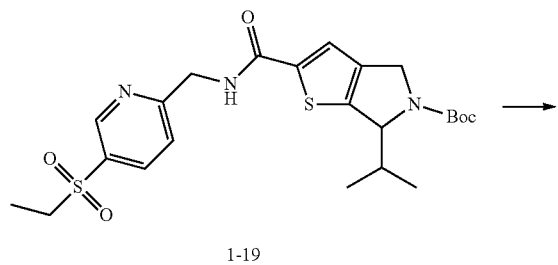

1-19

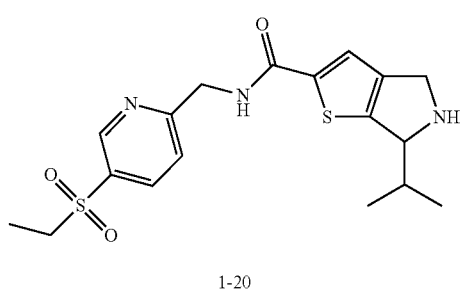

1-20

To a solution of Compound 1-19 (6.3 g) in ethyl acetate (10 mL) was added a solution of hydrogen chloride in ethyl acetate (10 mL). The reaction solution was stirred at 25° C. for 0.5 hours. After the completion of the reaction was monitored by LC-MS, the reaction solution was directly concentrated and dried by rotary evaporation to obtain the hydrochloride of Compound 1-20 as a crude product. The crude product was directly used in the next step without further purification.

MS (ESI) m/z: 394 [M+H]$^+$.

Synthesis of Example 1 and Example 2

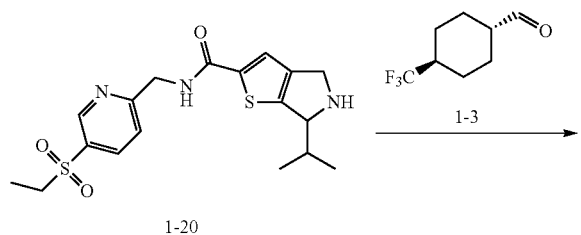

1-20

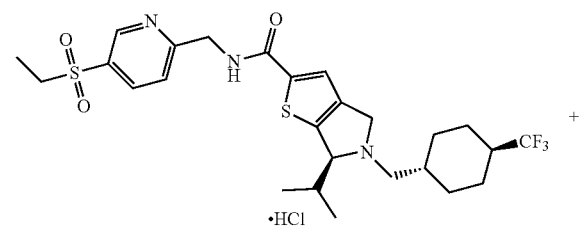

Example 1 or Example 2

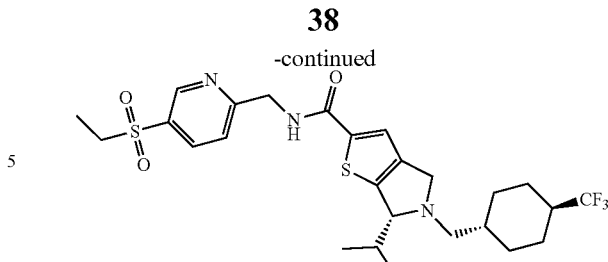

Example 1 or Example 2

Triethylamine (2.04 g, 2.8 mL) was added to a suspension of the hydrochloride of Compound 1-20 (5.5 g) in 1,2-dichloroethane (80 mL). The reaction solution was stirred at 25° C. for 0.5 hours. Thereafter, acetic acid (2.63 g, 2.5 mL), Compound 1-3 (2.6 g) and sodium borohydride acetate (5.50 g) were added to the reaction solution. After the addition, the reaction solution was stirred at 25° C. for 0.5 hours. After the completion of the reaction was monitored by thin-layer chromatography and LC-MS, the reaction solution was concentrated, and 150 mL water was added to dilute the residue. The aqueous phase was extracted three times with ethyl acetate (100 mL×3). The combined organic phases were washed once with saturated brine (100 mL), and the organic phase was dried over anhydrous sodium sulfate, filtered, and concentrated. The crude product was purified by using a flash purification system (SepaFlash® silica gel flash column (40 g), eluent: petroleum ether/ethyl acetate; elution gradient: petroleum ether/ethyl acetate (V/V)=0% to 80%; flow rate: 40 mL/min) to give a chemically pure product (i.e., a mixture of the compound of Example 1 in its free state and the compound of Example 2 in its free state). The chemically pure product was allowed to pass through SFC (column: AD (250 mm×50 mm, 10 μm); mobile phase: phase A was supercritical fluid carbon dioxide, and phase B was neutral ethanol, wherein the volume ratio of phase B was 40%; column temperature: 40° C.). The compound of Example 1 in its free state and the compound of Example 2 in its free state were obtained by separation, respectively. These compounds in their free state were purified by preparative high performance liquid chromatography (HCl system) to obtain the hydrochlorides of the compound of Example 1 and the compound of Example 2.

The compound of Example 1 was analyzed by the SFC method, and the analysis conditions were as follows: column: Chiralpak AD-3 50×4.6 mm I.D., 3 μm; mobile phase: phase A was supercritical fluid carbon dioxide, and phase B was neutral ethanol, wherein the volume ratio of phase B was 40%; flow rate: 4 mL/min; column temperature: 40° C.; retention time Rt=1.89 min.

MS (ESI) m/z: 558 [M+H]$^+$;

$^1$H NMR (400 MHz, DMSO-d6): δ 10.74 (br s, 1H), 9.52 (br s, 1H), 8.96 (d, J=2.0 Hz, 1H), 8.26 (dd, J=2.4, 8.4 Hz, 1H), 7.80 (s, 1H), 7.60 (d, J=8.0 Hz, 1H), 4.90 (br s, 2H), 4.56-4.75 (m, 2H), 4.42 (br d, J=10.4 Hz, 1H), 3.47-3.55 (m, 2H), 3.28 (br s, 3H), 1.80-2.46 (m, 7H), 1.21-1.36 (m, 2H), 0.97-1.18 (m, 10H).

The compound of Example 2 was analyzed by the SFC method, and the analysis conditions were as follows: Chiralpak AD-3 50×4.6 mm I.D., 3 jam; mobile phase: phase A was supercritical fluid carbon dioxide, and phase B was neutral ethanol, wherein the volume ratio of phase B was 40%; flow rate: 4 mL/min; column temperature: 40° C.; retention time Rt=1.18 min.

MS (ESI) m/z: 558 [M+H]⁺;

1H NMR (CHLOROFORM-d): δ 8.98 (s, 1H), 8.10 (dd, J=8.2, 2.1 Hz, 1H), 7.49 (d, J=8.2 Hz, 1H), 7.26 (s, 1H), 7.00-7.11 (m, 1H), 4.72-4.82 (m, 2H), 4.13 (dd, J=12.4, 3.6 Hz, 1H), 3.78-3.86 (m, 1H), 3.42 (dd, J=12.4, 3.1 Hz, 1H), 3.09 (q, J=7.3 Hz, 2H), 2.41-2.58 (m, 1H), 2.10-2.20 (m, 1H), 1.85-1.99 (m, 3H), 1.23-1.31 (m, 6H), 1.15-1.22 (m, 3H), 1.00 (d, J=7.0 Hz, 3H), 0.88 (br d, J=11.5 Hz, 1H), 0.79-0.85 (m, 1H), 0.75 (d, J=6.8 Hz, 3H).

Example 3 and Example 4

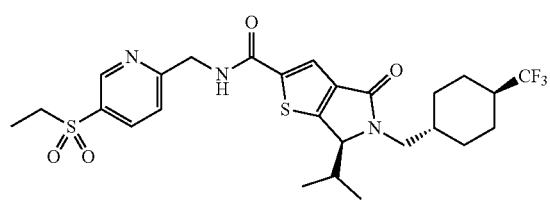

Example 3 or Example 4

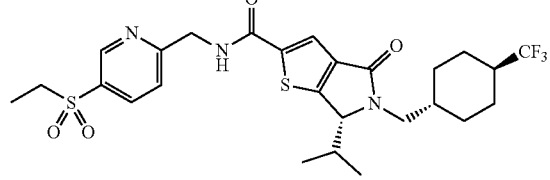

Example 3 or Example 4

In Examples 1 and 2, a mixture of the compound of Example 1 in its free state and the compound of Example 2 in its free state, which was not separated by SFC, was placed in the air. An oxygenated product appeared and was purified by preparative high performance liquid chromatography (HCl system) to obtain a mixture of Example 3 and Example 4.

The mixture of Example 3 and Example 4 was allowed to pass through SFC (column: AD (250 mm×30 mm, 10 μm). Mobile phase: phase A was supercritical fluid carbon dioxide, and phase B was ethanol containing 0.1% aqueous ammonia, wherein the volume ratio of phase B was 50%. Example 3 and Example 4 were obtained by separation, respectively.

The compound of Example 3 was analyzed by the SFC method, and the analysis conditions were as follows: column: Chiralpak AD-3 50×4.6 mm I.D., 3 jam; mobile phase: phase A was supercritical fluid carbon dioxide, and phase B was ethanol containing 0.05% diethylamine, wherein the volume ratio of phase B was 40%; flow rate: 4 mL/min; column temperature: 40° C.; retention time Rt=1.086 min.

MS (ESI) m/z: 572.1 [M+H]⁺;

¹H NMR (400 MHz, DMSO-d6): δ 9.50 (s, 1H), 8.97 (d, J=2.00 Hz, 1H), 8.26 (dd, J=2.4, 8.4 Hz, 1H), 8.02 (s, 1H), 7.64 (d, J=8.0 Hz, 1H), 4.80 (d, J=3.6 Hz, 1H), 4.62-4.71 (m, 2H), 3.52-3.58 (m, 1H), 3.45 (m, 2H), 2.89-3.01 (m, 1H), 2.23 (m, 1H), 1.74-1.96 (m, 4H), 1.55-1.71 (m, 2H), 1.17 (m, 10H), 0.38 (d, J=6.4 Hz, 3H).

The compound of Example 4 was analyzed by the SFC method, and the analysis conditions were as follows: column: Chiralpak AD-3 50×4.6 mm I.D., 3 m; mobile phase: phase A was supercritical fluid carbon dioxide, and phase B was ethanol containing 0.05% diethylamine; elution gradient: a volume ratio of 40%; flow rate: 4 mL/min; column temperature: 40° C.; retention time Rt=0.692 min.

MS (ESI) m/z 572.1 [M+H]⁺;

¹H NMR (400 MHz, DMSO-d₆): δ 9.43 (t, J=5.6 Hz, 1H), 8.97 (d, J=2.0 Hz, 1H), 8.26 (dd, J=2.4, 8.40 Hz, 1H), 8.00 (s, 1H), 7.64 (d, J=8.4 Hz, 1H), 4.80 (d, J=3.6 Hz, 1H), 4.68 (m, 2H), 3.57-3.63 (m, 1H), 3.40 (m, 2H), 2.96 (br dd, J=4.0, 14.0 Hz, 1H), 2.20 (m, 1H), 1.76-1.94 (m, 4H), 1.53-1.72 (m, 2H), 1.07-1.23 (m, 10H), 0.39 (d, J=6.0 Hz, 3H).

Example 5 and Example 6

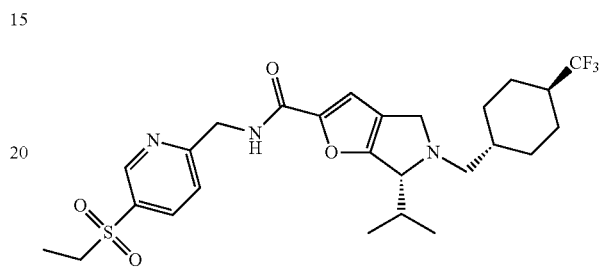

Example 5 or Example 6

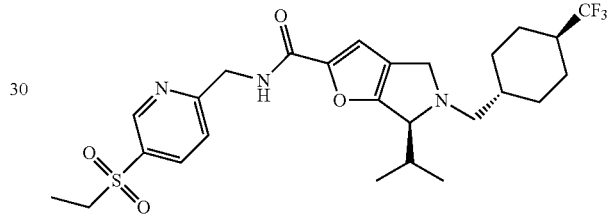

Example 5 or Example 6

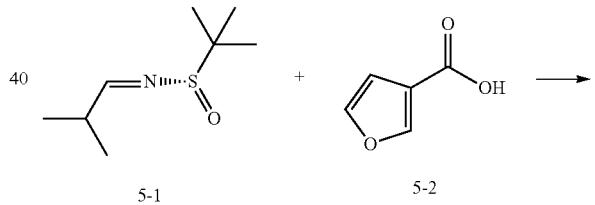

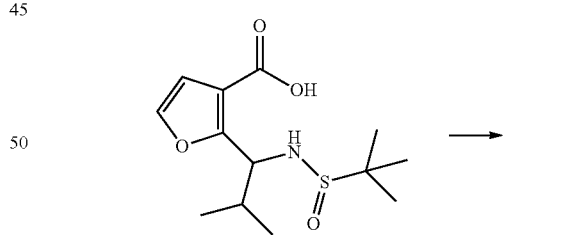

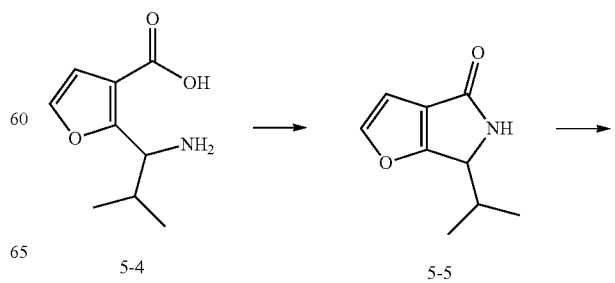

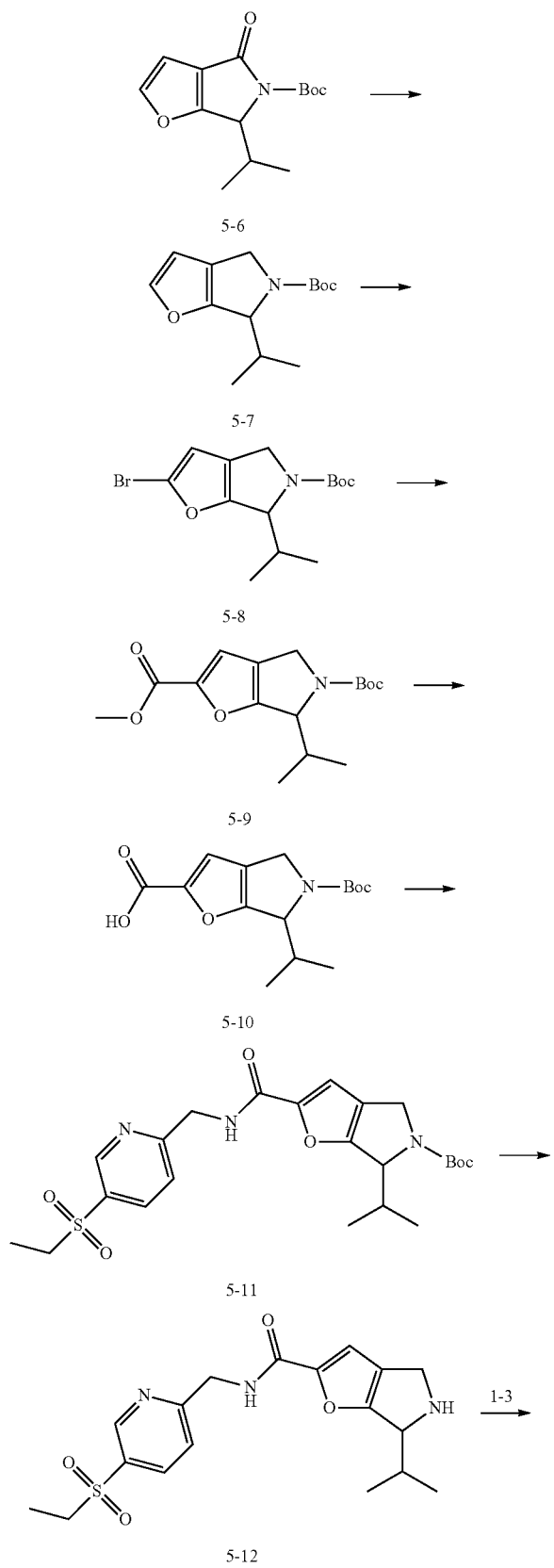

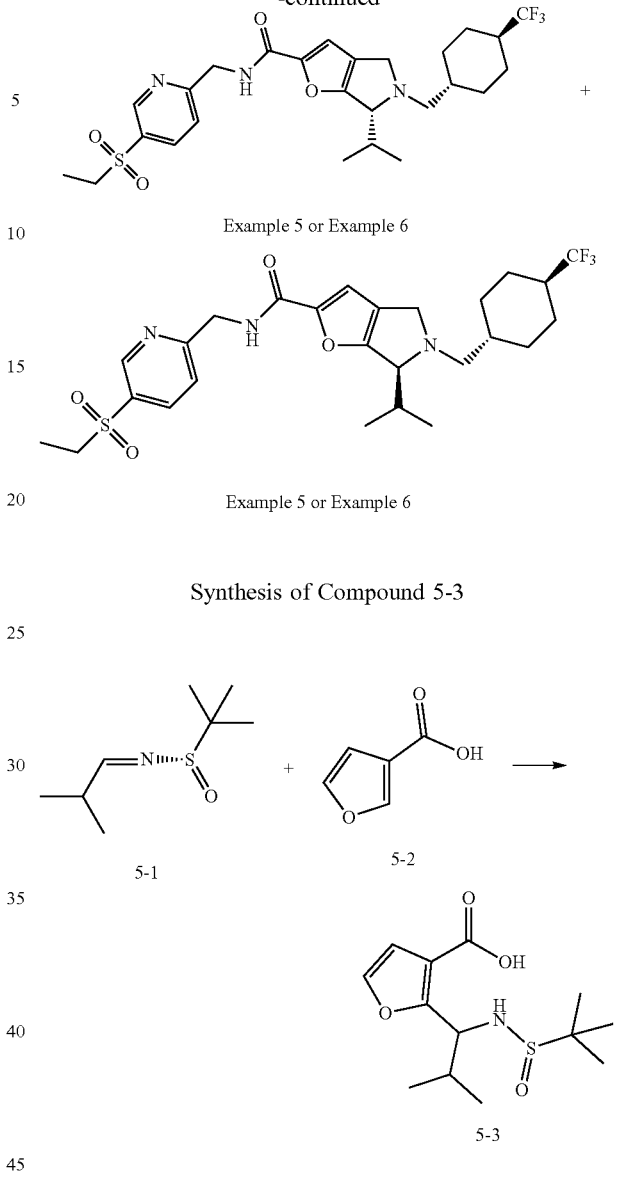

Synthesis of Compound 5-3

LDA (2 M, 206.10 mL, 2.31 eq) was added dropwise to a solution of Compound 5-2 (20 g, 178.44 mmol, 1 eq) in anhydrous tetrahydrofuran (100 mL) at 0° C. under the protection of nitrogen. The reaction solution was stirred at 0° C. for 0.5 hours, and then a solution of Compound 5-1 in anhydrous tetrahydrofuran (100 mL) was slowly added to this reaction solution within 1 hour. Upon the completion of the dropwise addition, the reaction solution was heated to 20° C. and stirred for 1 hour. When LC-MS showed the completion of the reaction, water (100 mL) was added to quench the reaction, and the reaction solution was separated into different layers. The separated aqueous phase was washed with ethyl acetate (200 mL), and then the pH was adjusted to 3 using hydrochloric acid (1 N, 50 mL), followed by the extraction with ethyl acetate (250 mL×3). The combined organic layers were washed with saturated brine (180 mL), dried over anhydrous sodium sulfate, and filtered. The filtrate was concentrated under reduced pressure to give Compound 5-3 (racemate, the R/S ratio was about 1:1).

MS (ESI) m/z: 287.9 [M+H]$^+$ $^1$H NMR (CHLOROFORM-d): δ 7.27 (d, J=2.0 Hz, 1H), 7.21 (d, J=2.0 Hz, 1H), 6.63 (d, J=2.0 Hz, 1H), 6.60 (d, J=2.0

Hz, 1H), 4.71-4.79 (m, 1H), 4.45 (dd, J=10.4, 8.4 Hz, 1H), 2.12-2.23 (m, 1H), 2.05-2.12 (m, 1H), 1.17-1.21 (m, 18H), 1.02 (d, J=6.8 Hz, 3H), 0.97 (d, J=6.8 Hz, 3H), 0.76 (d, J=6.4 Hz, 3H), 0.72 (d, J=6.8 Hz, 3H).

Synthesis of Compound 5-4

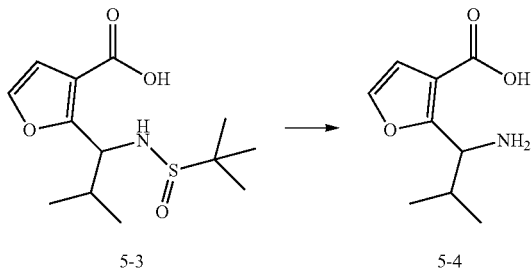 [SMILES: CC(C)C(NS(=O)C(C)(C)C)c1occc1C(=O)O ; CC(C)C(N)c1occc1C(=O)O]

Compound 5-3 (30.26 g, 105.30 mmol, 1 eq) was dissolved in hydrochloric acid/ethyl acetate (60 mL), and the mixture was stirred and reacted at 20° C. for 1 hour. When LC-MS showed the completion of the reaction, the reaction solution was filtered, and the residue was washed with ethyl acetate to obtain Compound 5-4.

MS (ESI) m/z: 166.9 [M+H]$^+$ $^1$HNMR (DMSO-d$_6$): δ 8.80 (br s, 3H), 7.87 (d, J=1.6 Hz, 1H), 6.76 (d, J=1.6 Hz, 1H), 4.72 (br s, 1H), 2.21-2.37 (m, 1H), 1.01 (d, J=6.4 Hz, 3H), 0.78 (d, J=6.8 Hz, 3H).

Synthesis of Compound 5-5

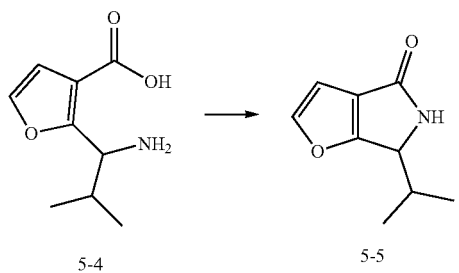

Compound 5-4 (4.4 g, 20.03 mmol, 1 eq, HCl) was dissolved in anhydrous DMF (450 mL), and triethylamine (6.08 g, 60.09 mmol, 8.36 mL, 3 eq) was added thereto. After the mixture was stirred at 20° C. for 0.5 hours, HATU (11.42 g, 30.05 mmol, 1.5 eq) was added, and the mixture was stirred for another 0.5 hours. When LC-MS showed the completion of the reaction, the reaction solution was concentrated under reduced pressure to remove DMF, ethyl acetate (80 mL) was added thereto, and then the resulting mixture was washed with water (50 mL×2). The organic layer was washed with saturated brine (60 mL), and then dried over anhydrous sodium sulfate and filtered. The filtrate was concentrated under reduced pressure to obtain a crude product. The crude product was purified by a flash column (SepaFlash® silica gel flash column (40 g), eluent: ethyl acetate and petroleum ether; elution gradient: 0% to 60%; flow rate: 35 mL/min) to obtain Compound 5-5.

MS (ESI) m/z: 166.0 [M+H]$^+$ $^1$H NMR (CHLOROFORM-d): δ 7.50 (d, J=1.6 Hz, 1H), 6.81 (br s, 1H), 6.62 (d, J=2.0 Hz, 1H), 4.36 (d, J=5.6 Hz, 1H), 1.99-2.16 (m, 1H), 1.04 (d, J=6.8 Hz, 3H), 1.00 (d, J=6.8 Hz, 3H).

Synthesis of Compound 5-6

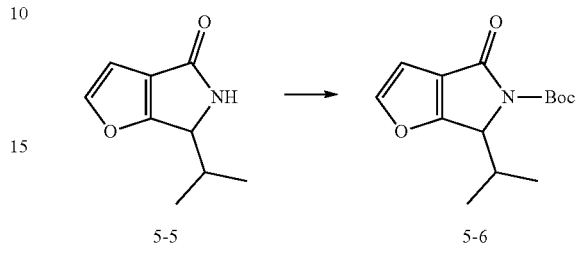

Compound 5-5 (2.4 g, 14.53 mmol, 1 eq) was dissolved in anhydrous dichloromethane (30 mL), DMAP (177.50 mg, 1.45 mmol, 0.1 eq), triethylamine (2.94 g, 29.06 mmol, 4.04 mL, 2 eq) and Boc anhydride (3.49 g, 15.98 mmol, 3.67 mL, 1.1 eq) were added thereto, and the mixture was stirred and reacted at 20° C. for 1 hour. When LC-MS showed the completion of the reaction, water (20 mL) was added to dilute the resulting mixture, and the mixture was extracted with dichloromethane (20 mL×2). The combined organic layers were washed with water (15 mL), and then dried over anhydrous sodium sulfate and filtered. The filtrate was concentrated under reduced pressure to give a crude product. The crude product was purified by a flash column (SepaFlash® silica gel flash column (40 g), eluent: ethyl acetate and petroleum ether; elution gradient: 0% to 30%; flow rate: 35 mL/min) to obtain Compound 5-6.

MS (ESI) m/z: 210.0 [M+H]$^+$ $^1$H NMR (CHLOROFORM-d): δ 7.44 (d, J=1.6 Hz, 1H), 6.56 (d, J=2.0 Hz, 1H), 4.79 (d, J=3.6 Hz, 1H), 2.48-2.66 (m, 1H), 1.50 (s, 9H), 1.15 (d, J=7.2 Hz, 3H), 0.49 (d, J=6.8 Hz, 3H).

Synthesis of Compound 5-7

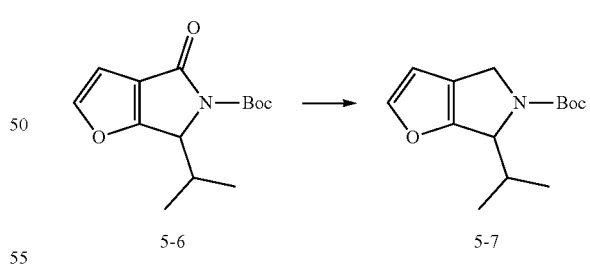

Borane-dimethylsulfide (10 M, 5.01 mL, 4 eq) was added slowly to a solution of Compound 5-6 (3.32 g, 12.51 mmol, 1 eq) in anhydrous tetrahydrofuran (60 mL), and the mixture was stirred and reacted at 60° C. for 1 hour. When LC-MS showed the completion of the reaction, methanol (20 mL) was slowly added at 20° C. to quench the reaction. The resulting mixture was then concentrated under reduced pressure to remove methanol and tetrahydrofuran, water (20 mL) was then added to dilute the mixture, and the mixture was extracted with ethyl acetate (30 mL×2). The combined organic layers were washed with saturated brine (30 mL), and then dried over anhydrous sodium sulfate and filtered. The filtrate was concentrated under reduced pressure to obtain a crude product, which was purified by a flash column (SepaFlash® silica gel flash column (20 g), eluent: ethyl acetate and petroleum ether; elution gradient: 0% to 20%; flow rate: 30 mL/min) to obtain Compound 5-7.

MS (ESI) m/z: 196.0 [M+H]$^+$ $^1$H NMR (CHLOROFORM-d): δ 7.30 (d, J=1.2 Hz, 1H), 6.24 (dd, J=17.2, 1.6 Hz, 1H), 4.56-4.77 (m, 1H), 4.26-4.44 (m, 1H), 4.12-4.23 (m, 1H), 2.21-2.57 (m, 1H), 1.43 (s, 9H), 1.00 (t, J=7.6 Hz, 3H), 0.53 (dd, J=6.8, 3.6 Hz, 3H).

Synthesis of Compound 5-8

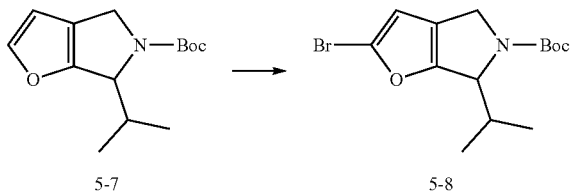 [SMILES: CC(C)C1c2occc2CN1C(=O)OC(C)(C)C ; CC(C)C1c2oc(Br)cc2CN1C(=O)OC(C)(C)C]

At 0° C., NBS (1.56 g, 8.75 mmol, 1.1 eq) was added to a solution of Compound 5-7 (2 g, 7.96 mmol, 1 eq) in acetonitrile (20 mL), and the mixture was stirred and reacted at 0° C. for 1 hour. When LC-MS showed the completion of the reaction, the reaction solution was concentrated under reduced pressure to remove acetonitrile, water (10 mL) was then added to dilute the mixture, and the mixture was extracted with ethyl acetate (20 mL×2). The combined organic layers were washed with saturated brine (15 mL), and then dried over anhydrous sodium sulfate and filtered. The filtrate was concentrated under reduced pressure to obtain a crude product, which was purified by a flash column (SepaFlash® silica gel flash column (20 g), eluent: ethyl acetate and petroleum ether; elution gradient: 0% to 20%; flow rate: 30 mL/min) to obtain Compound 5-8.

MS (ESI) m/z: 273.9 [M+H]$^+$;

$^1$H NMR (CHLOROFORM-d): δ 6.19 (d, J=16.4 Hz, 1H), 4.56-4.75 (m, 1H), 4.26-4.41 (m, 1H), 4.16 (dd, J=13.2, 4.4 Hz, 1H), 2.21-2.53 (m, 1H), 1.42 (s, 9H), 0.99 (t, J=7.6 Hz, 3H), 0.56 (dd, J 6.8, 3.6 Hz, 3H).

Synthesis of Compound 5-9

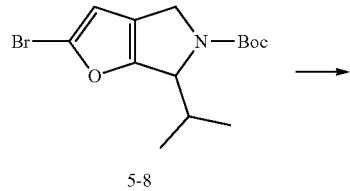

Compound 5-8 (0.57 g, 1.73 mmol, 1 eq) was dissolved in anhydrous methanol (4 mL) and anhydrous DMF (1 mL), and triethylamine (192.13 mg, 1.90 mmol, 264.28 μL, 1.1 eq) and Pd(dppf)Cl$_2$.CH$_2$Cl$_2$ (140.96 mg, 172.61 μmol, 0.1 eq) were added thereto under the protection of nitrogen. After the reaction solution was purged with carbon monoxide for three times, the reaction solution was stirred and reacted at 60° C. and 50 psi for 16 hours. When LC-MS showed the completion of the reaction, the reaction solution was concentrated under reduced pressure to remove methanol and DMF, water (5 mL) was added to dilute the reaction solution, and the resulting mixture was extracted with ethyl acetate (6 mL×3). The combined organic layers were washed with saturated brine (8 mL), and then dried over anhydrous sodium sulfate and filtered. The filtrate was concentrated under reduced pressure to obtain a crude product, which was purified by a flash column (SepaFlash® silica gel flash column (4 g), eluent: ethyl acetate and petroleum ether; elution gradient: 0% to 20%; flow rate: 18 mL/min) to obtain Compound 5-9.

MS (ESI) m/z: 254.0 [M+H]$^+$;

$^1$H NMR (CHLOROFORM-d): δ 7.02 (d, J=11.2 Hz, 1H), 4.58-4.84 (m, 1H), 4.28-4.48 (m, 1H), 4.19 (dd, J=13.6, 3.6 Hz, 1H), 3.82 (s, 3H), 2.23-2.58 (m, 1H), 1.43 (s, 9H), 0.95-1.11 (m, 3H), 0.57 (dd, J=6.4, 4.4 Hz, 3H).

Synthesis of Compound 5-10

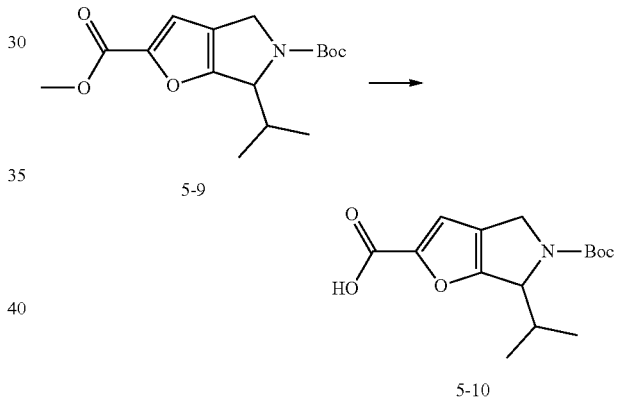

To a solution of Compound 5-9 (0.51 g, 1.65 mmol, 1 eq) in methanol (5 mL) and water (1.25 mL) was added sodium hydroxide (131.88 mg, 3.30 mmol, 2 eq). The reaction solution was stirred and reacted at 50° C. for 1 hour. When LC-MS showed the completion of the reaction, MeOH (6 mL) was added at 50° C. to quench the reaction. After the mixture was concentrated under reduced pressure to remove methanol and water, a sodium salt of Compound 5-10 was obtained.

MS (ESI) m/z: 240.0 [M+H]$^+$

Synthesis of Compound 5-11

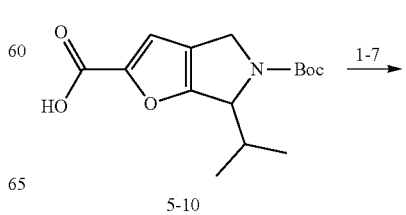

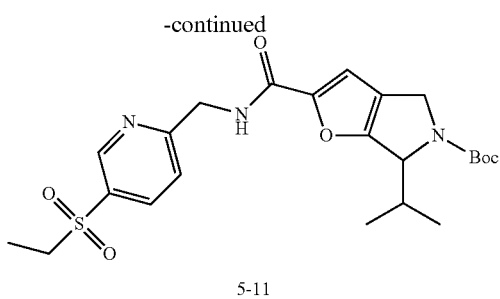

5-11

The sodium salt of Compound 5-10 (0.49 g, 1.66 mmol, 1 eq) was dissolved in anhydrous DMF (6 mL), HATU (946.29 mg, 2.49 mmol, 1.5 eq), Compound 1-7 (398.71 mg, 1.99 mmol, 1.2 eq) and DIPEA (643.30 mg, 4.98 mmol, 866.99 μL, 3 eq) were added, and the mixture was stirred and reacted at 20° C. for 1 hour. When LC-MS showed the completion of the reaction, the reaction solution was concentrated under reduced pressure to remove DMF, and then dissolved in ethyl acetate (20 mL), washed with water (10 mL×3), dried over anhydrous sodium sulfate and filtered. The filtrate was concentrated under reduced pressure to obtain a crude product. The crude product was purified by a flash column (SepaFlash® silica gel flash column (4 g), eluent: ethyl acetate and petroleum ether; elution gradient: 0% to 70%; flow rate: 18 mL/min) to obtain Compound 5-11.

MS (ESI) m/z: 478.1 [M+H]$^+$;

$^1$H NMR (CHLOROFORM-d): δ 8.99 (d, J=2.0 Hz, 1H), 8.10 (dd, J=8.0, 2.4 Hz, 1H), 7.95 (s, 1H), 7.50 (d, J=8.4 Hz, 1H), 7.28-7.37 (m, 1H), 7.03 (d, J=11.6 Hz, 1H), 4.72-4.88 (m, 2H), 4.30-4.48 (m, 1H), 4.14-4.27 (m, 1H), 3.05-3.13 (m, 2H), 1.43 (s, 8H), 1.39-1.41 (m, 1H), 1.23-1.27 (m, 3H), 1.00-1.08 (m, 3H), 0.59 (t, J=6.0 Hz, 3H).

Synthesis of Compound 5-12

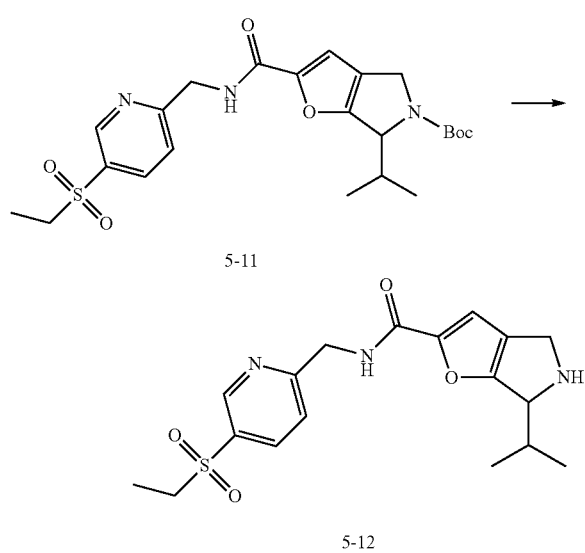

A solution of Compound 5-11 (0.3 g, 628.18 μmol, 1 eq) in HCl/EtOAc (5 mL) was stirred and reacted at 20° C. for 1 hour. When LC-MS showed the completion of the reaction, the reaction solution was concentrated under reduced pressure to remove ethyl acetate, so as to obtain the hydrochloride of Compound 5-12.

MS (ESI) m/z: 378.0 [M+H]$^+$.

Example 5 and Example 6

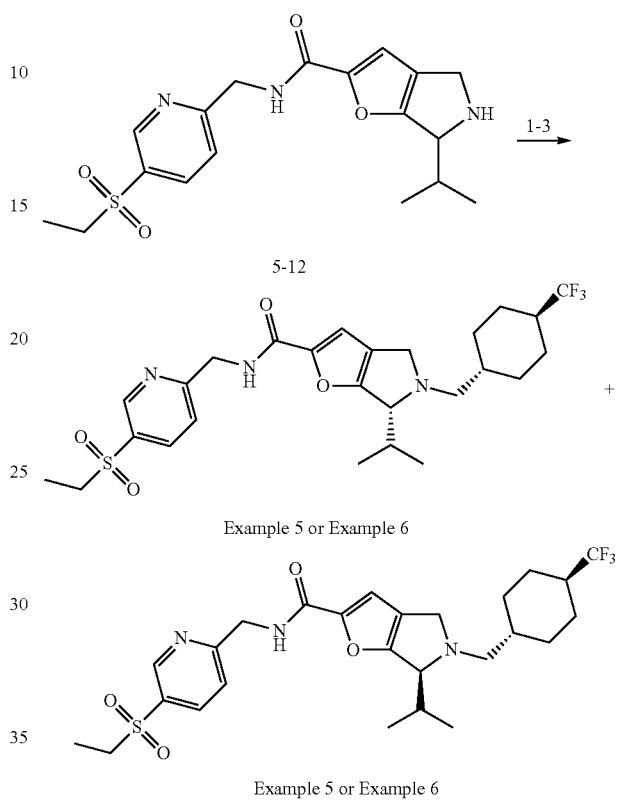

Triethylamine (67.23 mg, 664.38 μmol, 92.47 b L, 1.1 eq) was added to a solution of Compound 5-12 (0.25 g, 603.98 μmol, 1 eq, HCl) in anhydrous dichloroethane (5 mL), and the resulting mixture was stirred at 20° C. for 1 hour. Subsequently, acetic acid (36.27 mg, 603.98 mol, 34.54 μL, 1 eq) was added to adjust the pH to 5, followed by the addition of Compound 1-3 and NaBH(OAc)$_3$ (384.03 mg, 1.81 mmol, 3 eq). The reaction solution was stirred for an additional hour at 20° C. When LC-MS showed the completion of the reaction, a saturated ammonium chloride solution was added to quench the reaction, and the mixture was extracted with dichloromethane (5 mL×3). The combined organic layers were washed with saturated brine (6 mL) and then dried over anhydrous sodium sulfate to obtain a crude product. The crude product was purified by a flash column (SepaFlash® silica gel flash column (4 g), eluent: ethyl acetate and petroleum ether; elution gradient: 0% to 30%; flow rate: 18 mL/min) to obtain a chemically pure product (a mixture of Example 5 and Example 6). The chemically pure product was separated by SFC to give Example 5 and Example 6. The specific separation conditions of SFC were as follows: SFC (column: AD (250 mm×30 mm, 5 μm); mobile phase: phase A was supercritical fluid carbon dioxide, and phase B was isopropanol containing 0.1% aqueous ammonia, wherein the volume ratio of phase B was 35%.

Example 5

The retention time Rt of the SFC analysis was 3.772 min. The SFC analysis conditions were as follows: (column:

Chiralpak AD-3 100 mm×4.6 mm, I.D. 3 μm); mobile phase: phase A was supercritical fluid carbon dioxide, and phase B was isopropanol containing 0.05% diethylamine; gradient: the volume ratio of the mobile phase B was increase from 5% to 40% within 4.5 minutes, kept at 40% for 2.5 minutes, and then kept at 5% for 1 minute; flow rate: 2.8 mL/min; column temperature: 40° C.

MS (ESI) m/z: 542.3 [M+H]⁺;

¹H NMR (CHLOROFORM-d): δ 8.98 (br s, 1H), 8.09 (br d, J=7.2 Hz, 1H), 7.49 (br d, J 7.6 Hz, 1H), 6.96 (br s, 1H), 4.56-4.95 (m, 2H), 3.97 (br d, J=9.2 Hz, 1H), 3.62 (br s, 1H), 3.27 (br d, J=11.6 Hz, 1H), 3.09 (br d, J=7.2 Hz, 2H), 2.58 (br d, J=8.8 Hz, 1H), 2.43 (br t, J=10.4 Hz, 1H), 2.15 (br d, J=11.2 Hz, 1H), 1.91 (br d, J=8.0 Hz, 2H), 1.76 (br d, J=12.4 Hz, 3H), 1.38 (br s, 1H), 1.25 (br s, 6H), 1.00 (br d, J=6.4 Hz, 3H), 0.77 (br d, J=5.6 Hz, 4H).

Example 6

The retention time Rt of the SFC analysis was 4.337 min. The SFC analysis conditions were as follows: (column: Chiralpak AD-3 100 mm×4.6 mm, I.D. 3 μm); mobile phase: phase A was supercritical fluid carbon dioxide, and phase B was isopropanol containing 0.05% diethylamine; gradient: the volume ratio of mobile phase B was increased from 5% to 40% within 4.5 minutes, kept at 40% for 2.5 minutes, and then kept at 5% for 1 minute; flow rate: 2.8 mL/min; column temperature: 40° C.

MS (ESI) m/z: 542.3 [M+H]⁺;

¹H NMR (CHLOROFORM-d): δ 8.98 (br s, 1H), 8.09 (br d, J=8.0 Hz, 1H), 7.49 (br d, J=8.0 Hz, 1H), 7.22 (br s, 1H), 6.96 (s, 1H), 4.55-4.97 (m, 2H), 3.97 (br d, J=11.2 Hz, 1H), 3.62 (br s, 1H), 3.27 (br d, J=11.6 Hz, 1H), 3.09 (q, J=7.2 Hz, 2H), 2.50-2.70 (m, 1H), 2.43 (br t, J=10.8 Hz, 1H), 2.15 (br d, J=12.0 Hz, 1H), 1.91 (br d, J=10.0 Hz, 3H), 1.75 (br d, J=13.6 Hz, 2H), 1.09-1.48 (m, 7H), 1.00 (br d, J=6.8 Hz, 3H), 0.82-0.94 (m, 1H), 0.77 (br d, J=6.4 Hz, 3H).

Example 7 and Example 8

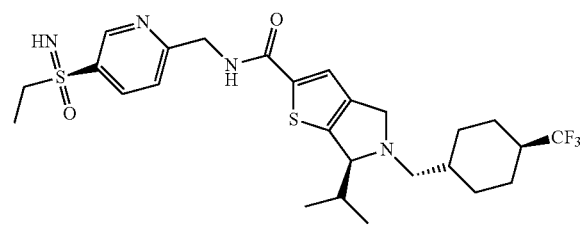

Example 7 or Example 8

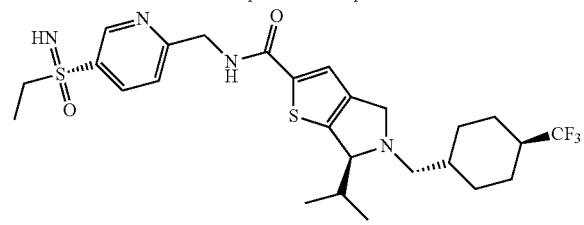

Example 7 or Example 8

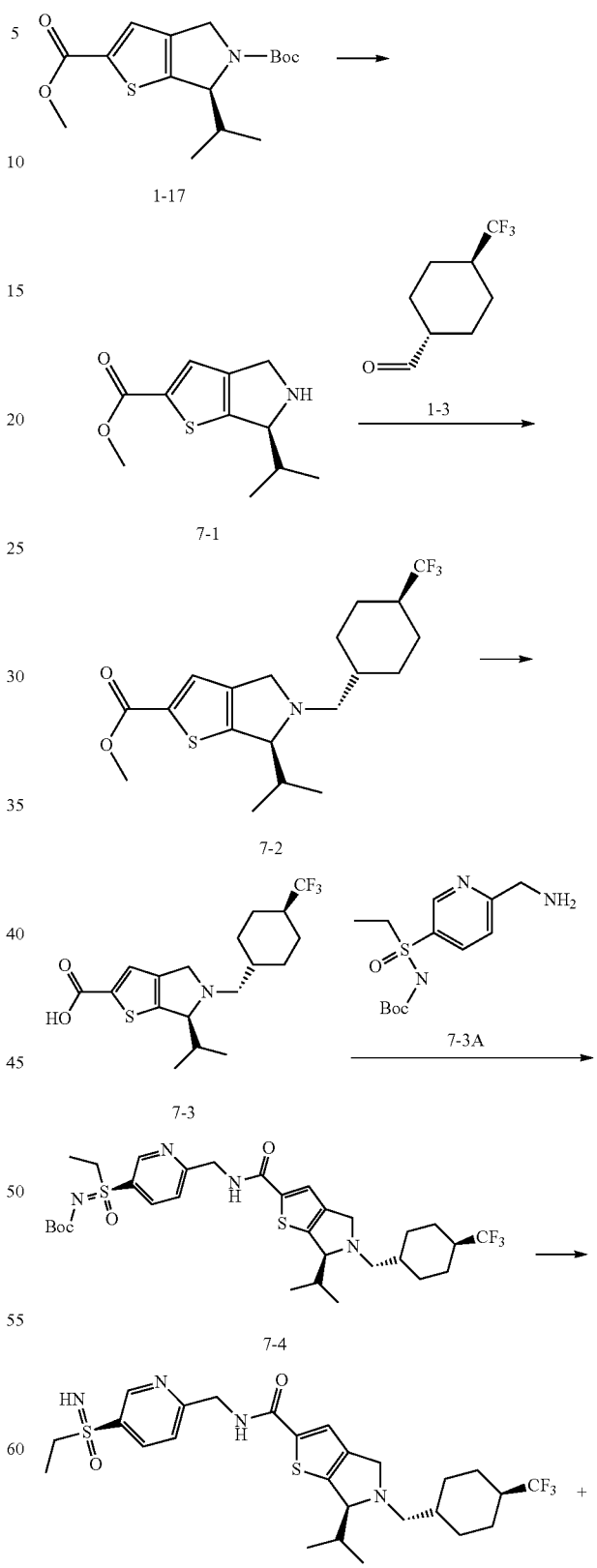

Example 7 or Example 8

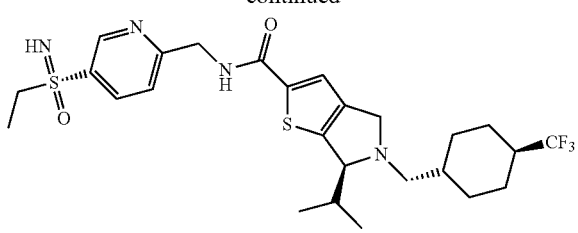

Example 7 or Example 8

Synthesis of Compound 7-1

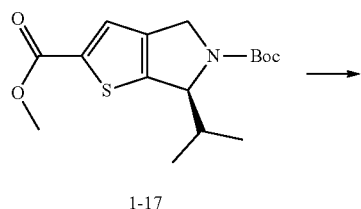

1-17

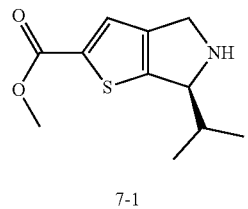

7-1

A mixed solution of Compound 1-17 (5 g, 15.36 mmol, 1 eq) and HCl/EtOAc (4 M, 3.84 mL, 1 eq) was stirred at 20 to 30° C. for one hour. LC-MS showed that Compound 1-17 was completely consumed and the formation of the target product was detected. After the reaction solution was concentrated under reduced pressure to remove the solvent, the hydrochloride of Compound 7-1 was obtained. The crude product was used directly in the next step without further purification.

MS (ESI) m/z: 225.9 [M+H]$^+$;

Synthesis of Compound 7-2

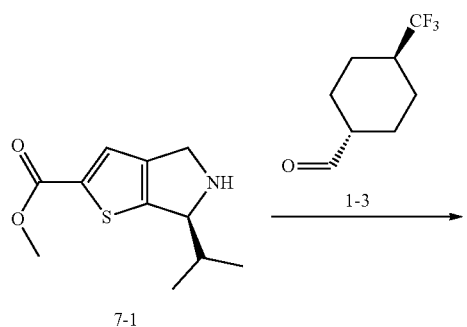

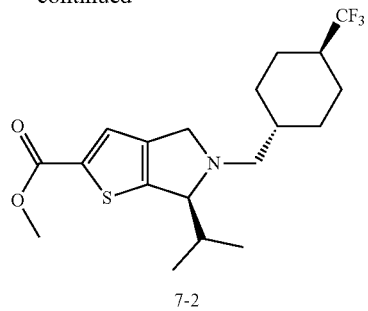

7-2

Et$_3$N (1.53 g, 15.13 mmol, 2.11 mL, 1.2 eq) was added to a solution of Compound 7-1 (3.3 g, 12.61 mmol, hydrochloride) in 40 mL DCE, and then the mixture was stirred at 20 to 30° C. for 30 minutes. Thereafter, AcOH (2.27 g, 37.82 mmol, 2.16 mL, 3 eq) was added to adjust the pH to 5, and Compound 1-3 (4.54 g, 25.21 mmol, 2 eq) and NaBH(OAc)$_3$ (5.34 g, 25.21 mmol, 2 eq) were added in sequence. The reaction solution was stirred at 20 to 30° C. for 15.5 hours. LC-MS showed that Compound 7-1 was completely consumed and the formation of the target product was detected. 100 mL saturated sodium bicarbonate solution was added slowly to the reaction solution to quench the reaction, and then the reaction solution was extracted twice with 200 mL dichloromethane. The combined organic phases were washed with 200 mL saturated brine, dried over anhydrous sodium sulfate, filtered and concentrated under reduced pressure to give a crude product. The crude product was allowed to pass through a flash purification system (Sepa-Flash® silica gel flash column (40 g), eluent: petroleum ether/ethyl acetate; elution gradient: ethyl acetate/petroleum ether (V/V)=0% to 50%; flow rate: 40 mL/min), and Compound 7-2 was obtained after the purification.

MS (ESI) m/z: 415.0 [M+H]$^+$.

Synthesis of Compound 7-3

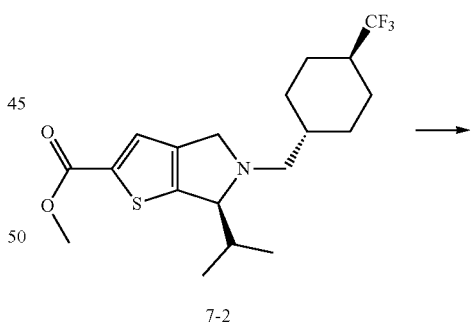

7-2

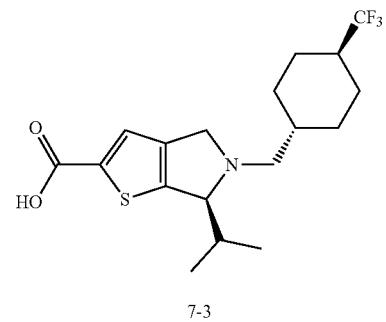

7-3

To a solution of Compound 7-2 (1 g, 2.57 mmol, 1 eq) in 8 mL THF and 2 mL H₂O was added LiOH.H₂O (323.23 mg, 7.70 mmol, 3 eq). The reaction solution was stirred at 35° C. for 16 hours. LC-MS showed that Compound 7-2 was completely consumed and the formation of the target product was detected. The pH of the reaction solution was adjusted to 3 with an aqueous hydrochloric acid solution, and then the reaction solution was extracted twice with 100 mL ethyl acetate. The combined organic phases were washed with 50 mL saturated brine, dried over anhydrous sodium sulfate, filtered and concentrated under reduced pressure to give Compound 7-3, which was used directly in the next step without further purification.

MS (ESI) m/z: 376.1 [M+H]⁺.

Synthesis of Compound 7-4

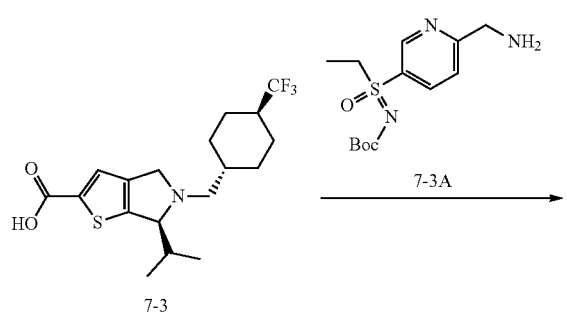

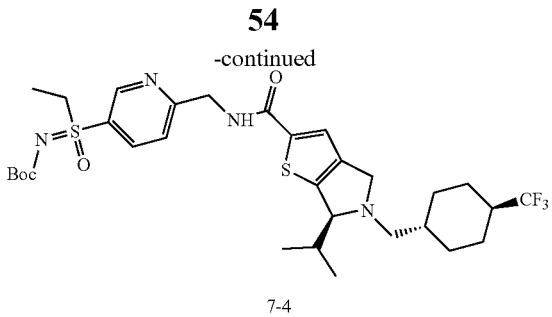

To a solution of Compound 7-3 (1 g, 1.41 mmol, 1 eq) in 10 mL DMF, HATU (800 mg, 2.10 mmol, 1.49 eq) and DIPEA (593.60 mg, 4.59 mmol, 0.8 mL, 3.26 eq) were added. The reaction solution was stirred at 20 to 30° C. for 30 minutes, then Compound 7-3A (500 mg, 1.67 mmol, 1.18 eq) was added, and the resulting mixture was stirred at 20 to 30° C. for 15.5 hours. LC-MS showed that Compound 7-4 was completely consumed and the target product was formed. The reaction solution was dispersed in 50 mL water and 50 mL ethyl acetate. The organic phase was separated, washed with 50 mL saturated brine, dried over anhydrous sodium sulfate, filtered and concentrated under reduced pressure to give a crude product. The crude product was allowed to pass through a flash purification system (Sepa-Flash® silica gel flash column (12 g), eluent: petroleum ether/ethyl acetate; elution gradient: ethyl acetate/petroleum ether (V/V)=0% to 100%; flow rate: 30 mL/min) to be purified, and Compound 7-4 was obtained.

MS (ESI) m/z: 657.2 [M+H]⁺.

Synthesis of Example 7 and Example 8

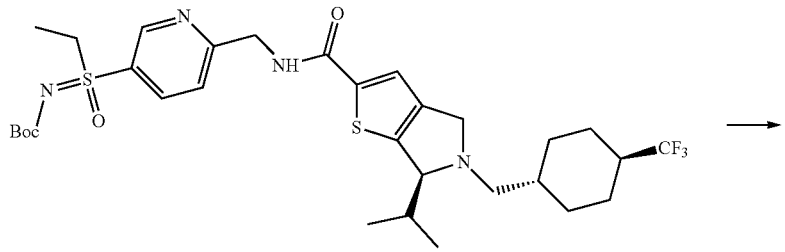

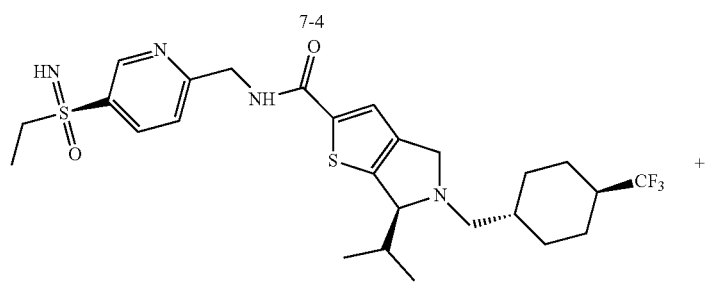

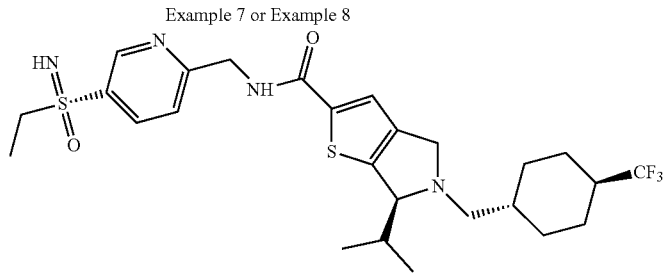

Example 7 or Example 8

A mixed solution of Compound 7-4 (500.00 mg, 403.46 μmol, 1 eq) and HCl/dioxane (4 M, 33.13 mL, 328.41 eq) was reacted at 20 to 30° C. for one hour. LC-MS showed that the starting materials were completely consumed and the formation of the target product was detected. The reaction solution was concentrated under reduced pressure to give a crude product. The crude product was prepared by HPLC (column model: YMC-Actus Triart C18 100×30 mm×5 μm; mobile phase: [phase A was water containing 0.05% HCl; and phase B was acetonitrile]; elution gradient: content of phase B: 20% to 90%, 10 min) to obtain the target product, which was further resolved by SFC (separation conditions: column model: C2 250 mm×30 mm, 10 μm; mobile phase: phase A was supercritical fluid carbon dioxide, and phase B was ethanol; elution gradient (v/v): B %=45% to 45%) to obtain Example 7 and Example 8.

Example 7

The retention time Rt of the SFC analysis was 6.588 min. The SFC analysis conditions were as follows: (column: Lux Cellulose-2 150 mm×4.6 mm, I.D. 3 μm); mobile phase: phase A was supercritical fluid carbon dioxide, and phase B was methanol containing 0.05% diethylamine, wherein the volume ratio of phase B was 40%; flow rate: 2.5 mL/min; column temperature: 40° C.

MS (ESI) m/z: 557.1 [M+H]$^+$;

$^1$H NMR (400 MHz, METHANOL-d4) δ ppm 9.18 (s, 1H), 8.51 (br d, J=6.6 Hz, 1H), 7.70-7.91 (m, 2H), 4.99 (br s, 1H), 4.83 (s, 2H), 4.53 (br d, J=12.0 Hz, 1H), 4.12 (br d, J=7.0 Hz, 2H), 3.41 (br s, 2H), 2.45 (br s, 1H), 1.76-2.34 (m, 7H), 1.37-1.50 (m, 5H), 1.17-1.31 (m, 5H), 1.08 (br d, J=5.2 Hz, 3H).

Example 8

The retention time Rt of the SFC analysis was 7.542 min. The SFC analysis conditions were as follows: (column: Lux Cellulose-2 150 mm×4.6 mm, I.D. 3 μm); mobile phase: phase A was supercritical fluid carbon dioxide, and phase B was methanol containing 0.05% diethylamine, wherein the volume ratio of phase B was 40%; flow rate: 2.5 mL/min; column temperature: 40° C.

MS (ESI) m/z: 557.1 [M+H]$^+$;

$^1$H NMR (400 MHz, METHANOL-d4) δ ppm 9.19 (s, 1H), 8.52 (br d, J=6.0 Hz, 1H), 7.73-7.89 (m, 2H), 4.99-5.01 (m, 1H), 5.00 (br s, 1H), 4.84 (s, 2H), 4.54 (br d, J=11.2 Hz, 1H), 4.15 (br d, J=7.0 Hz, 2H), 3.42 (br s, 2H), 2.46 (br s, 1H), 1.76-2.35 (m, 7H), 1.42 (br t, J=6.4 Hz, 5H), 1.26 (br d, J=5.2 Hz, 5H), 1.09 (br d, J=5.0 Hz, 3H).

Synthesis of Intermediate 7-3A

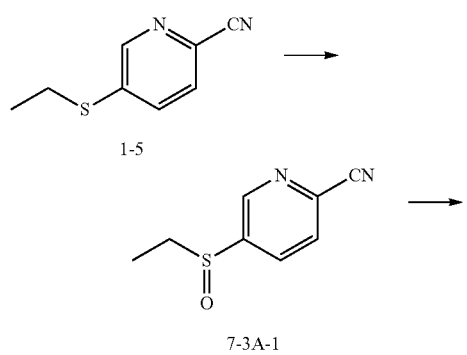

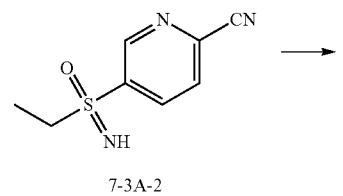

7-3A-2

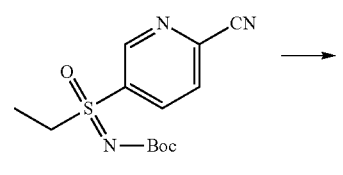

7-3A-3

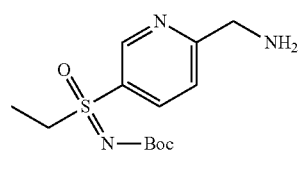

7-3A

Synthesis of Compound 7-3A-1

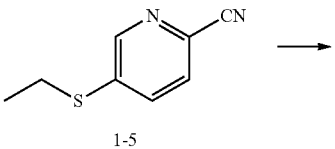

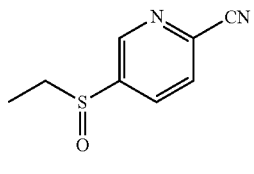

7-3A-1

At 0° C., periodic acid (18.00 g, 78.97 mmol, 1.08 eq) was added in portions to a suspension of Compound 1-5 (12 g, 73.07 mmol, 1 eq) and ferric trichloride (1.20 g, 7.40 mmol, 0.1 eq) in acetonitrile (100 mL). The reaction solution was stirred at 15° C. for 2 hours. When LC-MS showed the completion of the reaction, a saturated aqueous sodium sulfite solution (500 mL) was added to quench the reaction. The resulting aqueous phase was extracted three times with ethyl acetate (250 mL). The combined organic layers were washed with saturated brine (250 mL), dried over anhydrous sodium sulfate and filtered. The filtrate was concentrated under reduced pressure to obtain Compound 7-3A-1.

MS (ESI) m/z: 180.9 [M+H]$^+$;

$^1$H NMR (400 MHz, CHLOROFORM-d): δ 8.82 (d, J=1.6 Hz, 1H), 8.21 (dd, J=2.4, 8.0 Hz, 1H), 7.90 (d, J=8.0 Hz, 1H), 3.04-3.13 (m, 1H), 2.83-2.88 (m, 1H), 1.28 (t, J=7.2 Hz, 3H).

Synthesis of Compound 7-3A-2

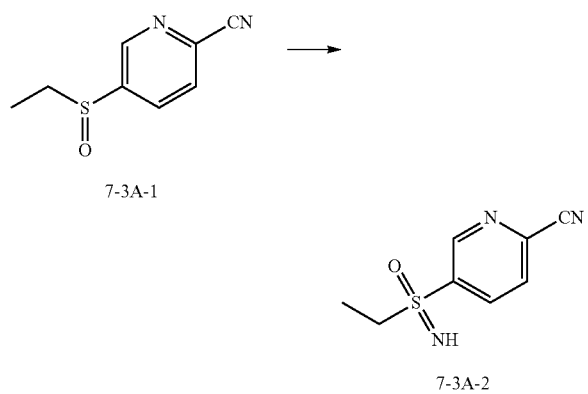

At 20° C., to a solution of Compound 7-3A-1 (6.5 g, 36.07 mmol, 1 eq) in methanol (50 mL), iodobenzene diacetate (35.21 g, 109.31 mmol, 3.03 eq) and ammonium carbamate (11.38 g, 145.70 mmol, 4.04 eq) were added in portions, and the reaction solution was stirred at 15° C. for 2 hours. When thin-layer chromatography and LC-MS showed the completion of the reaction, the reaction solution was directly concentrated and dried by rotary evaporation. The residue was subjected to column separation using a flash purification system (SepaFlash® silica gel flash column (40 g), eluent: petroleum ether/ethyl acetate; elution gradient: ethyl acetate/petroleum ether (V/V)=0% to 100%; flow rate: 50 mL/min) and purified to obtain Compound 7-3A-2.

MS (ESI) m/z: 195.9 [M+H]$^+$;

$^1$H NMR (400 MHz, CHLOROFORM-d): δ 9.22 (d, J=2.0 Hz, 1H), 8.41 (dd, J=2.4, 8.0 Hz, 1H), 7.90 (d, J=8.0 Hz, 1H), 3.21-3.27 (m, 2H), 1.30 (t, J=7.2 Hz, 3H).

Synthesis of Compound 7-3A-3

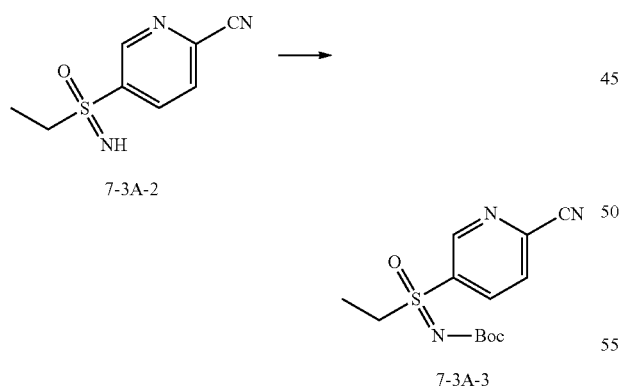

At 15° C., to a solution of Compound 7-3A-2 (2 g, 10.24 mmol, 1 eq) in tetrahydrofuran (20 mL), sodium hydride (600.00 mg, 15.00 mmol, purity: 60%, 1.46 eq) was added in portions, and the reaction solution was stirred at 15° C. for 0.5 hours. Boc$_2$O (4.47 g, 20.46 mmol, 4.70 mL, 2 eq) was added to the reaction solution in portions, and the reaction solution was stirred at 15° C. for 16 hours. When the thin-layer chromatography and LC-MS showed the completion of the reaction, water (150 mL) was added to the reaction solution to quench the reaction. The resulting aqueous phase was extracted three times with ethyl acetate (100 mL). The combined organic layers were washed with saturated brine (100 mL), dried over anhydrous sodium sulfate and filtered, and the filtrate was concentrated under reduced pressure. The residue was subjected to column separation and purification using a flash purification system (SepaFlash® silica gel flash column (40 g), eluent: petroleum ether/ethyl acetate; elution gradient: ethyl acetate/petroleum ether (V/V)=0% to 30%; flow rate: 50 mL/min), and Compound 7-3A-3 was obtained.

MS (ESI) m/z: 195.9 [M−100+H]$^+$, 239.9 [M−56+H]$^+$;

$^1$H NMR (400 MHz, CHLOROFORM-d): δ 9.17 (d, J=2.0 Hz, 1H), 8.41 (dd, J=2.4, 8.0 Hz, 1H), 7.95 (d, J=8.0 Hz, 1H), 3.35-3.53 (m, 2H), 1.40 (s, 9H) 1.35 (t, J=7.2 Hz, 3H).

Synthesis of Intermediate 7-3A

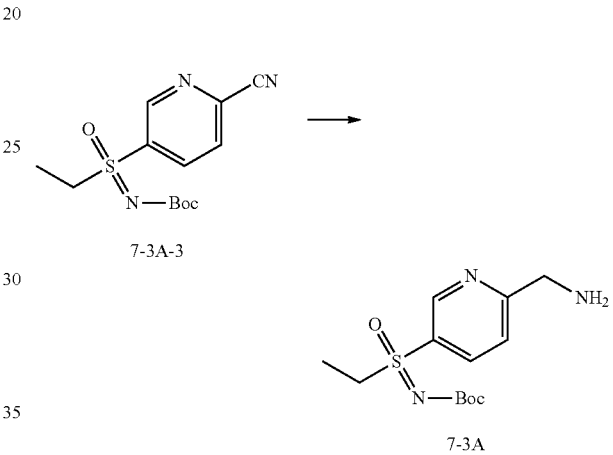

In a nitrogen atmosphere, Pd/C (10%, 200 mg) was added to a solution of Compound 7-3A-3 (500 mg, 1.70 mmol, 1 eq) in 15 mL methanol. The reaction solution was purged with hydrogen gas for three times, and then stirred at 20 to 30° C. for 5 hours in a hydrogen atmosphere (hydrogen balloon). LC-MS showed that Compound 7-3A-3 was completely consumed and the formation of the product was detected. The reaction solution was filtered through celite and then concentrated under reduced pressure to give a crude product of Compound 7-3A. The crude product was used directly in the next step without purification.

MS (ESI) m/z: 243.9 [M−56+H]$^+$.

Example 9

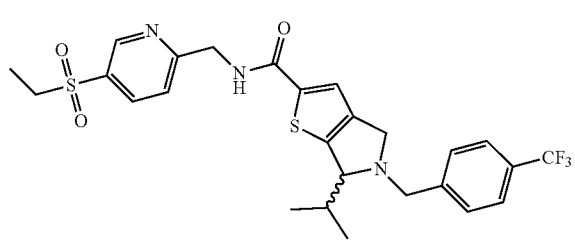 [SMILES: CCS(=O)(=O)c1ccc(CNC(=O)c2cc3c(s2)C(C(C)C)N(Cc2ccc(C(F)(F)F)cc2)C3)nc1]

The preparation method of Example 9 was the same as that of Example 1, except that Compound 1-3 was replaced with 4-trifluoromethylbenzaldehyde in the last step of Example 9 to obtain Example 9.

MS (ESI) m/z: 552.3 [M+H]⁺;

¹H NMR (400 MHz, CHLOROFORM-d): δ 8.95 (d, J=1.2 Hz, 1H), 8.08 (dd, J=2.2, 8.2 Hz, 1H), 7.50-7.56 (m, 2H), 7.40-7.49 (m, 3H), 7.22 (s, 1H), 7.12 (br t, J=5.0 Hz, 1H), 4.75 (d, J=5.2 Hz, 2H), 4.14 (br d, J=14.0 Hz, 1H), 3.90-4.08 (m, 2H), 3.75 (d, J=14.0 Hz, 1H), 3.42 (dd, J=2.8, 12.42 Hz, 1H), 3.08 (q, J=7.2 Hz, 2H), 1.95 (qd, J=6.8, 10.8 Hz, 1H), 1.24 (t, J=7.4 Hz, 3H), 1.04 (d, J=6.8 Hz, 3H), 0.87 (d, J=6.8 Hz, 3H).

Example 10 and Example 11

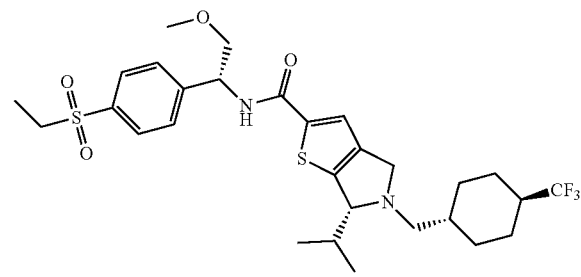

Example 10 or Example 11

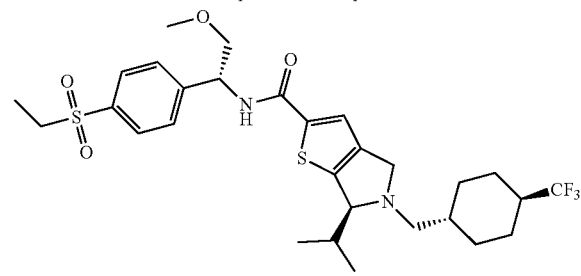

Example 10 or Example 11

The preparation methods of Example 10 and Example 11 were the same as that of Example 1, except that Example 10 and Example 11 employed Compound 10-1, i.e., (R)-1-(4-(ethylsulfonyl)phenyl)-2-methoxyethylamine in lieu of Compound 1-7 in the synthetic step of Compound 1-19 in Example 1, while the remaining steps were the same. Example 10 and Example 11 were obtained by SFC separation.

Example 10

The retention time Rt of the SFC analysis was 1.479 min. The SFC analysis conditions were as follows: (column: Chiralcel OD-3 50 mm×4.6 mm, I.D. 3 μm); mobile phase: phase A was supercritical fluid carbon dioxide, and phase B was isopropanol containing 0.05% diethylamine; gradient: the volume ratio of mobile phase B was kept at 5% for 0.2 minutes, increased from 5% to 40% within 1.4 minutes, kept at 40% for 1.05 minutes, and then kept at 5% for 0.35 minutes; flow rate: 4 mL/min; column temperature: 40° C.

MS (ESI) m/z: 601.0 [M+H]⁺;

¹H NMR (400 MHz, CHLOROFORM-d): δ 7.87 (d, J=8.0 Hz, 2H), 7.58 (d, J=8.6 Hz, 2H), 7.32 (s, 1H), 6.76 (d, J=7.0 Hz, 1H), 5.30-5.37 (m, 1H), 4.18 (dd, J=3.8, 12.4 Hz, 1H), 3.93 (br d, J=3.6 Hz, 1H), 3.75-3.80 (m, 1H), 3.69-3.74 (m, 1H), 3.47 (dd, J=3.6, 12.0 Hz, 1H), 3.38 (s, 3H), 3.09 (q, J=7.6 Hz, 2H), 2.92 (t, J=11.8 Hz, 1H), 2.44-2.51 (m, 1H), 2.10 (br s, 1H), 1.87-1.98 (m, 4H), 1.69 (br s, 2H), 1.59 (br s, 2H), 1.48-1.53 (m, 2H), 1.28 (t, J=7.6 Hz, 3H), 1.10 (d, J=7.0 Hz, 3H), 0.82 (d, J=7.0 Hz, 3H).

Example 11

The retention time Rt of the SFC analysis was 1.748 min. The SFC analysis conditions were as follows: (column: Chiralcel OD-3 50 mm×4.6 mm, I.D. 3 μm); mobile phase: phase A was supercritical fluid carbon dioxide, and phase B was isopropanol containing 0.05% diethylamine; gradient: the volume ratio of mobile phase B was kept at 5% for 0.2 minutes, increased from 5% to 40% within 1.4 minutes, kept at 40% for 1.05 minutes, and then kept at 5% for 0.35 minutes; flow rate: 4 mL/min; column temperature: 40° C.

MS (ESI) m/z: 601.0 [M+H]⁺;

¹H NMR (400 MHz, CHLOROFORM-d): δ 7.86 (d, J=8.6 Hz, 2H), 7.58 (d, J=8.0 Hz, 2H), 7.31 (s, 1H), 6.77 (d, J=7.0 Hz, 1H), 5.29-5.39 (m, 1H), 4.20 (br d, J=12.0 Hz, 1H), 3.89 (br d, J=3.0 Hz, 1H), 3.75-3.81 (m, 1H), 3.68-3.74 (m, 1H), 3.49 (dd, J=3.0, 12.6 Hz, 1H), 3.38 (s, 3H), 3.09 (q, J=7.6 Hz, 2H), 2.50-2.64 (m, 2H), 2.22 (br d, J=14.6 Hz, 1H), 1.77-2.06 (m, 5H), 1.44 (br s, 1H), 1.29-1.38 (m, 2H), 1.24-1.29 (m, 3H), 1.06 (d, J=7.0 Hz, 3H), 0.85-1.02 (m, 2H), 0.82 (d, J=7.0 Hz, 3H).

Preparation of Intermediate 10-1 (i.e., (R)-1-(4-(ethylsulfonyl)phenyl)-2-methoxyethylamine)

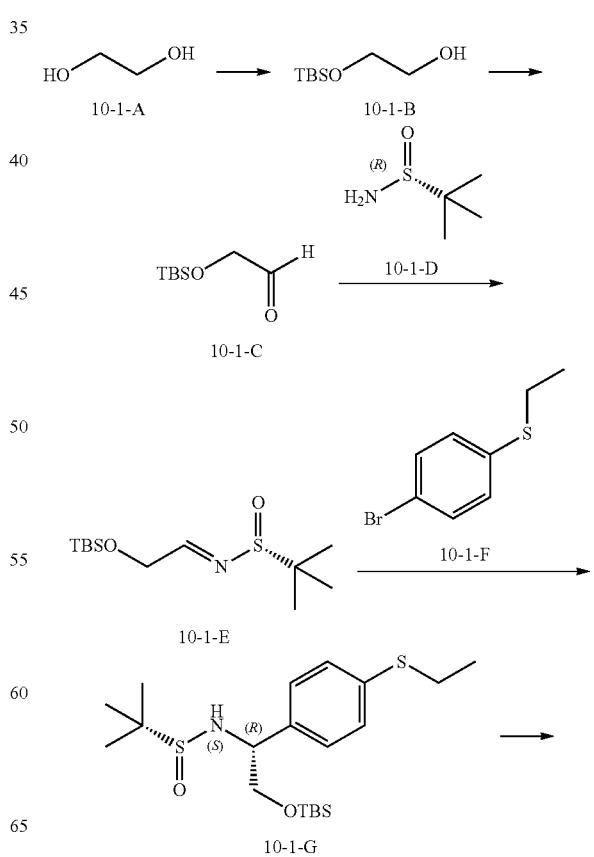

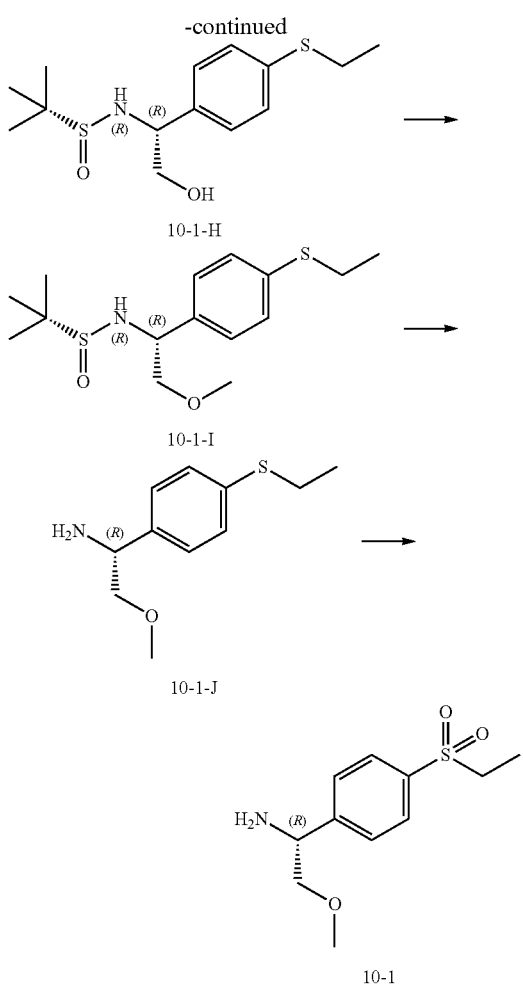

Synthesis of Intermediate 10-1-B

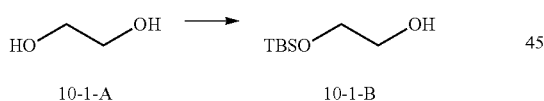

At 25 to 30° C., triethylamine (195.63 g, 1.93 mol, 267.99 mL, 1.20 eq) was added to a solution of Compound 10-1-A (100.00 g, 1.61 mol, 90.09 mL, 1.00 eq) in 1 L anhydrous dichloromethane. After the resulting mixture was cooled down to 0° C., TBSCl (242.82 g, 1.61 mol, 197.41 mL, 1.00 eq) dissolved in 300 mL dichloromethane was added dropwise within one hour. The reaction solution was stirred at 25 to 35° C. for 18 hours. The reaction solution was added with 400 mL saturated ammonium chloride solution to quench the reaction, and then subjected to liquid-liquid separation. The aqueous phase was extracted twice with 800 mL methyl tert-butyl ether, and the combined organic phases were concentrated under reduced pressure and then dissolved with 400 mL methyl tert-butyl ether. The methyl tert-butyl ether phase was washed twice with 1,000 mL water, and then washed with 500 mL saturated brine, dried over anhydrous sodium sulfate, and concentrated under reduced pressure to give a yellow liquid. The resulting Compound 10-1-B was directly used in the next step. $^1$H NMR (400 MHz, CHLOROFORM-d) δ=3.61-3.64 (m, 2H), 3.56 (br d, J=4.4 Hz, 2H), 2.17 (br s, 1H), 0.82-0.83 (m, 9H), 0.00 (s, 6H).

Synthesis of Intermediate 10-1-C

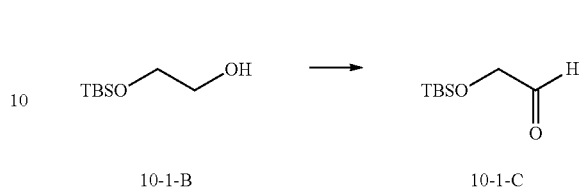

After 500 mL solution of dichloromethane was cooled down to −30° C., (COCl)$_2$ (39.59 g, 311.92 mmol, 27.30 mL, 1.10 eq) was added dropwise. After the completion of the dropwise addition, the reaction solution was cooled down to −70° C., and DMSO (48.74 g, 623.83 mmol, 44.31 mL, 2.20 eq) was added dropwise. After the completion of the addition, the reaction solution was stirred at the same temperature for 30 min. At the same temperature, 100 mL dichloromethane in which Compound 10-1-B (50.00 g, 283.56 mmol, 1.00 eq) was dissolved was slowly added dropwise to the reaction system. After the reaction solution was stirred at −70° C. for one hour, Et$_3$N (143.47 g, 1.42 mol, 196.53 mL, 5.00 eq) was added dropwise. The reaction solution was stirred at −70° C. for 30 minutes, and then heated to 25 to 35° C. and reacted for 16 hours. TLC showed that Compound 10-1-B was completely consumed and a new spot was formed. The reaction solution was washed with 500 mL water, then washed twice with 1000 mL of 1 mol/L hydrochloric acid, and washed again with 500 mL of saturated sodium bicarbonate solution and 500 mL of saturated brine. The organic phase was dried over anhydrous sodium sulfate, filtered, and concentrated to give Compound 10-1-C, which was used directly in the next step.

$^1$H NMR (400 MHz, CHLOROFORM-d) δ 9.64 (s, 1H), 4.15 (s, 2H), 0.87 (s, 9H), 0.04 (s, 6H).

Synthesis of Intermediate 10-1-E

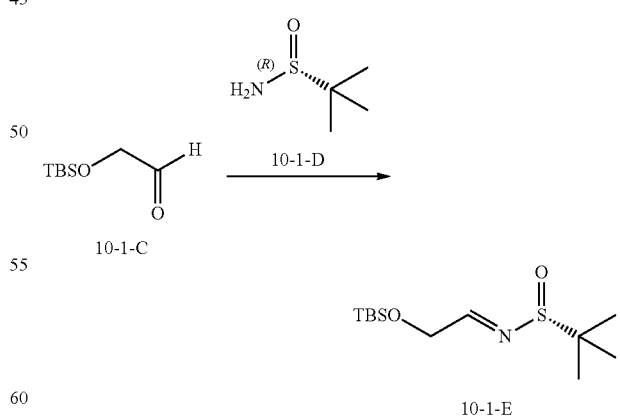

A solution (1.50 L) of Compound 10-1-C (102.00 g, 585.16 mmol, 1.00 eq), Compound 10-1-D (70.92 g, 585.16 mmol, 1.00 eq) and CuSO$_4$ (233.50 g, 1.46 mol, 224.52 mL, 2.50 eq) in anhydrous dichloromethane was stirred at 25 to 35° C. for 16 hours. TLC showed that Compound 10-1-C was completely consumed and a major spot appeared. The reaction solution was quenched with 1000 mL water and subjected to liquid-liquid separation. The aqueous phase was extracted twice with 2000 mL dichloromethane. The combined organic phases were washed once with 1000 mL water and 1000 mL saturated brine, dried over anhydrous sodium sulfate, filtered, and concentrated. The crude product was allowed to pass through a flash column (ISCO®; SepaFlash® silica gel flash column (220 g), eluent: ethyl acetate and petroleum ether; elution gradient: 0% to 20%; flow rate: 100 mL/min) in three portions and was purified to give Compound 10-1-E.

MS (ESI) m/z: 278.1 [M+H]$^+$;

$^1$H NMR (400 MHz, CHLOROFORM-d) δ 7.96 (t, J=3.2 Hz, 1H), 4.44 (d, J=3.0 Hz, 2H), 1.11 (s, 9H), 0.82 (s, 9H), 0.00 (s, 6H).

Synthesis of Intermediate 10-1-G

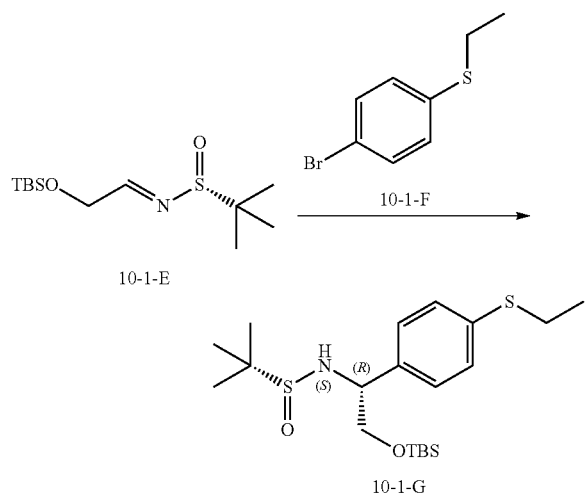

At −65° C., n-BuLi (2.5 M, 63.42 mL, 2.20 eq) was added dropwise to a solution of Compound 10-1-F (31.30 g, 144.14 mmol, 2.00 eq) in 150 mL anhydrous tetrahydrofuran. After the completion of the dropwise addition, the reaction solution was stirred at the same temperature for half an hour. A solution of Compound 10-1-E (20.00 g, 72.07 mmol, 1.00 eq) in 50 mL anhydrous tetrahydrofuran was added dropwise to the reaction solution at −65° C. Upon the completion of the dropwise addition, the reaction solution was stirred at the same temperature for 2 hours, and then heated to 30° C. and stirred for 2 hours. LC-MS showed that Compound 10-1-E was completely consumed and there was a main peak showing the MS of the product. The reaction solution was quenched with 200 mL saturated ammonium chloride solution and then extracted twice with 200 mL ethyl acetate. The combined organic phases were washed sequentially with 200 mL of water and saturated brine, dried over anhydrous sodium sulfate, filtered, and concentrated to give a crude product. The crude product was purified by a flash column (ISCO®; SepaFlash® silica gel flash column (120 g), eluent: ethyl acetate and petroleum ether; elution gradient: 0% to 20%; flow rate: 80 mL/min) to obtain Compound 10-1-G.

MS (ESI) m/z: 438.2 [M+Na]$^+$;

$^1$H NMR (400 MHz, CHLOROFORM-d) δ=7.15-7.23 (m, 4H), 4.42 (m, 1H), 4.19 (s, 1H), 3.67-3.71 (m, 1H), 3.49-3.55 (m, 1H), 2.88 (q, J=7.4 Hz, 2H), 1.25 (t, J=7.4 Hz, 3H), 1.14-1.17 (m, 9H), 0.83 (s, 9H), −0.01 (d, J=7.6 Hz, 6H).

Synthesis of Intermediate 10-1-H

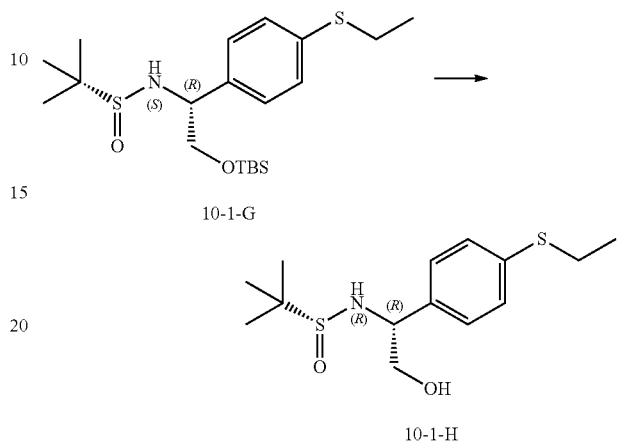

To a solution of Compound 10-1-G (2.00 g, 4.81 mmol, 1.00 eq) in 30 mL tetrahydrofuran was added TBAF (2.52 g, 9.62 mmol, 2.00 eq). The reaction solution was stirred for 1 hour at 20 to 25° C. TLC showed that Compound 10-1-G was completely consumed and a new spot was generated. The reaction solution was washed with 15 mL of a saturated sodium bicarbonate solution and 15 mL of a saturated saline solution, dried over anhydrous sodium sulfate, filtered, and concentrated under reduced pressure to give a crude product as an oil. The crude product was purified by a flash column (ISCO®; SepaFlash® silica gel flash column (20 g), eluent: ethyl acetate and petroleum ether; elution gradient: 0% to 100%; flow rate: 35 mL/min) to obtain Compound 10-1-H.

MS (ESI) m/z: 324.0 [M+Na]$^+$;

$^1$H NMR (400 MHz, DMSO-d6) δ=7.21-7.28 (m, 4H), 5.04 (t, J=5.8 Hz, 1H), 4.95 (d, J=4.0 Hz, 1H), 4.20-4.25 (m, 1H), 3.52 (t, J=6.2 Hz, 2H), 2.94 (q, J=7.4 Hz, 2H), 1.21 (t, J=7.4 Hz, 3H), 1.10 (s, 9H).

Synthesis of Intermediate 10-1-I

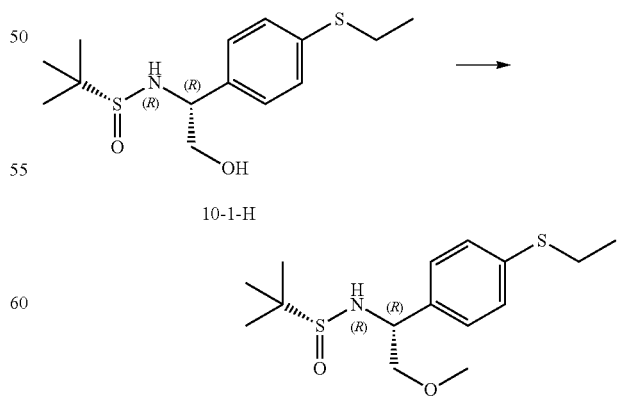

At 0° C., NaH (199.02 mg, 4.98 mmol, purity: 60%, 1.50 eq) was added to a solution of Compound 10-1-H (1.00 g, 3.32 mmol, 1.00 eq) in 30 mL tetrahydrofuran, and then the resulting mixture was stirred for half an hour. Iodomethane (990.00 mg, 6.97 mmol, 434.21 μL, 2.10 eq) was added dropwise, and then the reaction solution was stirred at 20 to 25° C. for 15.5 h. LC-MS showed that Compound 10-1-H was completely consumed. The reaction solution was dispersed in 30 mL water and 30 mL ethyl acetate, and was subjected to liquid-liquid separation. The organic phases were washed with 30 mL saturated brine, dried over anhydrous sodium sulfate, filtered, and concentrated under reduced pressure to obtain a residue. The crude product was purified by a flash column (ISCO®; SepaFlash® silica gel flash column (60 g), eluent: ethyl acetate and petroleum ether; elution gradient: 0% to 100%; flow rate: 40 mL/min) to obtain Compound 10-1-I.

$^1$H NMR (400 MHz, CHLOROFORM-d) δ=7.16-7.23 (m, 4H), 4.51-4.60 (m, 1H), 4.02 (s, 1H), 3.42-3.46 (m, 2H), 3.32 (s, 3H), 2.88 (q, J=7.45 Hz, 2H), 1.25 (t, J=7.28 Hz, 3H), 1.15 (s, 9H)

Synthesis of Intermediate 10-1-J

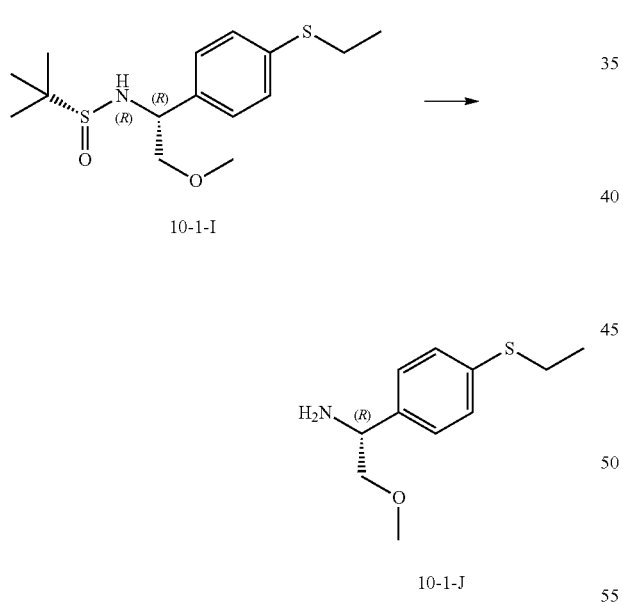

A solution of Compound 10-1-I (800.00 mg, 2.54 mmol, 1.00 eq) in HCl/dioxane (2.54 mmol, 4.00 mL, 1.00 eq) was stirred at 20 to 25° C. for 2 hours. LC-MS showed that Compound 10-1-I was completely consumed. The reaction solution was concentrated under reduced pressure to remove the solvent, so as to obtain a crude product of Compound 10-1-J, which was directly used in the next step without purification.

MS (ESI) m/z: 194.9 [M-NH$_2$]$^+$;

Synthesis of Intermediate 10-1

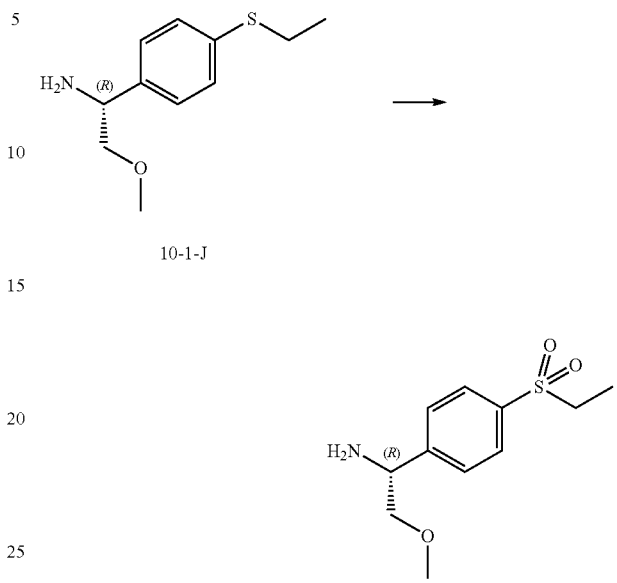

Oxone (4.07 g, 6.63 mmol, 2.00 eq) was added to 30 mL aqueous solution of Compound 10-1-J (700.00 mg, 3.31 mmol, 1.00 eq). The reaction solution was stirred at 20 to 25° C. for 2 hours. LC-MS showed that Compound 10-1-J was completely consumed and MS of Compound 10-1 appeared. The reaction solution was directly lyophilized, and the crude product was purified by a flash column (ISCO®; SepaFlash® silica gel flash column (4 g), eluent: dichloromethane and methanol; elution gradient: 0% to 10%; flow rate: 18 mL/min) to obtain Compound 10-1-I.

MS (ESI) m/z: 244.0 [M+H]$^+$;

$^1$H NMR (400 MHz, CHLOROFORM-d) δ ppm 7.91 (d, J=7.6 Hz, 2H), 7.69 (d, J=7.8 Hz, 2H), 4.57 (br s, 1H), 3.75 (br d, J=5.8 Hz, 2H), 3.35-3.45 (m, 5H), 3.12 (q, J=7.2 Hz, 2H), 1.25 (t, J=7.4 Hz, 3H).

Example 12 and Example 13

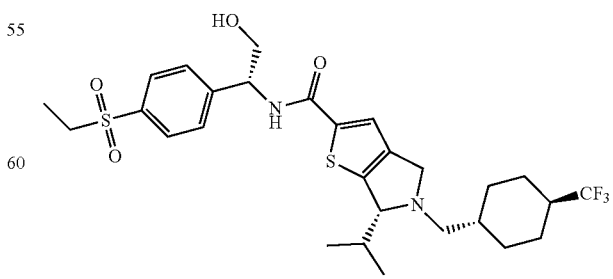

Example 12 or Example 13

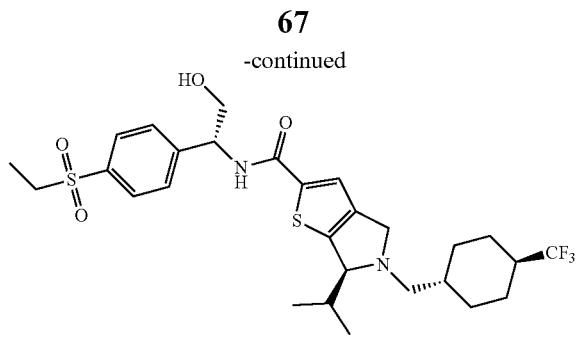

Example 12 or Example 13

The preparation methods of Example 12 and Example 13 were the same as that of Example 1, except that Example 12 and Example 13 employed Compound 12-1, i.e., (R)-2-amino-(4-(ethylsulfonyl)phenyl)ethanol in lieu of Compound 1-7 in the synthetic step of Compound 1-19 in Example 1, while the remaining steps were the same. Example 12 and Example 13 were obtained by SFC separation.

Example 12

The retention time Rt of the SFC analysis was 2.963 min. The SFC analysis conditions were as follows: (column: Chiralpak AS-H 150 mm×4.6 mm, I.D. 5 μm); mobile phase: phase A was supercritical fluid carbon dioxide, and phase B was methanol containing 0.05% diethylamine; gradient: the volume ratio of mobile phase B was kept at 5% for 0.5 minutes, increased from 5% to 40% within 3.5 minutes, kept at 40% for 2.5 minutes, and then kept at 5% for 1.5 minutes; flow rate: 3 mL/min; column temperature: 40° C.

MS (ESI) m/z: 587.0 [M+H]+;

1HNMR (400 MHz, CHLOROFORM-d): δ 7.82 (br d, J=8.6 Hz, 2H), 7.51 (d, J=8.6 Hz, 2H), 7.27 (s, 1H), 6.74 (br s, 1H), 5.20 (br s, 1H), 4.12 (br d, J=12.6 Hz, 1H), 3.96 (br d, J=15.0 Hz, 2H), 3.82 (br s, 1H), 3.42 (br d, J=12.0 Hz, 1H), 3.03 (q, J=7.6 Hz, 2H), 2.43-2.59 (m, 2H), 2.15 (br d, J=14.0 Hz, 1H), 1.92 (br d, J=10.6 Hz, 3H), 1.72-1.87 (m, 2H), 1.24-1.43 (m, 1H), 1.22 (t, J=7.6 Hz, 4H), 1.00 (d, J=7.0 Hz, 3H), 0.78-0.94 (m, 2H), 0.76 (d, J=6.6 Hz, 3H).

Example 13

The retention time Rt of the SFC analysis was 3.342 min. The SFC analysis conditions were as follows: (column: Chiralpak AS-H 150 mm×4.6 mm, I.D. 5 μm); mobile phase: phase A was supercritical fluid carbon dioxide, and phase B was methanol containing 0.05% diethylamine; gradient: the volume ratio of mobile phase B was kept at 5% for 0.5 minutes, increased from 5% to 40% within 3.5 minutes, kept at 40% for 2.5 minutes, and then kept at 5% for 1.5 minutes; flow rate: 3 mL/min; column temperature: 40° C.

MS (ESI) m/z: 587.0 [M+H]+;

1H NMR (400 MHz, CHLOROFORM-d): δ 7.89 (br d, J=7.6 Hz, 2H), 7.58 (br d, J=8.0 Hz, 2H), 7.34 (s, 1H), 6.82 (br s, 1H), 5.28 (br s, 1H), 4.20 (br d, J=14.6 Hz, 1H), 4.03 (br d, J=19.0 Hz, 2H), 3.89 (br s, 1H), 3.49 (br d, J=10.6 Hz, 1H), 3.10 (br d, J=7.0 Hz, 2H), 2.47-2.66 (m, 2H), 2.22 (br d, J=13.6 Hz, 1H), 1.98 (br d, J=10.6 Hz, 3H), 1.77-1.92 (m, 2H), 1.25-1.30 (m, 6H), 1.06 (br d, J=7.0 Hz, 3H), 0.82 (br d, J=6.6 Hz, 4H).

Preparation of the Intermediate (R)-2-amino-(4-(ethylsulfonyl)phenyl)ethanol

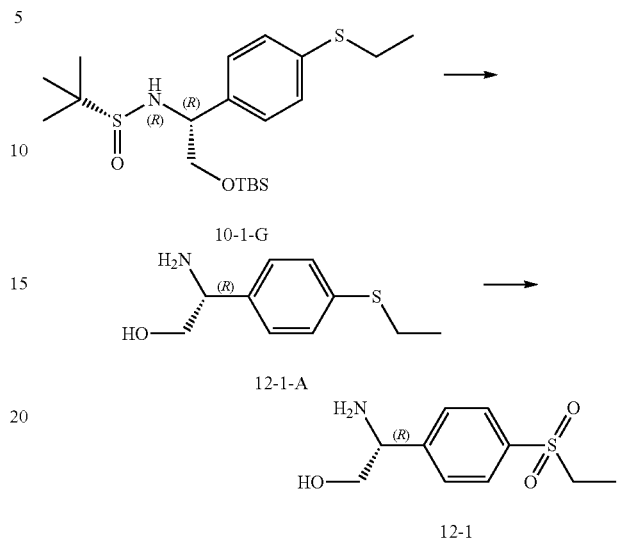

Synthesis of Intermediate 12-1-1A

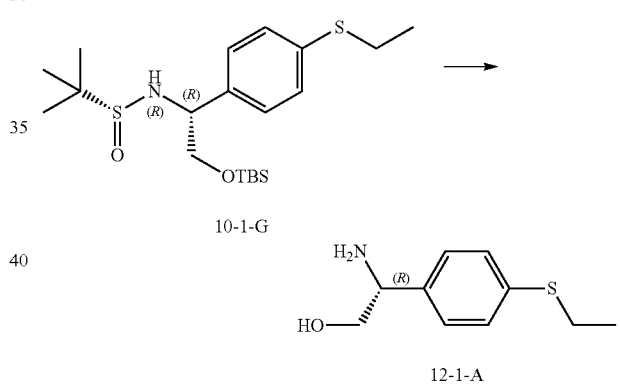

At 0° C., to a solution of Compound 10-1-G (400.00 mg, 962.16 μmol, 1.00 eq) in 70 mL dichloromethane was added HCl/dioxane (4 M, 481.08 μL, 2.00 eq). The reaction solution was stirred at 20 to 25° C. for 1.5 hours. LC-MS showed that Compound 10-1-G was completely consumed and MS of Compound 12-1-A was obtained. After the solvent was removed from the reaction solution under reduced pressure, Compound 12-1-A was obtained and was directly used in the next step without further purification.

MS (ESI) m/z: 180.8 [M+H]+;

Synthesis of Intermediate 12-1

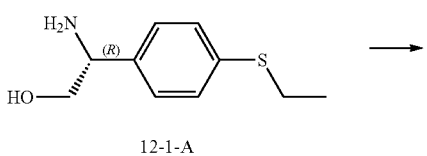

-continued

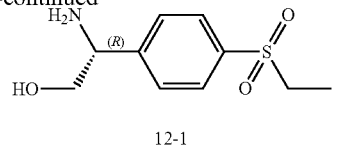

12-1

At 0° C., an aqueous solution of Oxone (1.18 g, 1.92 mmol, 2.00 eq) in 2 mL H₂O (2.00 mL) was added dropwise to a solution of Compound 12-1-1A (224.91 mg, 962.14 µmol, 1.00 eq, HCl) in 2 mL MeOH. After the mixture was stirred at 20 to 25° C. for one hour, the completion of the reaction was monitored by LC-MS. The reaction solution was filtered. The filtrate was quenched with 30 mL saturated sodium thiosulfate solution, and then concentrated under reduced pressure to give a crude product. After the crude product was dissolved in a solution of CH₂Cl₂:MeOH (3:1, 20 mL), the mixture was stirred for 30 min, filtered, and concentrated under reduced pressure to obtain Compound 12-1, which was directly used in the next step without further purification.

MS (ESI) m/z: 213.0 [M-NH$_2$]$^+$;

$^1$HNMR (400 MHz, DEUTERIUM OXIDE) δ=7.93 (d, J=8.6 Hz, 2H), 7.65 (d, J=8.6 Hz, 2H), 4.56 (dd, J=7.0, 4.8 Hz, 1H), 3.81-3.97 (m, 2H), 3.30 (q, J=7.2 Hz, 2H), 1.13 (t, J=7.4 Hz, 3H).

Example 14 and Example 15

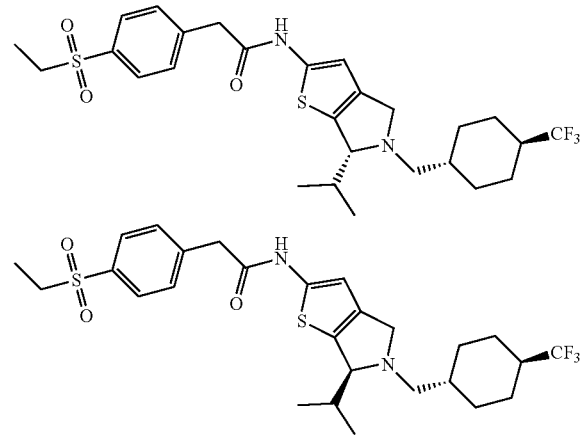

Example 14 or Example 15       Example 14 or Example 15

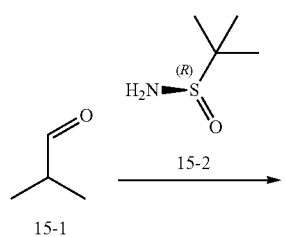

15-1

-continued

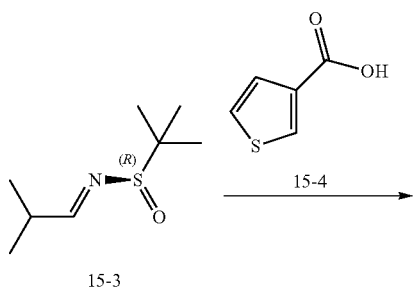

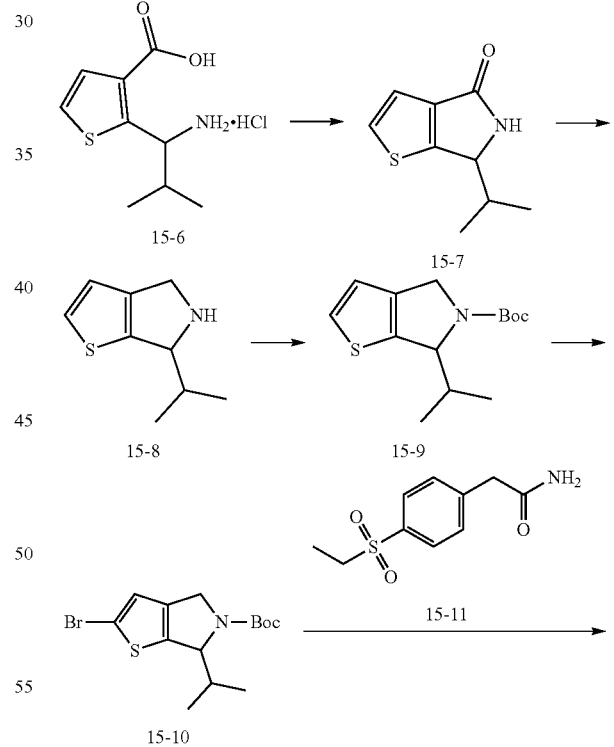

-continued

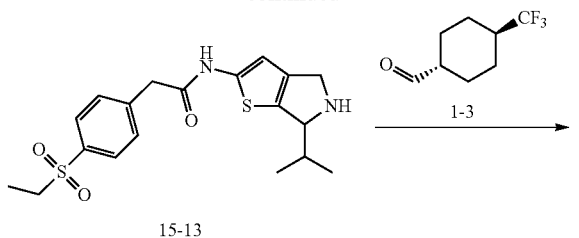

15-13

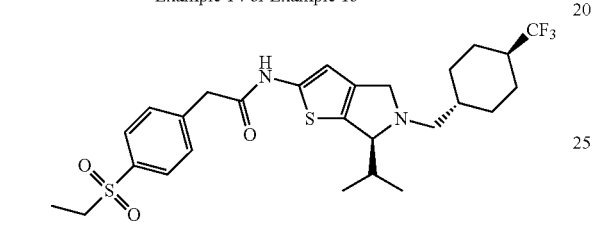

Example 14 or Example 15

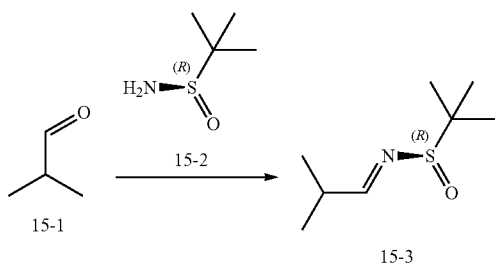

Example 14 or Example 15

Synthesis of Compound 15-3

Compound 15-2 (20 g, 165.02 mmol, 1 eq) was dissolved in anhydrous dichloromethane (300.00 mL), MgSO$_4$ (99.91 g, 830.03 mmol, 5.03 eq) and PPTS (4 g, 15.92 mmol, 0.096 eq) were sequentially added thereto, Compound 15-1 was added finally, and the reaction solution was stirred at 20° C. for 16 hours. When TLC showed that a spot was formed under UV light, the reaction solution was filtered through celite. After the filter cake was washed with dichloromethane, the resultant was combined with the filtrate, and the mixture was concentrated under reduced pressure to give a crude product. The crude product was purified by a flash column (SepaFlash® silica gel flash column (220 g), eluent: ethyl acetate and petroleum ether; elution gradient: ethyl acetate/petroleum ether (V/V)=0% to 100%, 0% to 30%; flow rate: 100 mL/min) to obtain Compound 15-3.

$^1$H NMR (400 MHz, CHLOROFORM-d): δ 7.92 (d, J=4.2 Hz, 1H), 1.12 (s, 9H), 1.11 (d, J=2.0 Hz, 3H), 1.10-1.10 (m, 1H), 1.09 (d, J=2.0 Hz, 3H).

Synthesis of Compound 15-5

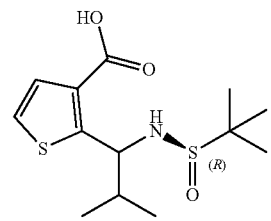

15-3

Compound 15-4 (5 g, 39.02 mmol, 1 eq) was dissolved in anhydrous THF (25 mL), to which LDA (2 M, 45.06 mL, 2.31 eq) was slowly added dropwise at 0° C. under the protection of nitrogen, and the mixture was stirred for 0.5 hours while the temperature was kept at −60° C. Then, a solution of Compound 15-3 (8.2 g, 46.8 mmol, 1.2 eq) in anhydrous THF (25 mL) was added dropwise to the above reaction solution within 1 hour. After the completion of the dropwise addition, the reaction solution was heated to 20° C. and then stirred for 1 hour. When LC-MS showed the completion of the reaction, water (100 mL) was added to quench the reaction, and an aqueous phase was obtained by separation. The resulting mixture was washed with ethyl acetate (100 mL), and then its pH was adjusted to 3 with hydrochloric acid (1 N, 20 mL), followed by extraction with ethyl acetate (150 mL×3). The combined organic layers were washed with saturated brine (80 mL), dried over anhydrous sodium sulfate, and filtered. The filtrate was concentrated under reduced pressure to obtain 10.3 g of a crude product of Compound 15-5. The crude product was diluted with 10 mL ethyl acetate. 70 mL petroleum ether was slowly added to the resulting suspension, and the suspension was stirred for half an hour and then filtered. The filter cake was slurried with a mixed solvent of 3 mL ethyl acetate and 20 mL petroleum ether, and the resultant was filtered and dried to obtain Compound 15-5.

MS (ESI) m/z: 303.9 [M+H]$^+$ $^1$H NMR (400 MHz, CHLOROFORM-d): δ 7.48 (d, J=5.2 Hz, 1H), 7.13 (d, J=5.2 Hz, 1H), 2.24-2.36 (m, 1H), 1.22 (s, 9H), 1.09 (br d, J=6.8 Hz, 3H), 0.91 (br d, J=6.2 Hz, 3H)

Synthesis of Compound 15-6

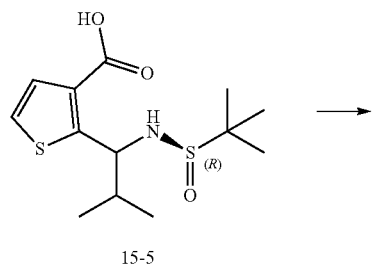

15-5

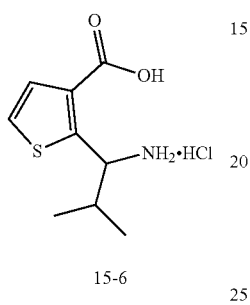

15-6

A solution of Compound 15-5 (5.1 g, 16.97 mmol, 1 eq) in hydrochloric acid-ethyl acetate (30 mL) was stirred at 28° C. for 1 hour. When LC-MS showed the completion of the reaction, the reaction solution was filtered to obtain Compound 15-6. The filter cake was slurried twice with 10 mL ethyl acetate. The resultant was filtered, dried, and directly used in the next step.

MS (ESI) m/z: 183 [M-NH$_2$]$^+$ $^1$H NMR (400 MHz, DMSO-d$_6$): δ 8.69 (br s, 3H), 7.68 (d, J=5.0 Hz, 1H), 7.40 (d, J=5.6 Hz, 1H), 5.21 (br dd, J=5.6, 9.6 Hz, 1H), 2.14-2.28 (m, 1H), 1.09 (d, J=6.6 Hz, 3H), 0.80 (d, J=7.0 Hz, 3H)

Synthesis of Compound 15-7

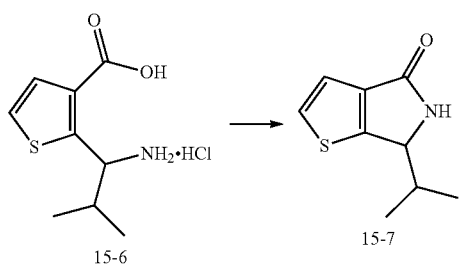

To a solution of Compound 15-6 (3.15 g, 13.36 mmol, 1 eq, HCl) in anhydrous dichloromethane (600.00 mL), HATU (7.62 g, 20.04 mmol, 1.5 eq) and TEA (4.06 g, 40.09 mmol, 5.58 mL, 3 eq) were added, and the mixture was stirred at 20° C. for 1 hour. When LC-MS showed the completion of the reaction, water (50.00 mL) was added for dilution and the resulting mixture was extracted with dichloromethane (200.00 mL×3). The combined organic layers were washed with saturated brine (100.00 mL), dried over anhydrous sodium sulfate, and filtered. The filtrate was concentrated under reduced pressure to give a crude product, which was purified by a flash column (SepaFlash® silica gel flash column (40 g), eluent: ethyl acetate and petroleum ether; elution gradient: 0% to 60%; flow rate: 35 mL/min) to obtain Compound 15-7.

MS (ESI) m/z: 182.0 [M+H]$^+$ $^1$H NMR (400 MHz, CHLOROFORM-d) δ 7.27 (d, J=5.0 Hz, 1H), 7.16-7.21 (m, 1H), 6.73 (br s, 1H), 4.45 (d, J=5.2 Hz, 1H), 1.92-2.07 (m, 1H), 0.96 (d, J=6.8 Hz, 3H), 0.89 (d, J=6.8 Hz, 3H).

Synthesis of Compound 15-8

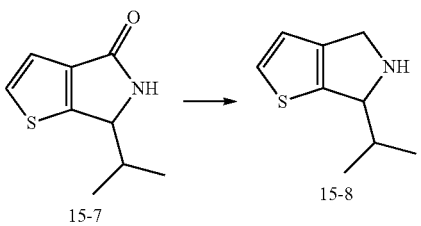

BH$_3$-Me$_2$S (10 M, 13.24 mL, 10 eq) was slowly added dropwise to a solution of Compound 15-7 (2.4 g, 13.24 mmol, 1 eq) in anhydrous tetrahydrofuran (30 mL) at room temperature, and the resulting mixture was stirred until the bubbles disappeared. Afterwards, the mixture was heated to 65° C. and reacted for 96 hours. When LC-MS showed the completion of the reaction, the reaction solution was cooled down to room temperature, and hydrochloric acid (2 N, 10 mL) was slowly added dropwise to quench the reaction. Thereafter, the reaction solution was washed with ethyl acetate (10 mL) and the aqueous phase was then separated. After the pH of the aqueous phase was adjusted to 8 with a saturated sodium bicarbonate solution, the mixture was extracted with ethyl acetate (40 mL×2). The combined organic layers were washed with water (10 mL), and then dried over anhydrous sodium sulfate and filtered. The filtrate was concentrated under reduced pressure to give a crude product. After the crude product was combined with another batch, they were purified by a flash column (SepaFlash® silica gel flash column (80 g), eluent: ethyl acetate and petroleum ether; elution gradient: 0% to 30%; flow rate: 50 mL/min) to obtain Compound 15-8.

MS (ESI) m/z: 167.9 [M+H]$^+$ $^1$H NMR (400 MHz, CHLOROFORM-d) δ 7.08-7.25 (m, 1H), 6.73 (d, J=4.8 Hz, 1H), 4.22 (td, J=2.8, 5.4 Hz, 1H), 4.03 (dd, J=3.2, 5.8 Hz, 2H), 1.81 (sxtd, J=6.6, 12.8 Hz, 1H), 0.92 (t, J=6.6 Hz, 6H).

Synthesis of Compound 15-9

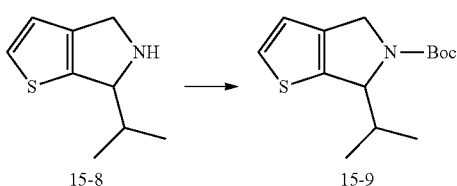 [SMILES: CC(C)C1NCc2ccsc21 ; CC(C)C1c2sccc2CN1C(=O)OC(C)(C)C]

To a solution of Compound 15-8 (5 g, 29.89 mmol, 1 eq) in anhydrous dichloromethane (50 mL), TEA (6.05 g, 59.78 mmol, 8.32 mL, 2 eq) and Boc anhydride (7.83 g, 35.87 mmol, 8.24 mL, 1.2 eq) were added, and the reaction solution was reacted at 20° C. for 1 hour. When LC-MS showed the completion of the reaction, the reaction solution was concentrated under reduced pressure to give a crude product, which was purified by a flash column (SepaFlash® silica gel flash column (40 g), eluent: ethyl acetate and petroleum ether, elution gradient: ethyl acetate/petroleum ether (v/v)=0% to 20%; flow rate: 35 mL/min) to obtain Compound 15-9.

MS (ESI) m/z: 211.9 [M-tert-butyl+H]$^+$ $^1$H NMR (400 MHz, CHLOROFORM-d) δ 7.17 (d, J=5.0 Hz, 1H), 6.78 (dd, J=4.8, 16.44 Hz, 1H), 4.81-4.98 (m, 1H), 4.43-4.60 (m, 1H), 4.33 (dd, J=3.8, 13.8 Hz, 1H), 2.27-2.59 (m, 1H), 1.43 (s, 9H), 0.98 (t, J=7.8 Hz, 3H), 0.54 (t, J=7.0 Hz, 3H).

Synthesis of Compound 15-10

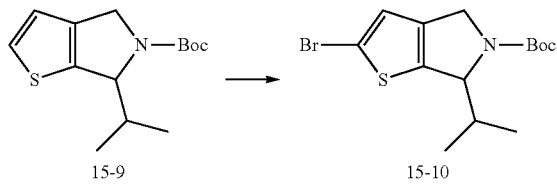 [SMILES: CC(C)C1c2sccc2CN1C(=O)OC(C)(C)C ; CC(C)C1c2sc(Br)cc2CN1C(=O)OC(C)(C)C]

To a solution of Compound 15-9 (1 g, 3.74 mmol, 1 eq) in acetonitrile (10 mL) was added NBS (732.21 mg, 4.11 mmol, 1.1 eq), and the reaction solution was stirred at 20° C. for 1 hour. When LC-MS showed the completion of the reaction, the reaction solution was concentrated under reduced pressure to obtain a crude product, which was purified by a flash column (SepaFlash® silica gel flash column (4 g), eluent: ethyl acetate and petroleum ether, elution gradient: 0% to 10%; flow rate: 18 mL/min) to obtain Compound 15-10.

MS (ESI) m/z: 291.9 [M-tert-butyl+H]$^+$ $^1$H NMR (400 MHz, CHLOROFORM-d) δ 6.79 (d, J=18.8 Hz, 1H), 4.76-4.95 (m, 1H), 4.25-4.60 (m, 2H), 2.21-2.57 (m, 1H), 1.43 (s, 9H), 0.94 (t, J=7.0 Hz, 3H), 0.56 (t, J=7.2 Hz, 3H).

Synthesis of Compound 15-12

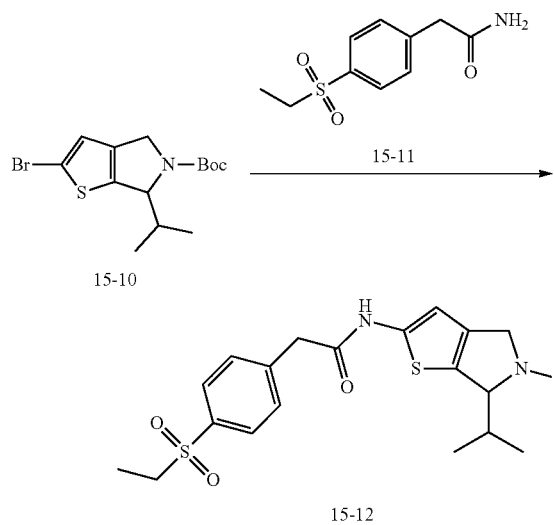

A mixed solution of Compound 15-10 (0.3 g, 1.32 mmol, 1 eq), Compound 15-11 (548.49 mg, 1.58 mmol, 1.2 eq), CuI (251.39 mg, 1.32 mmol, 1 eq) and K$_3$PO$_4$ (560.37 mg, 2.64 mmol, 2 eq) in anhydrous dioxane (10 mL) was purged three times with nitrogen, N,N-diisopropylethylamine (127.99 mg, 1.45 mmol, 156.28 μL, 1.1 eq) was then added thereto under nitrogen protection, and the reaction solution was stirred at 100° C. for 1.5 hours. When LC-MS showed the completion of the reaction, the reaction solution was concentrated under reduced pressure to remove dioxane, and then diluted with water (10 mL). The resulting mixture was extracted with dichloromethane (15 mL×3). The combined organic layers were washed with saturated brine (20 mL), dried over anhydrous sodium sulfate, and filtered. The filtrate was concentrated under reduced pressure to obtain a crude product, which was prepared and purified by thin-layer chromatography (SiO$_2$, PE:EA=1:1) to obtain Compound 15-12.

MS (ESI) m/z: 393.0 [M-Boc+H]$^+$ $^1$H NMR (CHLOROFORM-d) δ: 7.86 (d, J=8.0 Hz, 2H), 7.53 (br d, J=8.0 Hz, 2H), 6.45 (d, J=16.4 Hz, 1H), 4.85-5.01 (m, 1H), 4.50 (t, J=14.8 Hz, 1H), 4.33 (td, J=13.2, 3.6 Hz, 1H), 3.80-3.84 (m, 2H), 3.69-3.77 (m, 2H), 3.12 (q, J=7.6 Hz, 2H), 2.29-2.62 (m, 1H), 1.50 (d, J=3.6 Hz, 9H), 1.28-1.32 (m, 3H), 0.96-1.05 (m, 3H), 0.52-0.65 (m, 3H).

Synthesis of Intermediate 15-11

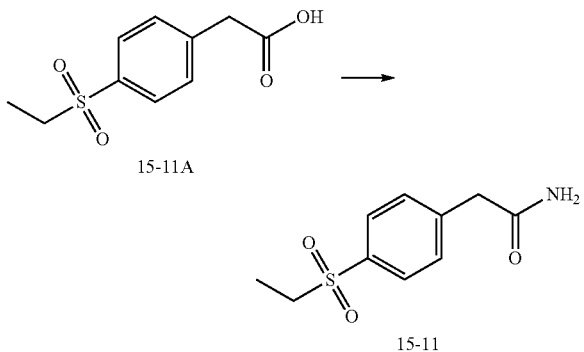

A solution of Compound 15-11A (1 g, 4.38 mmol, 1 eq) in SOCl$_2$ (16.40 g, 137.85 mmol, 10 mL, 31.47 eq) was stirred at 20° C. for 2 hours, and then concentrated under reduced pressure to remove SOCl$_2$ and dissolved in anhydrous dichloromethane (20 mL), aqueous ammonia (9.10 g, 64.92 mmol, 10 mL, purity: 25%, 14.82 eq) was added thereto, and the reaction solution was stirred at 20° C. for 3 hours. When LC-MS showed the completion of the reaction, the mixture was diluted with water (10 mL) and extracted with dichloromethane (10 mL×3). The combined organic layers were washed with saturated brine (20 mL), dried over anhydrous sodium sulfate, and filtered. The filtrate was concentrated under reduced pressure to give Intermediate 15-11.

MS (ESI) m/z: 228.0 [M-Boc+H]$^+$ $^1$H NMR (DMSO-d$_6$) δ: 7.81 (d, J=8.4 Hz, 2H), 7.59 (br s, 1H), 7.53 (d, J 8.4 Hz, 2H), 7.00 (br s, 1H), 3.52 (s, 2H), 3.27 (q, J=7.2 Hz, 2H), 1.10 (t, J=7.6 Hz, 3H).

Synthesis of Compound 15-13

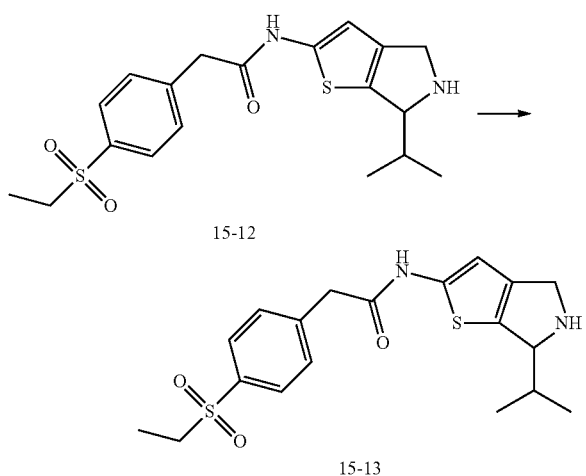

A solution of Compound 15-12 (0.09 g, 182.69 μmol, 1 eq) in hydrochloric acid-dioxane (3 mL) was stirred at room temperature for 16 hours. When LC-MS showed the completion of the reaction, the reaction solution was concentrated under reduced pressure to remove dioxane, so as to give the hydrochloride of Compound 15-13.

MS (ESI) m/z: 393.2 [M+H]$^+$

Synthesis of Example 14 and Example 15

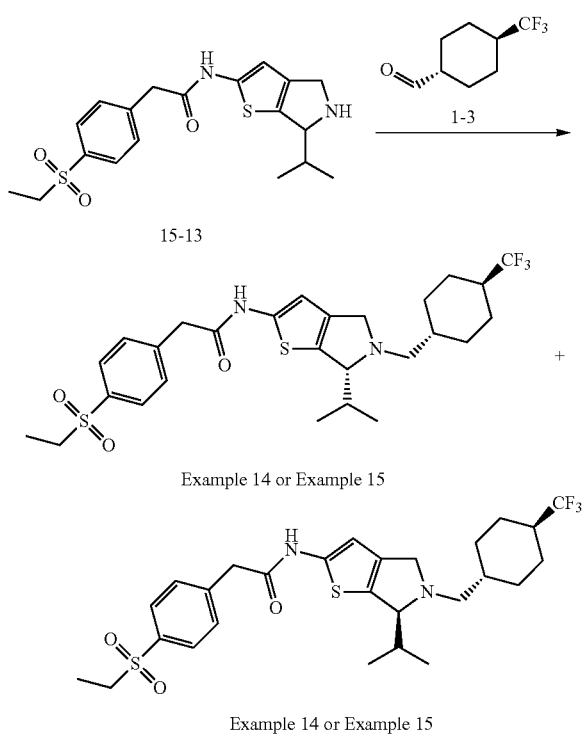

Triethylamine (20.76 mg, 205.13 μmol, 28.55 μL, 1.1 eq) was added to a solution of Compound 15-13 (0.08 g, 186.48 μmol, 1 eq, HCl) in anhydrous dichloroethane (3 mL), the resulting mixture was stirred at 20° C. for 0.5 hours, and acetic acid (11.20 mg, 186.48 μmol, 10.67 μL, 1 eq) was then added to adjust the pH to 5, followed by the addition of Compound 1-3 (101.36 mg, 559.45 μmol, 3 eq) and NaBH(OAc)$_3$ (118.57 mg, 559.45 μmol, 3 eq). The reaction solution was stirred at 20° C. for 1 hour. When LC-MS showed the completion of the reaction, a saturated ammonium chloride solution was added to quench the reaction, and the resulting mixture was then extracted with dichloromethane (6 mL×2). The combined organic layers were washed with saturated brine (8 mL) and then dried over anhydrous sodium sulfate to give a crude product. The crude product was purified by preparative thin-layer chromatography and separated by SFC (SFC separation conditions: (column: DAICEL CHIRALCEL OD-H 250 mm×30 mm, 5 μm); mobile phase: phase A was supercritical fluid carbon dioxide, and phase B was methanol containing 0.1% aqueous ammonia, wherein the volume ratio of phase B was 40%) to obtain Example 14 and Example 15.

Example 14

The retention time Rt of the SFC analysis was 3.983 min. The SFC analysis conditions were as follows: (column: Chiralcel OD-3 150 mm×4.6 mm, I.D. 3 μm); mobile phase: phase A was supercritical fluid carbon dioxide, and phase B was methanol containing 0.05% diethylamine; gradient: the volume ratio of mobile phase B was increased from 5% to 40% within 4.5 minutes, kept at 40% for 2.5 minutes, and then kept at 5% for 1 minute; flow rate: 2.8 mL/min; column temperature: 40° C.

MS (ESI) m/z: 557.1 [M+H]$^+$;

$^1$H NMR (CHLOROFORM-d) δ: 7.82 (d, J 8.4 Hz, 2H), 7.49 (br d, J=7.6 Hz, 2H), 6.36 (s, 1H), 4.14 (br d, J=6.4 Hz, 1H), 3.77 (s, 2H), 3.40 (br s, 1H), 3.05 (q, J=7.4 Hz, 2H), 2.55 (br s, 1H), 2.14 (br d, J=12.4 Hz, 1H), 1.85-1.98 (m, 3H), 1.78 (br d, J=11.2 Hz, 2H), 1.17-1.29 (m, 7H), 0.97 (br d, J=7.2 Hz, 3H), 0.80-0.93 (m, 3H), 0.76 (br d, J=5.6 Hz, 4H).

Example 15

The retention time Rt of the SFC analysis was 4.277 min. The SFC analysis conditions were as follows: (column: Chiralcel OD-3 150 mm×4.6 mm, I.D. 3 μm); mobile phase: phase A was supercritical fluid carbon dioxide, and phase B was methanol containing 0.05% diethylamine; gradient: the volume ratio of mobile phase B was increased from 5% to 40% within 4.5 minutes, kept at 40% for 2.5 minutes, and then kept at 5% for 1 minute; flow rate: 2.8 mL/min; column temperature: 40° C.

MS (ESI) m/z: 557.1 [M+H]$^+$;

$^1$H NMR (CHLOROFORM-d): δ 7.79 (br d, J=8.4 Hz, 2H), 7.55 (br s, 2H), 6.44 (br s, 1H), 3.84 (br s, 2H), 3.04 (q, J=7.2 Hz, 2H), 2.17 (br s, 1H), 1.74-2.00 (m, 4H), 1.13-1.34 (m, 9H), 1.02 (br s, 5H), 0.83 (br s, 6H).

Bioactivity Experiment 1-A: In Vitro Test for Inhibitory Activity on RORγ

1. Test Method

Reporter cells: Reporter cells expressing a chimeric RORγ receptor were used in this experiment. The chimeric RORγ receptor was a RORγ receptor formed by replacing the N-terminal DNA-binding domain of the natural RORγ protein with the DNA-binding domain of the yeast Gal4 protein. The luciferase reporter gene was located at the downstream of the Gal4 activating sequence (UAS). The details were as shown in the table below:

| Receptor (gene symbol) | Receptor Form --- Reporter gene | Host cell line | Reference |
|---|---|---|---|
| RORγ | Gal4 hybrid receptor --- Gal4 upstream activating sequence -- luciferase | HEK293 | Inverse agonist, i.e., ursolic acid |

Step 1: Reporter cells were prepared into a cell suspension using INDIGO's Cell Recovery Medium (CRM, containing 5% fetal bovine serum treated by activated carbon). The cell suspension was dispensed into a white 96-well culture plate in a volume of 100 μl/well.

Step 2: Eight concentration gradients were set for each test compound, and the test was conducted twice at each concentration. Prior to the experiment, the main stock solution of the test compound was serially diluted with DMSO, so as to formulate solutions with "1000×-concentration" relative to each of the final test concentrations. Subsequently, the compound was further diluted with the cell recovery medium (CRM, containing 5% fetal bovine serum treated by activated carbon), so as to formulate test working solutions with "2×-concentration". As per a volume of 100 μl/well, the test working solutions were respectively added to the test wells in which the reporter cells were added in advance, so as to obtain the desired final test concentrations. The residual concentrations of DMSO in all test wells were 0.1%. The test plate was incubated in a cell incubator for 24 hours. Conditions of the incubator were set as follows: temperature: 37° C., 5% $CO_2$, humidity: ~85%.

Step 3: After 24 hours of incubation, the liquid in the culture plate was discarded, 100 μl of luciferase detection reagent was added to each test well, and then, the fluorescence intensity (Relative Luminescence Units, RLUs) in each well was read.

Inspection of the Test:

In this test, the reference compound ursolic acid was used as an internal standard of a positive compound to verify the inhibitory effect of the test compound on RORγ in reporter cells of a specific batch. The tests for the reference compound and the test compound were performed simultaneously, and the reference compound and the test compound were thus exposed to the same test reagent and environment. The reference compound group containing 0.1% DMSO as solvent was used as an internal standard of a positive compound, so as to determine the effect of the solvent DMSO on the test results and calculate the percentage reduction in RORγ activity.

2. Data Processing

The test data was managed and archived by Microsoft Excel, and mean±standard deviation (SD) of RLU, fold of reduction, inhibition rate, coefficient of variation (% CV) and Z factor were calculated.

Coefficient of variation (% CV): 100×(SD/Ave. RLU);

Fold of reduction for inverse agonist: [Ave. $RLU^{vehicle}$/Ave. $RLU^{test\ compound}$].

Percentage reduction for inverse agonist: 100×(1− [Ave. $RLU^{test\ compound}$/Ave. $RLU^{vehicle}$]);

Theoretically, the minimum reduction (0% reduction) was shown in the solvent control group free of compound;

Z factor: $1-[(3\times[SD^{vehicle}+SD^{test\ compound}])/(RLU^{vehicle}-RLU^{test\ compound})]$.

3. Graphic Data Processing Method

The dose-response curves (DRCs) of the reference compound and the test compound in the tests aiming at ROR γ were obtained by non-linearly fitting the inhibition rate of ROR γ activity and the logarithmic values of the concentrations of the compounds using the GraphPad Prism software.

4. Test Results

The results of the in vitro screening test for the compounds of the Examples were shown in Table 1 in detail.

TABLE 1

Results of the In Vitro Screening Test for the Compounds of the Examples

| Test Samples | Value of the concentration required for 50% Inhibition ($EC_{50}$) of RORγ | Specific value of the concentration required for 50% inhibition (EC50) of RORγ |
|---|---|---|
| Example 1 (in free state) | A | 15.8 nM |
| Example 3 (in free state) | B | 147 nM |

Definition of bioactivity: A: $EC_{50} \leq 100$ nM; B: 100 nM $< EC_{50} \leq 500$ nM; C: 500 nM $< EC_{50} \leq 1000$ nM; D: 1000 nM $< EC_{50} \leq 5000$ nM.

Bioactivity Experiment 1-B: In Vitro Test for Inhibitory Activity on RORγ: TR-FRET Screening The compounds of the present application was able to regulate (inhibit) the bioactivity of the nuclear receptor RORγ, and the strength of this regulatory (inhibitory) effect could be evaluated by a TR-FRET (time-resolved fluorescence resonance energy transfer) screening system. Nuclear receptor cofactors (co-activators and co-inhibitors) could regulate the transcription of a target gene by the interaction with nuclear receptors. If a ligand (test compound) affected the interaction between the nuclear receptors and the cofactors, this ligand (test compound) was able to regulate the transcription of the corresponding gene.

This method adopted the TR-FRET (time-resolved fluorescence resonance energy transfer) technique to determine the ability of a compound to regulate the interaction between the polypeptide indirectly bound to APC (phycocyanin) (namely, APC was indirectly bound to the polypeptide by binding to Streptavidin and biotin) and RORC2-LBD linked to a europium (Eu)-labeled anti-His antibody (Perkin Elmer #AD0111). In the absence of the compound, RORC2 could bind to an APC-modified polypeptide. If the compound was an agonist, it could enhance the interaction between RORC2 and the APC-modified polypeptide after binding to RORC2. On the contrary, if the compound was an inverse agonist, it could inhibit the interaction between RORC2 and the APC-modified polypeptide after binding to RORC2. When the APC-modified polypeptide and the Eu-labeled anti-His antibody-RORC2-LBD complex approached to each other and the distance therebetween was within a certain distance, energy transfer could occur and a TR-FRET signal was generated.

(1) The final concentrations and reaction conditions of the reaction system of this method were as shown in the following table.

| Concentration of RORc-LBD | Biotin-labeled SRC1 peptide | APC-labeled Streptavidin | Concentration of the Eu-labeled anti-His antibody | Total volume (μL) | Reaction conditions |
|---|---|---|---|---|---|
| 15 nM | 200 nM | 50 nM | 1 nM | 25 | 4° C., overnight |

SRC1 peptide: a polypeptide containing LXXLL-motif and capable of binding to RORC2-LBD; wherein LXXLL-motif referred to a structural sequence containing LXXLL, in which L referred to leucine and X referred to any amino acid.

2. Experimental Method 2.1 Formulation of Buffer Solution

A buffer solution comprising 50 mM Tris (pH 7.0), 50 mM KCl, 1 mM Na-EDTA, 0.01% BSA (0.1 mg/ml), and 0.1 mM DTT was freshly formulated prior to the experiment.

2.2 Formulation of a RORγ-Free Working Solution

Prior to the test, a working solution containing 1.67 nM Eu/anti-His and 0.75 μl/well of SF9 cell lysate was freshly formulated, and was placed on ice prior to use.

2.3 Formulation of a RORγ-containing working solution. Prior to the test, a working solution containing 1.67 nM Eu/anti-His and 0.75 μl/well of SF9 cell lysate was freshly formulated, and was placed on ice before use. 25.05 nM of RORγ was added to the working solution.

2.4 Formulation of a Mixed Solution of Peptide-Streptomycin/APC

A buffer solution containing 500 nM polypeptide and 125 nM Streptavidin/APC was freshly formulated prior to the test, and was placed on ice prior to use.

2.5 Ten concentration gradients were set for each test compound, and duplicate wells were set for each concentration. The formulating method of the test compounds was as follows:

1) aspirating 2 μl solution from the source plate in which a 10 mM solution of the compound in DMSO was added, and adding said solution to columns 1 and 11 of coming 3656;

2) adding 38 μl DMSO to columns 1 and 11 via Bravo, and diluting the compound to 500 μM;

3) transferring 10 μl of a 500 μM solution of the compound via Bravo to columns 1 and 11 of the LDV plate;

4) adding 7.5 μl DMSO to columns 2 to 10 and 12 to 22 of the LDV plate via Bravo;

5) serially diluting the compound via Bravo (4 folds, 10 doses, 2.5 μl compound+7.5 μl DMSO); and 6) transferring 250 nL solution of the compound from the dose plate to the test plate (Greiner 781076) via Echo 2.6 Operating Process of the Experiment 1) 15 μl of the RORγ-free working solution was added to column 22 of the tested 384-well plate (the final concentration of Eu/anti-His was 1 nM);

2) 15 μl of the RORγ-containing working solution was added to columns 1 to 21 of the tested 384-well plate (the final concentration of Eu/anti-His was 1 nM, and the final concentration of RORg was 15 nM); and 3) 10 μl of the mixed solution of peptide-streptomycin/APC was added to columns 1 to 22 of the tested 384-well plate (the final concentration of SA-APC was 50 nM, and the final concentration of SRC1 peptide was 200 nM);

4) the mixture in the plate was mixed thoroughly on a shaker for 2 minutes;

5) the test plate was incubated at 4° C. overnight;

6) the test plate was left at room temperature for 1 hour to reach an equilibration with the room temperature;

7) the plate was centrifuged at 1000 rpm for 1 minute;

8) the plate was read on an Envision reader; and 9) data analysis was performed using the ratio of the numerical value detected at an emission wavelength of 665 nm to the numerical value detected at an emission wavelength of 615 nm.

3. Data Analysis

GraphPad Prism software was used to plot a logarithmic curve of the TR-FRET ratio F665/F615 vs the concentration of the compound and to calculate the EC50 value. A smaller value indicated that the compound had a stronger regulatory (inhibitory) effect on the receptor RORγ.

The $EC_{50}$ values of the compounds of the present application against RORγ were listed in the following table (Table 2).

| Test Samples | Value of the concentration required for 50% inhibition ($EC_{50}$) of RORγ |
|---|---|
| Example 1 (hydrochloride) | A |
| Example 3 (free state) | B |
| Example 4 (free state) | D |
| Example 5 (hydrochloride) | D |
| Example 6 (hydrochloride) | A |
| Example 7 (hydrochloride) | A |
| Example 8 (hydrochloride) | A |
| Example 9 (hydrochloride) | A |
| Example 11 (hydrochloride) | A |
| Example 12 (hydrochloride) | A |
| Example 13 (hydrochloride) | D |

Definition of bioactivity: A: $EC_{50} \leq 100$ nM; B: 100 nM $< EC_{50} \leq 500$ nM; C: 500 nM $< EC_{50} \leq 1000$ nM; D: 1000 nM $< EC_{50} \leq 5000$ nM.

Bioactivity Experiment 2: Pharmacokinetic Evaluation

1. Experimental Method

Balb/c mice (female, 15 to 30 g, 7- to 9-week old, Shanghai Lingchang) were used to test in vivo pharmacokinetics of compounds. The experimental method was as follows.

The pharmacokinetic characteristics of the compounds were tested by standard protocols after the compounds were administered to rodents by intravenous injection and oral administration. In the experiment, candidate compounds were formulated into clear solutions and administered to mice by a single intravenous injection and a single oral administration. The vehicle for intravenous injection (IV) was a mixed solvent of 5% of DMSO and 95% of 10% Cremophor EL, and the vehicle for oral administration (PO) was a mixed solvent of 1% tween 80, 9% PEG400 and 90% water. Whole blood samples within 48 hours were collected, and centrifuged at 3000 g at 4° C. for 15 minutes. The supernatant was separated to obtain the plasma sample, to which an acetonitrile solution containing an internal standard was added to precipitate the proteins, and the volume of the acetonitrile solution was 20 times that of the plasma sample. The supernatant was obtained by centrifugation, an equal volume of water was added thereto, and the mixture was centrifuged again to get the supernatant for sample injection. Plasma concentrations were quantitatively analyzed by an LC-MS/MS analytical method, and pharmacokinetic parameters, such as peak concentration, peak time, clearance rate, half-life, area under the concentration-time curve, and bioavailability, were calculated.

Of these, "10% Cremophor EL" referred to a deionized aqueous solution of Cremophor EL with a volume concentration of 10%. For example, taking the formulation of a 100 ml solution as an example, 10 ml Cremophor EL was taken and deionized water was added thereto, the mixture was well stirred, and then deionized water was added until the total volume was 100 ml. "Mixed solvent of 5% of DMSO and 95% of 10% Cremophor EL" referred to a mixed solvent comprised of DMSO and 10% Cremophor EL, in which DMSO 10% Cremophor EL, and 10% Cremophor EL accounted for 95% of the volume of the mixed solvent. "Mixed solvent of 1% tween 80, 9% PEG400 and 90% water" meant that the volumes of tween 80, PEG400 and water accounted for 1%, 9% and 90% of the volume of the mixed solvent, respectively.

2. Test Results

The test results were as shown in Table 2.

TABLE 2

PK Paramters of the Compound of the Example in Plasma
PK Paramters of the compound (hydrochloride) of Example 1 in Plasma

| PK parameters | IV | PO |
| --- | --- | --- |
| Rsq_adj | 0.998 | 0.978 |
| No. points used for $T_{1/2}$ | 3.00 | 4.00 |
| $C_0$ (nM) | 955 | — |
| $C_{max}$ (nM) | — | 3520 |
| $T_{max}$ (h) | — | 1.00 |
| $T_{1/2}$ (h) | 6.84 | 8.70 |
| $Vd_{ss}$ (L/kg) | 3.50 | — |
| Cl (mL/min/kg) | 7.62 | — |
| $T_{last}$ (h) | 24.0 | 24.0 |
| $AUC_{0-last}$ (nM · h) | 3670 | 30872 |
| $AUC_{0-inf}$ (nM · h) | 3916 | 35142 |
| $MRT_{0-last}$ (h) | 5.91 | 7.19 |
| $MRT_{0-inf}$ (h) | 7.66 | 10.8 |
| $AUC_{Extra}$ (%) | 6.28 | 12.1 |
| $AUMC_{Extra}$ (%) | 27.8 | 41.3 |
| Bioavailability (%)[a] | — | 89.7 |

"—" indicated that the test was not performed or the data was unavailable.

Bioactivity Experiment 3: Inhibition Test of hERG Potassium Channel

1. Experimental Method (1) Preparation of Cells

CHO-hERG cells (from Shanghai Institute of Materia Medica, Chinese Academy of Sciences) were cultured in a 175 $cm^2$ culture flask. When the cell density reached 60% to 80%, the culture medium was removed, the cells were washed once with 7 mL of PBS, and then 3 mL of Detachin was added for cell detachment. After complete cell detachment, 7 mL of culture medium were added for neutralization, the mixture was then centrifuged, the supernatant was aspirated, and another 5 mL of culture medium was added for re-suspension, so as to ensure that the cell density was $2 \times 10^6$/mL to $5 \times 10^6$/mL.

(2) Formulation of Intracellular and Extracellular Fluids

TABLE 3

Compositions of Intracellular and Extracellular Fluids

| Reagents | Extracellular Fluid (mM) | Intracellular Fluid (mM) |
| --- | --- | --- |
| $CaCl_2$ | 2 | 5.374 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| $Na_2ATP$ | — | 4 |
| pH | 7.40 (adjusted with NaOH), | 7.25 (adjusted with KOH), |
| Osmotic pressure | ~305 mOsm | ~290 mOsm |

(3) Recording Process of Electrophysiology

The single-cell giga-seal and the formation of whole-cell mode were both completed automatically by a Q patch instrument. After a whole-cell recording mode was achieved, the cells were clamped at −80 mV, exposed to a front voltage of −50 mV for 50 ms prior to a depolarizing stimulus (5 s, +40 mV), and then repolarized to −50 mV for 5 s, followed by a recovery to −80 mV. This voltage stimulation was applied every 15 s and recorded for 2 minutes, and the extracellular fluid was then administered, followed by a record lasting for 5 minutes. Thereafter, the administration process was started. Starting from the lowest test concentration, the compounds were administered at each test concentration and the process lasted for 2.5 minutes. After the continuous administration of all concentrations of the compounds, 3 μM Cisapride was administered as a positive control compound. At least 3 cells (n≥3) were tested at each concentration.

(4) Preparation of the Compounds 20 mM stock solution of the compound was diluted with the extracellular fluid, and 5 μL of the 20 mM stock solution of the compound was taken, added to 2495 μL of the extracellular fluid, and diluted by 500 times to 40 μM. Thereafter, the resulting mixture was serially and successively diluted by 3 times in an extracellular fluid containing 0.2% DMSO, so as to obtain a final concentration to be tested. The highest test concentration was 40 μM, and there were 6 concentrations in total: 40 μM, 13.33 μM, 4.44 μM, 1.48 μM, 0.49 μM, and 0.16 M. The content of DMSO in the final test concentration did not exceed 0.2%, and such concentration of DMSO had no effect on hERG potassium channel.

(5) Data Analysis

The experimental data was analyzed by XLFit software.

(6) Quality Control

Environment: humidity 20% to 50%, temperature 22 to 25° C.

Reagents: The experimental reagents used herein were purchased from Sigma, purity >98%

The experimental data in the report must meet the following standards:

whole-cell sealing impedance >100 MΩ tail current amplitude >400 pA

Pharmacological Parameters:

Inhibitory effects of multiple concentrations of Cisapride on hERG channel were set as the positive control.

(7) Test Results

Results of IC50 value of the compounds of Examples against hERG were as shown in Table 4.

TABLE 4

Results of IC50 value of the compounds of Examples against hERG

| Test Samples | hERG IC50 (μM) | Inhibition rate (%) at the maximum concentration |
|---|---|---|
| Example 1 (hydrochloride) | >40 | 26.33 |
| Cisapride | 0.05 | 89.61 |

Bioactivity Experiment 4: In Vivo Pharmacodynamic Research on MOG35-55-Induced Experimental Autoimmune Encephalomyelitis (EAE) in Mice Experimental Method:

1. Preparation of MOG/CFA Emulsion

Preparation of CAF: *M. tuberculosis* H37Ra was weighed, placed in an agate mortar, and ground into fine powder. IFA was added thereto, and the mixture was formulated into a 4 mg/ml suspension.

Preparation of MOG35-55 solution: MOG35-55 was weighed, dissolved in physiological saline, and formulated into a 2 mg/ml solution, which was used immediately after it was formulated.

2 mg/ml MOG35-55 and 4 mg/ml CFA were mixed in equal volume in a 40-ml glass bottle and homogenized with a homogenizer for 1 h (homogenization was performed for 45 s and then paused for 15 s), so as to prepare a MOG/CFA emulsion, which was kept on ice for later use.

2. Preparation of PTX Solution

Preparation of PTX solution: 1 ml PBS was added to PTX powder (50 μg for each vial) to formulate into a 50 μg/ml stock solution. The stock solution was diluted with PBS to 1 μg/ml before use, and was used immediately after it was formulated.

3. Induction of EAE

The day of immunization was recorded as day 0, and the subsequent days were marked sequentially. Mice were anesthetized with isoflurane, and 100 μl of the emulsion was administered via subcutaneous injection at three sites (the middle part between shoulder and back, and two sides of the tail that were close to the groin), namely, 33 μl of the emulsion for each site. 0 hour and 48 hours after the injection of the emulsion, 200 ng (i.e. 200 μl) of the PTX solution was intraperitoneal injected. Mice in the normal group were not required to be immunized.

4. Designs for Administration and Dose

After the immunization on day 0, the immunized mice were randomly divided into 3 groups with 10 mice in each group according to the body weights except for the mice in the normal group, the details were shown in Table 1. FTY720 served as a positive drug, and a dose of 0.05 mg/ml was an effective dose commonly used in the EAE model.

The first group was normal mice without any treatment; vehicle was administered to the second group; FTY720 was administered to the third group at a dose of 0.5 mg/kg once a day; and the compound of Example 1 was administered to the fourth group at a dose of 75 mg/kg twice a day. The administration lasted for 25 days in total. The volume of intragastric administration was 10 ml/kg.

TABLE 5

Grouping and Dose Design

| Group | Test Drugs | QTY. | Administration Route | Concentration mg/mL | Dose mg/kg | Dosing Frequency |
|---|---|---|---|---|---|---|
| G1 | Normal (blank control) | 5 | N/A | N/A | N/A | NA |
| G2 | Vehicle (solvent control)* | 10 | p.o. | N/A | N/A | b.i.d, 25 days |
| G3 | FTY720** | 10 | p.o. | 0.05 | 0.5 | qd, 25 days |
| G4 | Example 1 (hydrochloride)* | 10 | p.o. | 7.5 | 75 | b.i.d, 25 days |

*vehicle: a mixed solvent of DMSO/PEG400/H$_2$O, wherein the volume ratio of DMSO/PEG400/H$_2$O was 5:20:75.
**vehicle (solvent): DDH$_2$O.

5. Surveillance of the Indicators of the Onset of Disease

The day when animals were immunized was day 0. Animal body weights were recorded three times a week from day 0 to day 10, and the body weights and clinical scores of the animals were closely observed and recorded daily from day 11. The scoring criteria were as shown in the following table.

TABLE 6

Clinical Scoring Criteria

| Score | Clinical Symptoms |
|---|---|
| 0 | Normal performance, no obvious sign of disease |
| 1 | Drooping tail and weakness in single hind limb |
| 2 | Drooping tail, weakness in both hind limbs, and staggering gait |
| 3 | Weakness and paralysis in single hind limb |
| 4 | Weakness and paralysis in both hind limbs |

6. Statistical Process

The experimental data was expressed as mean±standard error of mean (Mean±SEM). AUC of clinical scores was analyzed by one-way analysis of variance (One-way ANOVA), and the difference was considered as significant when $p<0.05$.

7. Experimental Results (1) Clinical Scores

On day 13 after immunization, mice began to develop clinical symptoms of EAE. The average clinical score of G2 (solvent control group) gradually increased and reached 3.6 points on day 18, indicating the successful establishment of the model (see FIG. 1). In G4 (the compound of Example 1), the clinical scores of EAE mice in the experiment were significantly reduced (see FIG. 1).

(2) Results of Inhibition Rate

Figure 2:
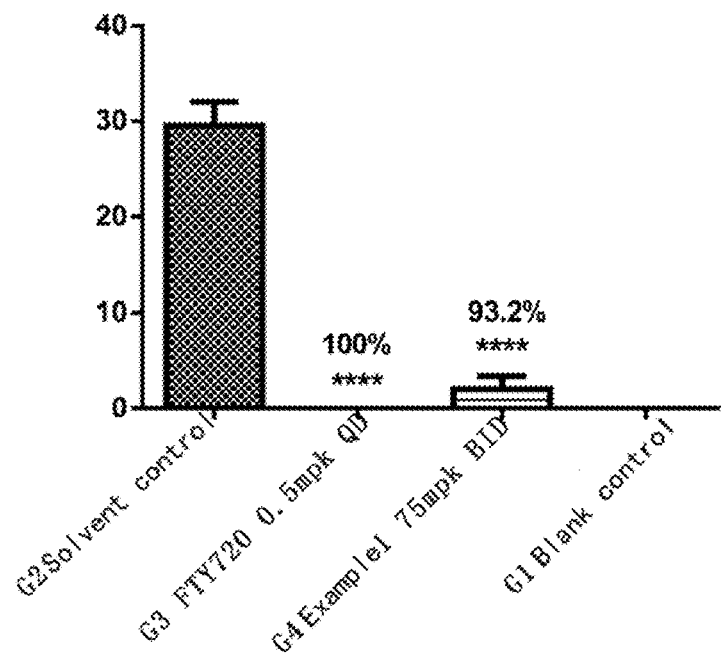
FIG. 2 shows the results of inhibitory rate of the in vivo pharmacodynamic research on MOG35-55-induced experimental autoimmune encephalomyelitis (EAE) in mice.

The area under the curve of clinical scores over time (i.e. "AUC of clinical scores" or "area under the curve of clinical scores") was calculated by analyzing the curve of clinical scores for each animal in each group, and the inhibition rates of the remaining groups (G1, G3, and G4) relative to G2 (solvent control group) were calculated by the mean AUC of clinical scores among groups. The results were shown in FIG. 2. The compound of Example 1 was capable of significantly reducing the AUC of clinical scores of the animals suffering from EAE ($p<0.0001$, compared to the solvent control group) with an inhibition rate of 93.2%. The positive drug FTY720 could completely inhibit the clinical scores of the animals suffering from EAE, and the inhibition rate was 100%.

(3) Results of Morbidity

Figure 3:
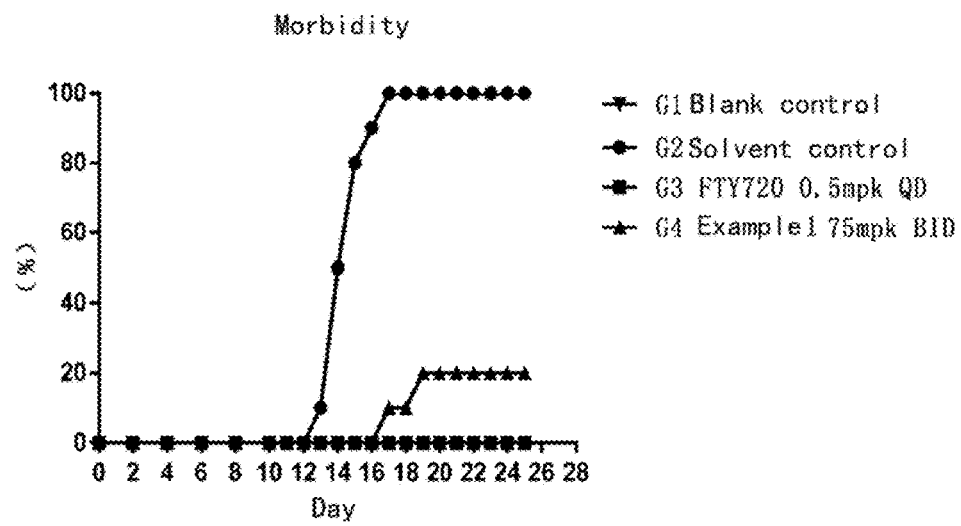
FIG. 3 shows the results of morbidity of the in vivo pharmacodynamic research on MOG35-55-induced experimental autoimmune encephalomyelitis (EAE) in mice.

Results of the morbidity of EAE were as shown in FIG. 3. The morbidity in G4 (the compound of Example 1) was 20% at day 19 and was stable till the end of the experiment, which showed a good effect. The incidence of EAE in G2 (solvent control group) reached 100% on day 17 post immunization and was maintained at 100%. The morbidity in G3 (positive control FTY720 group) was 0 from the beginning to end (see FIG. 3).

(4) Results of Body Weight Changes

Figure 4:
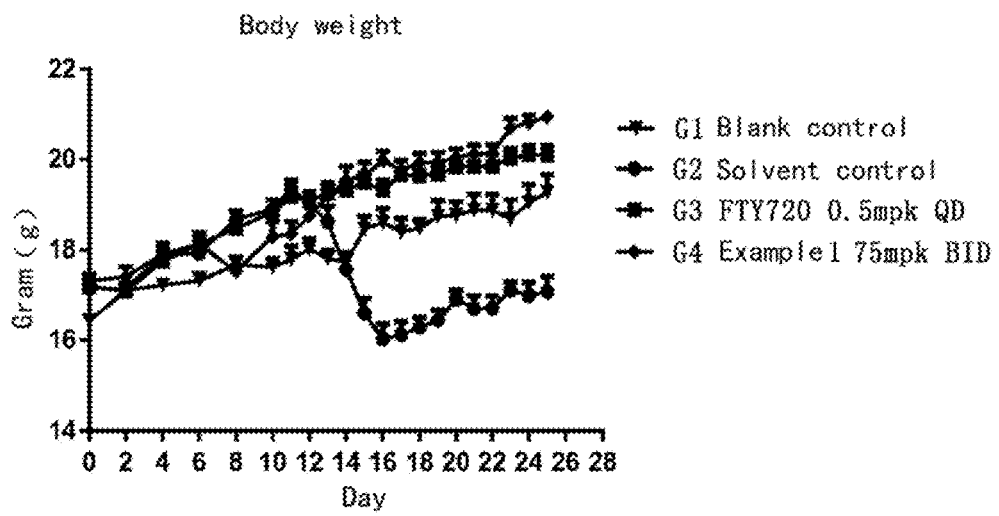
FIG. 4 shows the body weight changes in the in vivo pharmacodynamic research on MOG35-55-induced experimental autoimmune encephalomyelitis (EAE) in mice.

As compared with G1 (normal group), the body weights of the mice in G2 (solvent control group) decreased on day 12, decreased sharply from day 12 to day 16, and recovered slowly from day 17. The body weights in G3 (positive control FTY720 group) and G4 (the compound of Example 1) kept increasing with a same tendency, and were significantly different from those of the solvent control group. Moreover, the body weights in G4 (the compound of Example 1) were the highest from the beginning to end (FIG. 4).

Bioactivity Experiment 5: In Vivo Pharmacodynamic Study of the Therapeutic Efficacy and Mechanism Studies in Mouse Psoriasis (IMQ) Model Experimental Method:

5.1 Animal Grouping and the Establishment of an Imiquimod-Induced Psoriasis Model in Mice 6- to 8-week old female C57BL/6 mice were selected, depilated on the backs, and sensitized two days later except for the sham operation group. On the day of sensitization, the mice were randomly divided into the following 6 groups (8 mice per group). Group I was a sham operation group; Group II was a vehicle control group and PBS was administered; Group III was a positive control group and 5 mg/kg methotrexate was administered; Groups IV, V and VI were ip treatment group, ig treatment group, and topical treatment group of the compound of Example 1, and 75 mg/kg of the compound of Example 1 was administered via intraperitoneal injection, intragastric administration, and dorsal application, respectively. Administration was started on the day of sensitization, once daily for Group III and twice daily for Groups IV to VI. On the day of sensitization, the mice in Groups II to VI were given 60 to 80 mg of imiquimod cream (5%) on the dorsal skin for 4 consecutive days. (Please refer to Bouchaud, G., et al., *Epidermal IL-15Ralpha acts as an endogenous antagonist of psoriasiform inflammation in mouse and man*. J. Exp. Med., 2013. 210(10): p. 2105-17.)

The mice were weighed daily from the day of sensitization, and the skin scales, induration, and erythema were observed and scored according to a four-grade scoring method: 0 point, no disease; 1 point, mild; 2 points, moderate; 3 points, severe; and 4 points, very severe. (Please refer to Qin, S., et al., *Endogenous n-3 polyunsaturated fatty acids protect against imiquimod-induced psoriasis-like inflammation via the IL-17/IL-23 axis*. Mol Med Rep, 2014. 9(6): p. 2097-104.)

Figure 5:
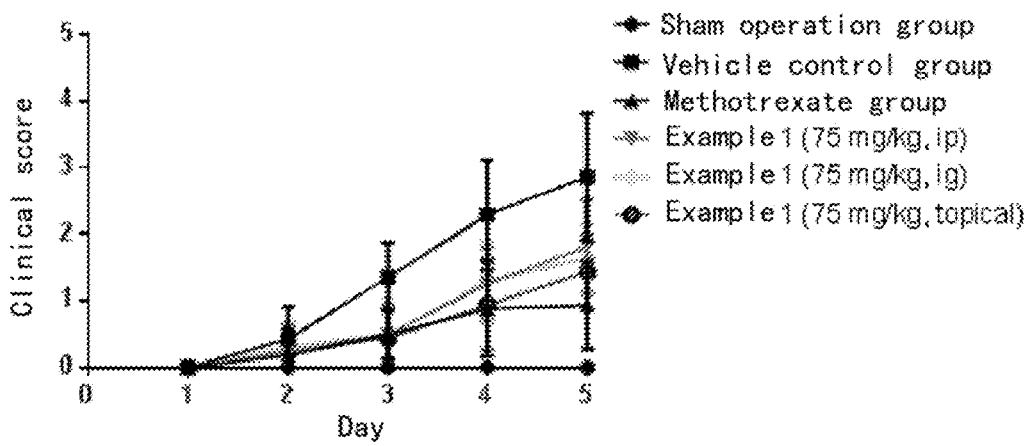
FIG. 5 shows the results of clinical scores of the in vivo pharmacodynamic research on imiquimod (IMQ)-induced experimental psoriasis in mice.

5.2 Research Results: Effect of Example 1 on the Clinical Scores of the Mice Suffering from Imiquimod-Induced Psoriasis As shown in FIG. 5, Example 1 was able to inhibit skin scales, induration and the like in the imiquimod-induced psoriasis model in mice, wherein 75 mg/kg of Example 1 administered by intraperitoneal injection, intragastric administration and dorsal application was able to reduce the clinical scores significantly (p<0.01), and its effect on reducing the clinical scores was equivalent to the effect caused by 5 mg/kg of methotrexate.

Figure 6:
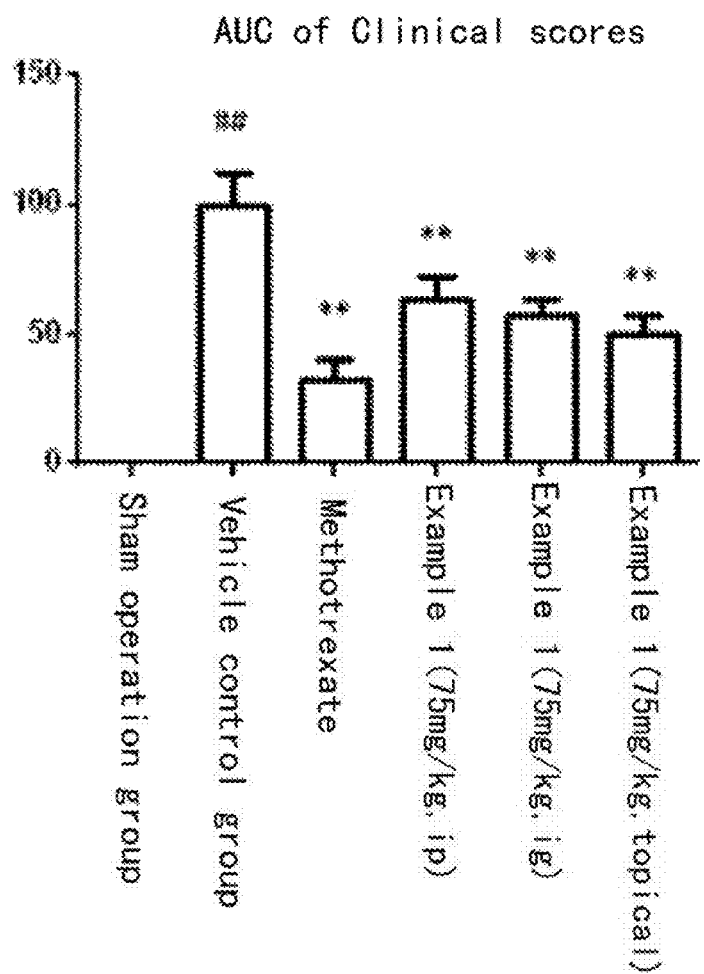
FIG. 6 shows the results of inhibitory rate of the in vivo pharmacodynamic research on imiquimod (IMQ)-induced experimental psoriasis in mice.

As shown in FIG. 6, the results of the inhibition rates of the in vivo pharmacodynamic research conducted in mice suffering from imiquimod (IMQ)-induced experimental psoriasis were shown by the relative ratios of AUC of clinical scores as described previously.

TABLE 7

Effects on the Clinical Scores of Mice Suffering from Imiquinomot-Induced Psoriasis After Daily Administration of Example 1 (Mean ± SEM, n = 8)

| Day | Sham Operation Group | Vehicle Control Group | Methotrexate (5 mg/kg, ig) |
|---|---|---|---|
| 1 | 0 ± 0 | 0 ± 0 | 0 ± 0 |
| 2 | 0 ± 0 | 0.43 ± 0.17 | 0.19 ± 0.13 |
| 3 | 0 ± 0 | 1.36 ± 0.18 | 0.50 ± 0.13 |
| 4 | 0 ± 0 | 2.29 ± 0.29 | 0.88 ± 0.25 |
| 5 | 0 ± 0 | 2.86 ± 0.34 | 0.93 ± 0.23 |

| Day | Example 1 (hydrochloride) (75 mg/kg, ip) | Example 1 (hydrochloride) (75 mg/kg, ig) | Example 1 (hydrochloride) (75 mg/kg, topical) |
|---|---|---|---|
| 1 | 0 ± 0 | 0 ± 0 | 0 ± 0 |
| 2 | 0.25 ± 0.13 | 0.31 ± 0.13 | 0.25 ± 0.13 |
| 3 | 0.50 ± 0.16 | 0.50 ± 0.19 | 0.44 ± 0.15 |
| 4 | 1.25 ± 0.19 | 1.29 ± 0.21 | 0.94 ± 0.24 |
| 5 | 1.81 ± 0.25 | 1.64 ± 0.18 | 1.43 ± 0.20 |

What is claimed is:

1. A compound of formula (I) or a pharmaceutically acceptable salt thereof, wherein the compound of formula (I) has a structure represented by formula (I-A)

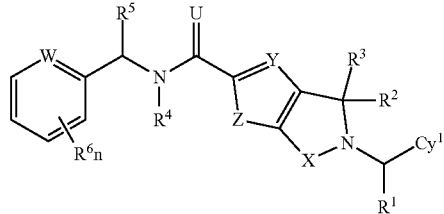

Formula I-A wherein,

X is $CR^7R^8$ or $NR^9$;

Y is $CR^{10}$;

Z is $CR^{11}R^{12}$, $NR^{13}$, —O— or —S—;

U is

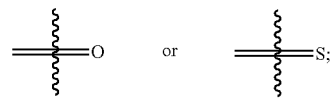

W is CH or N;

$Cy^1$ is selected from 3- to 6-membered cycloalkyl, 6- to 10-membered aryl or 5- to 10-membered heteroaryl, which is optionally substituted by one or more $R^{16}$;

$R^1$, $R^4$, $R^9$, and $R^{13}$ are independently selected from hydrogen or $C_{1-6}$ alkyl;

$R^2$ and $R^3$ are independently selected from hydrogen, halogen, amino, hydroxyl, nitro, cyano, or $C_{1-6}$ alkyl; or $R^2$ and $R^3$ form

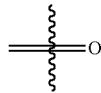

together; or $R^2$ and $R^3$ together with the C atom to which they are attached form a 3- to 6-membered cycloalkyl;

$R^5$ is selected from hydrogen or $C_{1-6}$ alkyl; the $C_{1-6}$ alkyl is optionally substituted by one or more hydroxyl, amino, nitro, cyano, halogen, $C_{1-4}$ alkoxy, $C_{1-4}$ alkylamino, or di($C_{1-4}$ alkyl)amino;

n is 0, 1, 2, 3, 4, or 5;

$R^6$ is selected from hydroxyl, amino, nitro, cyano, halogen, or

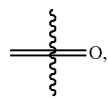

$R^7$ and $R^8$ are independently selected from hydrogen, halogen, amino, hydroxyl, nitro, cyano, or $C_{1-6}$ alkyl, wherein the $C_{1-6}$ alkyl is optionally substituted by halogen, amino, hydroxyl, nitro, cyano, or 3- to 6-membered cycloalkyl; or $R^7$ and $R^8$ form

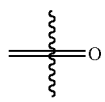 [SMILES: *=O]

together; or $R^7$ and $R^8$ together with the C atom to which they are attached form a 3- to 6-membered cycloalkyl;

$R^{10}$ is selected from hydrogen, $C_{1-6}$ alkyl, halogen, amino, hydroxyl, nitro, cyano, or $C_{1-6}$ haloalkyl;

$R^{11}$ and $R^{12}$ are independently selected from hydrogen, halogen, amino, hydroxyl, nitro, cyano, or $C_{1-6}$ alkyl; or $R^{11}$ and $R^{12}$ form

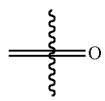

together; or $R^{11}$ and $R^{12}$ together with the C atom to which they are attached form a 3- to 6-membered cycloalkyl;

$R^{14}$ is present or not present; when $R^{14}$ is present,

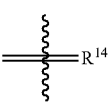

is selected from

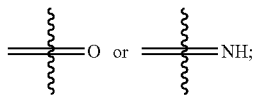

or $R^{15}$ is selected from $C_{1-6}$ alkyl or $C_{1-6}$ alkoxy;

$R^{16}$ is selected from hydroxyl, amino, nitro, cyano, halogen, $C_{1-4}$ alkyl, $C_{1-4}$ haloalkyl, $C_{1-4}$ alkoxy, and $C_{1-4}$ haloalkoxy; and when the compound of formula (I) has a structure represented by formula (I-A), X is $CR^7R^8$, U is

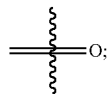

Y is $CR^{10}$, and W is CH, then $Cy^1$ is not a benzene ring.

2. The compound of claim 1, wherein U is

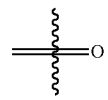 [SMILES: *=O]

and W is CH; or

U is

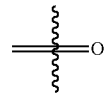

and W is N.

3. The compound of claim 1, wherein X is $CR^7R^8$ or $NR^9$; wherein $R^7$ and $R^8$ are independently selected from hydrogen, fluorine, chlorine, bromine, iodine, amino, hydroxyl, nitro, cyano, or $C_{1-3}$ alkyl, wherein the $C_{1-3}$ alkyl is optionally substituted by fluorine, chlorine, bromine, iodine, amino, hydroxyl, nitro, cyano, or 3- to 6-membered cycloalkyl; or $R^7$ and $R^8$ form

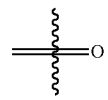 [SMILES: *=O]

together; or $R^7$ and $R^8$ together with the C atom to which they are attached form cyclopropyl, cyclobutyl, cyclopentyl, or cyclohexyl; $R^9$ is selected from hydrogen or $C_{1-3}$ alkyl.

4. The compound of claim 1, wherein Y is $CR^{10}$; wherein $R^{10}$ is selected from hydrogen, $C_{1-3}$ alkyl, fluorine, chlorine, bromine, iodine, amino, hydroxyl, nitro, cyano, or $C_{1-3}$ fluoroalkyl.

5. The compound of claim 1, wherein Z is $CR^{11}R^{12}$, $NR^{13}$, —O—, or —S—; wherein $R^{11}$ and $R^{12}$ are independently selected from hydrogen, fluorine, chlorine, bromine, iodine, amino, hydroxyl, nitro, cyano, or $C_{1-3}$ alkyl; or $R^{11}$ and $R^{12}$ form

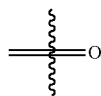 [SMILES: *=O]

together; or R¹¹ and R¹² together with the C atom to which they are attached form cyclopropyl, cyclobutyl, cyclopentyl, or cyclohexyl; R¹³ is selected from hydrogen or $C_{1-3}$ alkyl.

6. The compound of claim 1, wherein $Cy^1$ is selected from cyclohexyl or phenyl, which is optionally substituted by one or more R¹⁶; wherein R¹⁶ is selected from hydroxyl, amino, nitro, cyano, fluorine, chlorine, bromine, iodine, $C_{1-2}$ alkyl, $C_{1-2}$ haloalkyl, $C_{1-2}$ alkoxy, $C_{1-2}$ haloalkoxy.

7. The compound of claim 1, wherein R¹ and R⁴ are selected from hydrogen or $C_{1-3}$ alkyl.

8. The compound of claim 1, wherein R² and R³ are independently selected from hydrogen, fluorine, chlorine, bromine, iodine, amino, hydroxyl, nitro, cyano, or $C_{1-3}$ alkyl; or R² and R³ form

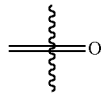 [SMILES: *=O]

together; or R² and R³ together with the C atom to which they are attached form cyclopropyl, cyclobutyl, cyclopentyl, or cyclohexyl.

9. The compound of claim 1, wherein R⁵ is selected from hydrogen or $C_{1-3}$ alkyl; said $C_{1-3}$ alkyl is optionally substituted by one or more hydroxyl, amino, nitro, cyano, fluorine, chlorine, bromine, iodine, $C_{1-2}$ alkoxy, $C_{1-2}$ alkylamino, or di($C_{1-2}$ alkyl)amino.

10. The compound of claim 1, wherein n is 0, 1, or 2.

11. The compound of claim 1, wherein R⁶ is selected from hydroxyl, amino, nitro, cyano, fluorine, chlorine, bromine, iodine,

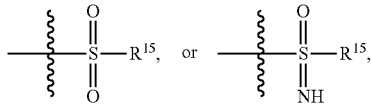

wherein R¹⁵ is selected from $C_{1-3}$ alkyl or $C_{1-3}$ alkoxy.

12. The compound of claim 1, wherein the compound of formula (I) has a structure represented by formula (I-A-1):

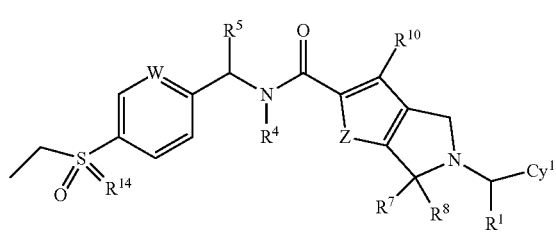

Formula I-A-1 wherein W, Z, $Cy^1$, R¹, R⁴, R⁵, R⁷, R⁸, R¹⁰ and R¹⁴ are as defined in claim 1.

13. The compound of claim 1, wherein X is $CH_2$, $C(CH_3)_2$, C=O, $CHCH(CH_3)_2$,

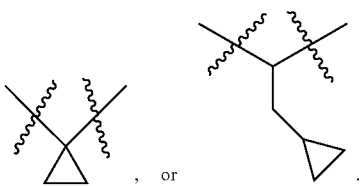 [SMILES: *C1(*)CC1 ; *C(*)CC1CC1]

14. The compound of claim 1, wherein Y is CH.

15. The compound of claim 1, wherein $Cy^1$ is selected from cyclohexyl or phenyl, which is optionally substituted by one $CF_3$.

16. The compound of claim 1, wherein R⁶ is selected from

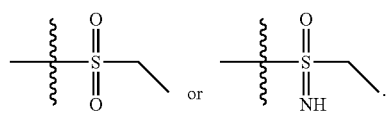

17. The compound or a pharmaceutically acceptable salt thereof according to claim 1, wherein the compound is:

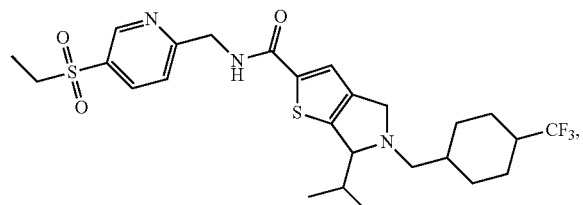

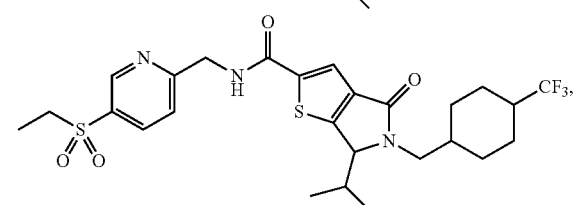

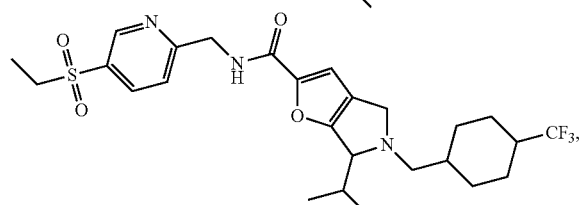

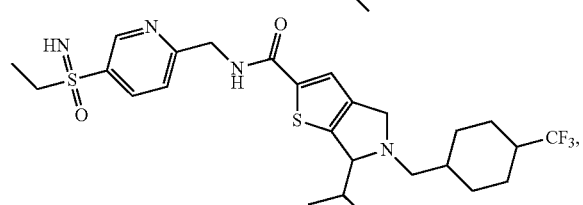

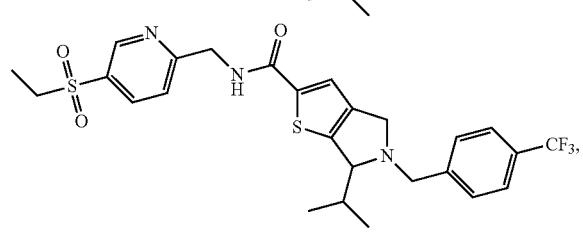

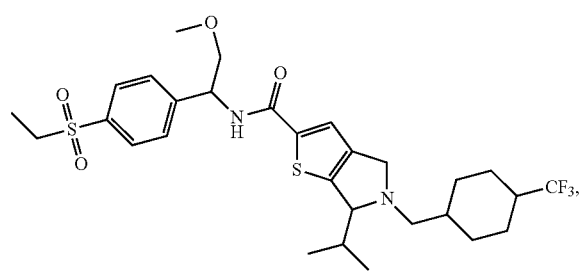
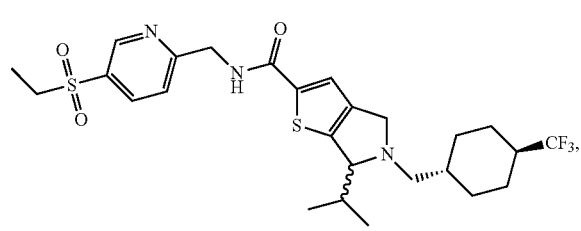
18. The compound or a pharmaceutically acceptable salt thereof according to claim 1, wherein the compound is:
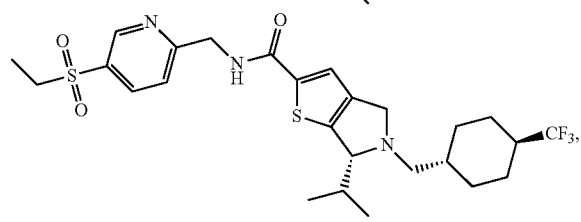
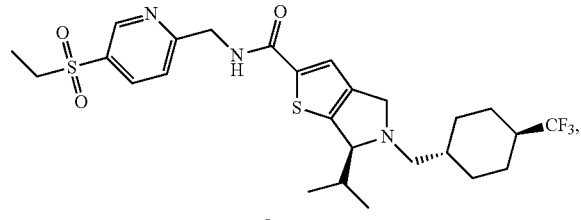
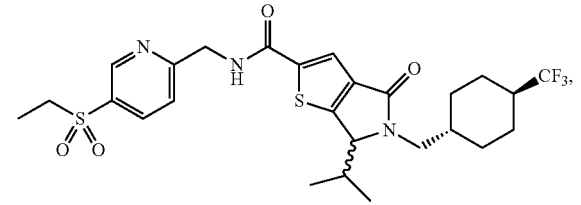
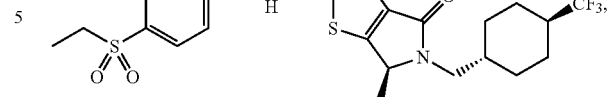
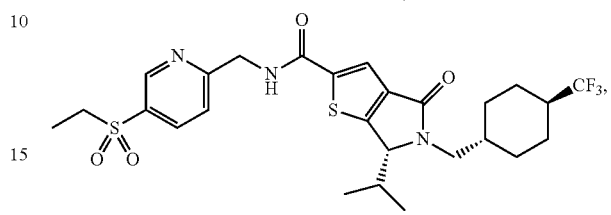
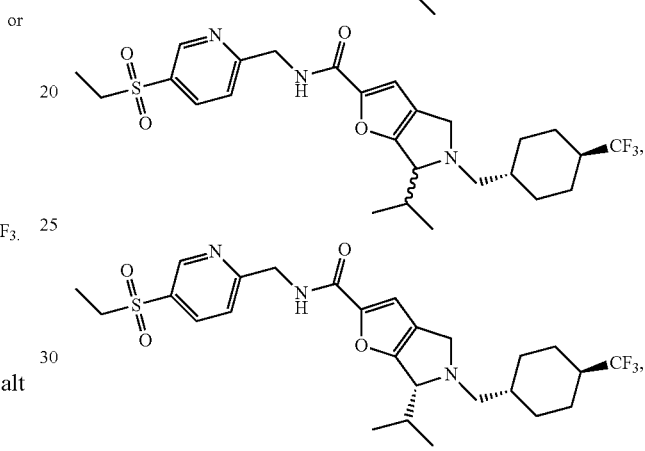
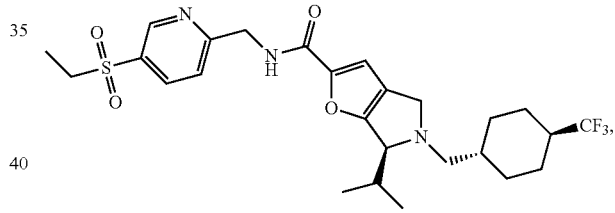
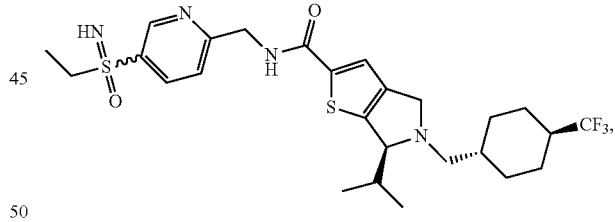
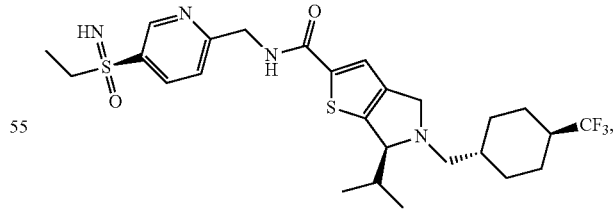
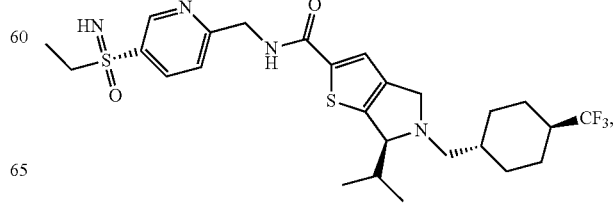

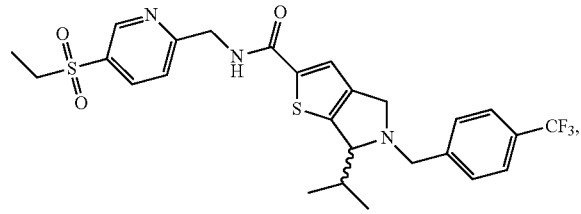

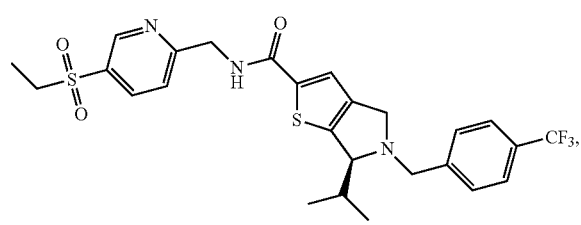

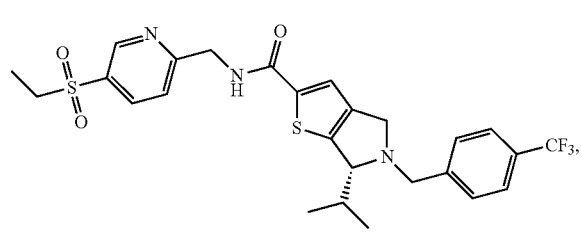

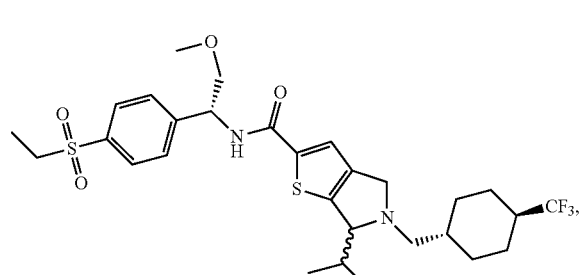

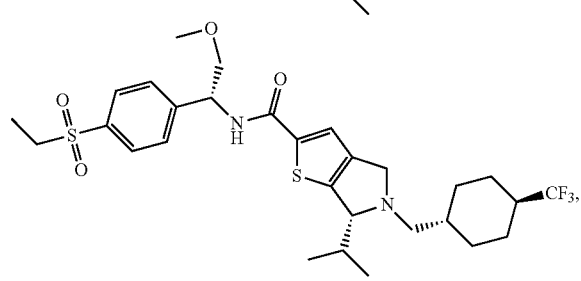

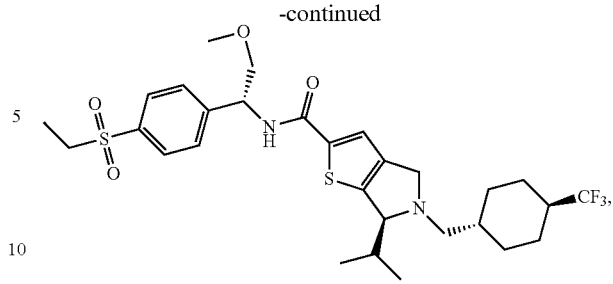

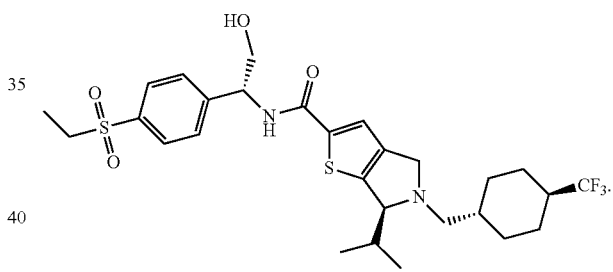

or

19. A pharmaceutical composition, comprising the compound of formula (I) or a pharmaceutically acceptable salt thereof according to claim 1 with a pharmaceutically acceptable excipient.

20. A method for inhibiting or alleviating a RORγ receptor-mediated disease in a mammal, comprising administering the compound of formula (I) or a pharmaceutically acceptable salt thereof according to claim 1, in a therapeutically effective amount to a mammal, wherein the RORγ receptor-mediated disease is selected from multiple sclerosis, rhematiod arthritis, inflammatory disease, irritable bowel syndrome or psoriasis.

* * * * *